US010856032B2

(12) United States Patent
Aimone et al.

(10) Patent No.: US 10,856,032 B2
(45) Date of Patent: *Dec. 1, 2020

(54) SYSTEM AND METHOD FOR ENHANCING CONTENT USING BRAIN-STATE DATA

(71) Applicant: INTERAXON INC, Toronto (CA)

(72) Inventors: Christopher Allen Aimone, Toronto (CA); Trevor C E Coleman, Toronto (CA); Ariel Stephanie Garten, Toronto (CA); Locillo (Lou) Giuseppe Pino, Cambridge (CA); Kapil Jay Mishra Vidyarthi, Toronto (CA); Paul Harrison Baranowski, Toronto (CA); Raul Rajiv Rupsingh, Brampton (CA); Tracy Nicole Chong, Toronto (CA)

(73) Assignee: INTERAXON INC., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/516,903

(22) Filed: Jul. 19, 2019

(65) Prior Publication Data
US 2019/0342602 A1    Nov. 7, 2019

Related U.S. Application Data

(63) Continuation of application No. 15/991,906, filed on May 29, 2018, now Pat. No. 10,405,025, which is a
(Continued)

(51) Int. Cl.
*H04N 21/422* (2011.01)
*H04N 21/43* (2011.01)
(Continued)

(52) U.S. Cl.
CPC ..... *H04N 21/42201* (2013.01); *A61B 5/0022* (2013.01); *A61B 5/0476* (2013.01);
(Continued)

(58) Field of Classification Search
CPC ............................................. H04N 21/42201
See application file for complete search history.

(56) References Cited

U.S. PATENT DOCUMENTS

| 2007/0033634 | A1 | 2/2007 | Leurs et al. |
| 2009/0150919 | A1 | 6/2009 | Lee et al. |

(Continued)

FOREIGN PATENT DOCUMENTS

| CA | 2693984 A1 | 4/2009 |
| EP | 1815784 A1 | 8/2007 |
| WO | 9749333 A1 | 12/1997 |

OTHER PUBLICATIONS

WIPO, International Search Report dated Jan. 7, 2014, issued in corresponding International Patent Application No. PCT/CA2013/001009.
(Continued)

*Primary Examiner* — Nasser M Goodarzi
*Assistant Examiner* — Adil Ocak
(74) *Attorney, Agent, or Firm* — Norton Rose Fulbright Canada LLP

(57) ABSTRACT

A computer system or method may be provided for modulating content based on a person's brainwave data, including modifying presentation of digital content at at least one computing device. The content may also be modulated based on a set of rules maintained by or accessible to the computer system. The content may also be modulated based on user input, including through receipt of a presentation control command that may be processed by the computer system of the present invention to modify presentation of content. Content may also be shared with associated brain state information.

20 Claims, 35 Drawing Sheets

Related U.S. Application Data continuation of application No. 14/096,822, filed on Dec. 4, 2013, now Pat. No. 10,009,644.

(60) Provisional application No. 61/733,223, filed on Dec. 4, 2012.

(51) Int. Cl.

| | | |
|---|---|---|
| *H04N 21/442* | (2011.01) | |
| *H04N 21/4788* | (2011.01) | |
| *G16H 40/67* | (2018.01) | |
| *A61B 5/00* | (2006.01) | |
| *A61B 5/0476* | (2006.01) | |
| *A61B 5/16* | (2006.01) | |
| *G06F 3/01* | (2006.01) | |
| *A61B 5/0205* | (2006.01) | |
| *G06Q 30/02* | (2012.01) | |
| *G06Q 50/00* | (2012.01) | |
| *H04L 12/18* | (2006.01) | |
| *G06F 19/00* | (2018.01) | |

(52) U.S. Cl.
CPC ............... *A61B 5/165* (2013.01); *G06F 3/015* (2013.01); *G06F 19/00* (2013.01); *G16H 40/67* (2018.01); *H04N 21/4307* (2013.01); *H04N 21/44204* (2013.01); *H04N 21/4788* (2013.01); *A61B 5/0006* (2013.01); *A61B 5/0205* (2013.01); *A61B 5/744* (2013.01); *A61B 5/7405* (2013.01); *A61B 5/7455* (2013.01); *G06Q 30/02* (2013.01); *G06Q 50/01* (2013.01); *H04L 12/1827* (2013.01)

(56) References Cited

U.S. PATENT DOCUMENTS

| | | |
|---|---|---|
| 2010/0201780 A1 | 8/2010 | Bennett et al. |
| 2011/0161843 A1 | 6/2011 | Bennett et al. |
| 2011/0300847 A1 | 12/2011 | Quy |
| 2012/0044365 A1 | 2/2012 | Shuster |

OTHER PUBLICATIONS

USPTO, Office Action for U.S. Appl. No. 14/096,822 dated Dec. 18, 2014.
USPTO, Office Action for U.S. Appl. No. 14/096,822 dated Sep. 29, 2015.
USPTO, Office Action for U.S. Appl. No. 14/096,822 dated Mar. 10, 2015.
USPTO, Office Action for U.S. Appl. No. 14/096,822 dated Sep. 15, 2016.
USPTO, Office Action for U.S. Appl. No. 14/096,822 dated Aug. 9, 2017.

IF I'm superfocused, rhiS iS how I TYPE! BLING BLING

Hilarious. The is the answer to stressed out people trying to use their computers.

When I'm really calm, this letters are nice an small. When I'm tense, things get different!

Facebook Post

Facebook Timeline

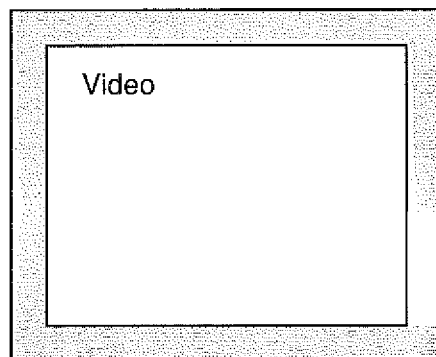
FIG.26
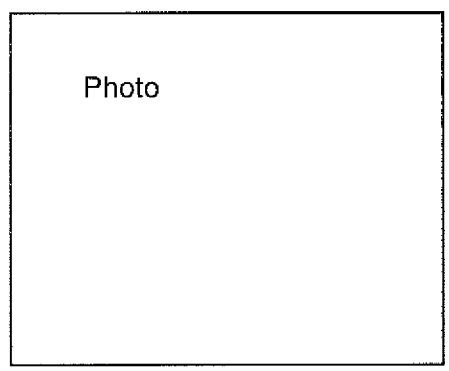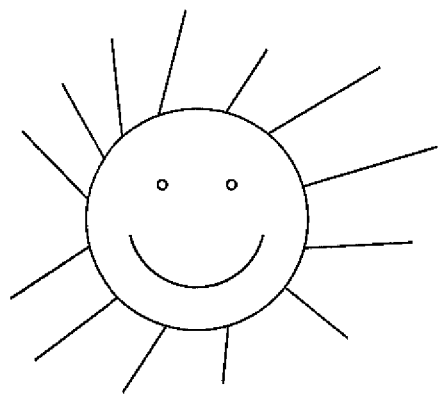
FIG.27

Progression of Photos

Content Sorted by Emotional Valence

Select a Ringtone...

When you're

| | |
|---|---|
| Stressed: | Tone 1 ▼ |
| Relaxed: | Tone 2 ▼ |
| Focused: | Tone 3 ▼ |
| Content: | Tone 4 ▼ |
| Tired: | Tone 5 ▼ |

Ad asks user to "get happy for 20% off"
if they do it, they get a coupon

| Tech Support Queue | | |
|---|---|---|
| Name | Hold Time | Anger |
| Name 1 | 1:30 | OK |
| Name 2 | 2:30 | ⚠ |
| Name 3 | 3:13 | OK |
| Name 4 | 4:19 | ! |
| Name 5 | 5:22 | ! |
| Name 6 | 1:30 | ⚠⚠ |

Call center employees can see emotional state of callers ( New Stuff )

FIG.44

SYSTEM AND METHOD FOR ENHANCING CONTENT USING BRAIN-STATE DATA

CROSS REFERENCE TO RELATED APPLICATION(S)

This application is a continuation of U.S. patent application Ser. No. 15/991,906, filed May 29, 2018, which is a continuation of U.S. patent application Ser. No. 14/096,822, filed Dec. 4, 2013 and claims all benefit, including priority, of U.S. Provisional Patent Application Ser. No. 61/733,223, filed Dec. 4, 2012, entitled SYSTEM AND METHOD FOR ENHANCING CONTENT USING BRAIN-STATE DATA, the entire contents of each which is incorporated herein by this reference.

FIELD OF THE INVENTION

The present invention relates to bio-signal collection methods, and systems that utilize bio-signal data. This invention relates more particularly to visualization tools and methods.

BACKGROUND OF THE INVENTION

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns, which may be measured or monitored using an electroencephalogram (EEG). These electrical patterns, or brainwaves, are measurable by devices such as and EEG. Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces (BCI) have been developed that allow users to control devices and computers using brainwave signals.

Various platforms exist for creating or capturing content; and communicating this content either to the creator or the creator's audience.

There is a need to improve the evocative nature or engaging nature of communication platforms and methods.

SUMMARY OF THE INVENTION

A computer system or method may be provided for modulating content based on a person's brainwave data. The content may also be modulated based on a set of rules maintained by or accessible to the computer system. The content may also be modulated based on user input, including through receipt of a presentation control command that may be processed by the computer system of the present invention to modify presentation of content.

In accordance with an aspect of the present invention, there is provided a system comprising: at least one computing device; at least one biological-signal (bio-signal) sensor in communication with the at least one computing device; at least one user input device in communication with the at least one computing device; the at least one computing device configured to: present digital content at the at least one computing device for presentation to at least one user; receive bio-signal data of the at least one user from the at least one bio-signal sensor, at least one of the at least one bio-signal sensor comprising a brainwave sensor, and the received bio-signal data comprising at least brainwave data of the at least one user; and modify presentation of the digital content at the at least one computing device based at least partly on the received bio-signal data, at least one presentation modification rule associated with the presented digital content, and at least one presentation control command received from the at least one user input device. The presentation modification rule may be derived from a profile which can exist locally on the at least one computing device or on a remote computer server or servers, which may co-operate to implement a cloud platform. The profile may be user-specific. The user profile may include historical bio-signal data, analyzed and classified bio-signal data, and user demographic information and preferences. Accordingly, the user profile may represent or comprise a bio-signal interaction classification profile.

The digital content presentation may be audio, video, or any other type of physical, tactile, or any other type of presentation. Modification of the presentation of the digital content may include changing a sound or appearance of the content, adding other content to the presentation, associating brain state data with the presentation, or sharing the content with one or more other users, optionally through a separate content sharing service, network, or computer system.

The presentation modifying may include prioritizing, sorting, or filtering content, or any other types of presentation modification. The presentation modifying may be destructive or non-destructive to the original digital content.

The presentation modifying may include controlling operation of at least one application at the user's local computing device or on another computing device in communication therewith. For example, an application that may be controlled may include a video recorder application to start recording when a particular brain state or emotion threshold is achieved.

The digital content presented may include live audio or video content.

The received bio-signal data may comprise time-coded bio-signal data, and the digital content presentation may comprise time-coded presentation data. The at least one computing device may be configured to synchronize the time-coded bio-signal data to the time-coded presentation data at least partly by synchronizing time stamps between the time-coded bio-signal data and the time-coded presentation data, wherein the time-coded presentation data may be used by the at least one computing device to determine at least one presentation state of the presented digital content at a respective time stamp.

The at least one presentation control command may indicate a target brain state, and the presentation modification may comprise presenting digital content that is associated with the target brain state at the at least one computing device. Accordingly, the present invention may provide for modulating content to encourage a user to achieve a particular user-selected target brain state. At least one of the presentation modification rules may be associated with achieving the particular target brain state and may also be applied to determine a digital content presentation modification. The presentation modification may also include presenting positive feedback to reinforce or encourage a user to achieve or maintain a particular brain state. The presentation modification may also include presenting negative feedback to discourage a user from remaining in a non-target brain state (e.g. play a punishment sound).

Information gathered from bio-signal sensor data and presentation control command input can be used by the system to update presentation modification rules based on the content, goals, user profile, and activity of the user.

In accordance with an aspect of the present invention, there is provided a system comprising: at least one computing device; at least one bio-signal sensor in communication with the at least one computing device; at least one user input device in communication with the at least one computing device; the at least one computing device configured to: present digital content at the at least one computing device for presentation to at least one user; receive bio-signal data of the at least one user from the at least one bio-signal sensor, at least one of the at least one bio-signal sensor comprising a brainwave sensor, and the received bio-signal data comprising at least brainwave data of the at least one user; determine at least one brain state of the user in response to the presented digital content, the brain state determining based at least partly on received bio-signal data; and associate the determined brain state with the presented digital content. The presentation modification of the digital may be based at least partly on the at least one determined brain state and at least one presentation modification rule associated with the presented digital content. Accordingly, a user's brain state, or determined emotion, may be associated with the presented digital content. The digital content and associated brain state data may be shared to a content sharing service, such as Facebook or Youtube. The associated brain state may also be presented in some form with the digital content.

The system may include a content analyzer component which may determine features of the presented digital content through analysis. A determined content feature may be correlated via timestamp to a determined user brain state. For example, the content analyzer may determine that there is an advertisement playing and change the way the content is analyzed.

The system may include a content recommendation engine component which may use brain state data and analysis from the content analyzer component of content to make better recommendations. For example, the content analyzer may determine that the user has strong positive reactions to fight scenes in movies. The content recommendation engine may extrapolate from this determination to recommend another particular movie featuring fight scenes to the user.

In accordance with another aspect of the present invention, the at least one computing device may be configured to receive communication content during a communication session established over a communications network with at least one remote computing device; wherein the digital content presenting comprises presenting the received communication content at the at least one computing device for presentation to at least one user; and the determined brain state associating comprises associating the determined brain state with the received communication content. Accordingly, one or more users' respective brain state(s) may be tracked in a chat or other communication session. The at least one computing device may be configured to transmit the brain state associated with the received communication content to the at least one remote computing device over the communications network. In another aspect of the present invention, users of a social media or other communication service may be matched to one another based at least partly on similarities identified by the present invention in the respective users' brain states.

In accordance with another aspect of the present invention, the at least one computing device may be configured to modify presentation of the digital content at the at least one client computing device based at least partly on the at least one determined brain state and at least one presentation modification rule associated with the presented digital content. Accordingly, the present invention may provide for modulating content (either the communication content or other digital content) by the brain state of the user at the computing device.

In accordance with another aspect of the present invention, the at least one computing device may be configured to modify presentation of the digital content at the at least one client computing device based at least partly on the at least one received brain state and at least one presentation modification rule associated with the presented digital content. Accordingly, the present invention may provide for modulating content at the computing device based on the brain state of the remote user participating in the chat or other communication session.

In accordance with an aspect of the present invention, there is provided a system comprising: at least one computing device; at least one bio-signal sensor in communication with the at least one computing device; the at least one computing device configured to: receive bio-signal data of at least one user from the at least one bio-signal sensor, at least one of the at least one bio-signal sensor comprising a brainwave sensor, and the received bio-signal data comprising at least brainwave data of the at least one user; determine at least one brain state of the user, the brain state determining based at least partly on received bio-signal data; and select digital content for presentation to the at least one user based on the determined at least one brain state of the user; present the selected digital content at the at least one computing device. Accordingly, the present invention may provide for presenting digital content (e.g. advertisement content) to a user when the user is in a particular brain state (e.g. happiness).

In accordance with an aspect of the present invention, there is provided a system comprising: at least one computing device; at least one bio-signal sensor in communication with the at least one computing device; at least one user input device in communication with the at least one computing device; the at least one computing device configured to: receive bio-signal data of at least one user from the at least one bio-signal sensor, at least one of the at least one bio-signal sensor comprising a brainwave sensor, and the received bio-signal data comprising at least time-coded brainwave data of the at least one user, determine at least one brain state of the user, the brain state determining based at least partly on received bio-signal data, the determined at least one brain state comprising time-coded brain state data; recording time-coded user activity data representing at least one user interaction with the at least one computing device; synchronize the time-coded brain state data to the time-coded user activity data at least partly by synchronizing time stamps between the time-coded brain state data and the time-coded user activity data; and determine the brain state of the at least one user at a respective time stamp of the respective user interaction based at least partly on the time-coded user activity data. Accordingly, the present invention may provide for analyzing content creation (including brain state data) to generate content creation attributes (including identifying stages of content creation by time stamps and determining corresponding brain state(s) at those time stamps).

In accordance with an aspect of the present invention, the at least one user interaction may comprise at least one content creation activity by the user, and the recorded time-coded user activity data represents the status of the at least one content creation activity at respective time stamps.

In accordance with an aspect of the present invention, the at least one computing device may be configured to modify presentation of digital content associated with the at least one user interaction based at least partly on a correspondence between the time-coded brain state data at at least one time stamp with the time-coded user activity data at the at least one time stamp. Accordingly, the present invention may provide for modulating presentation of the user-created content based at least partly on the user's brain state when creating the content. Instances of the user-created content associated with particular time stamp(s) may be modulated based on application of presentation modification rules, user-inputted presentation control commands, and based on the user's brain state data corresponding to the same time stamp(s).

In accordance with an aspect of the present invention, a target brain state may be associated at the at least one computing device with encouraging at least one content creation activity, and wherein the modifying presentation of digital content comprises presenting digital content that is associated at the at least one computing device with the target brain state. Accordingly, the present invention may provide feedback to the user by way of modifying presentation of the digital content in order to encourage creativity or to encourage the user to achieve a particular brain state. The feedback presented may indicate how close or how far the user is from achieving the target brain state, and may also include recommended actions the user may perform in order to try to achieve the target brain state.

In accordance with an aspect of the present invention, the system may comprise at least one user input device in communication with the at least one computing device; and the target brain state may be based at least partly on at least one presentation control command received from the at least one user input device.

In accordance with an aspect of the present invention, the system may present a stimulus like a ping that is time stamped and analyzed to determine a corresponding evoked response in the user's brain state. The correlation may be performed up to about 2000 ms after presentation of the stimulus. Accordingly, the system may be calibrated to better analyze the user's particular brain waves.

In accordance with an aspect of the present invention, the system may synchronize brain state measurements of the user to the content of a second user. For example, a second user may also be watching the same television show as the first user and a comparison of brain waves may show that both are sharing a similar experience. The presentation modifying of the present invention may provide real-time presentations of the brain state data of both users, in a chart, graph, icon, or other indicator. A stream of the content being consumed by the users may also be modulated in some way based on the respective users' brain state data or based on any determined correspondences between the respective users' brain state data.

In accordance with an aspect of the present invention, a computer network implemented system enhancing content created using a communication utility is provided, the system comprising: a biofeedback computer system linked to a bio-signal processing system for capturing and analyzing bio-signal data so as to extract one or more state of mind features related to at least one individual interacting with the biofeedback computer system; wherein the biofeedback computer system is configured to extract the state of mind features continuously and relate these to creation of the content; and a content enhancement computer system which when executed: accesses one or more enhancement parameters for enhancing the content; processes the state of mind features; applies one or more applicable display rules; generates and makes available enhancements to the content based on the state of mind features.

A computer system implemented method is provided comprising:
 (a) providing a biofeedback computer system linked to a bio-signal processing system for capturing and analyzing bio-signal data so as to extract one or more state of mind features related to at least one individual;
 (b) linking the biofeedback computer system to a content generator such that state of mind features are continuously related to the creation of the content;
 (c) accessing one or more enhancement parameters for enhancing the content; and
 (d) processing the state of mind features and applying one or more applicable display rules so as to generate and makes available enhancements to the content based on the state of mind features, using a user interface linked to the content processor.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

Embodiments will now be described, by way of example only, with reference to the attached figures, wherein:

FIG. 26 shows an implementation of an aspect of the present invention, where a border of a video window is modulated;

FIG. 27 shows an implementation of an aspect of the present invention, where the user's current brain state may be communicated to the user;

FIG. 44 shows a list of callers waiting in a call queue together with each caller's associated brain state, in accordance with an aspect of the present invention;

Figure 1:
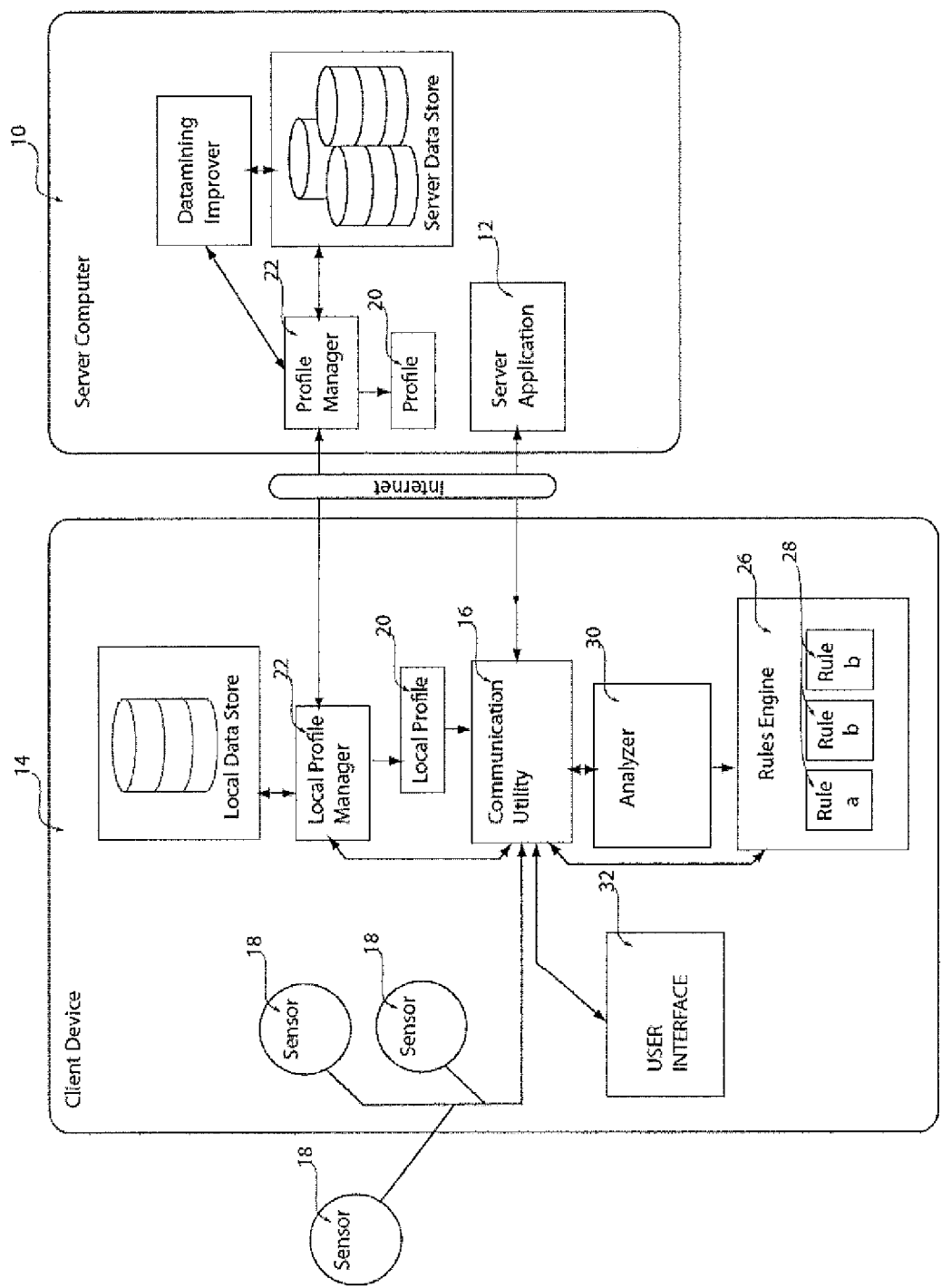
FIG. 1 illustrates an embodiment of the platform, including a possible cloud service model.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

The present invention consists of a computer implemented method, and a computer system that uses brain-state data in order to enhance the expression conveyed using a communication utility. The communication utility may consist any manner of utility, program, system, tool, or platform that enables communication of information in any medium. Communication utility may include for example a word processing utility, note taking utility, journaling application, audio or video player, an email application, an instant messaging application, note taking application, an audio recorder, video recorder, a drawing application, a social networking platform, and a variety of other applications that enable one or more users to record their thoughts, ideas or expressions ("expression"). The communication utility may generate or access content. The communication utility may also be referred to as a content processor or a content generator.

Brain-state information may be used in this invention to derive information regarding the emotional state or mood of one or more users. While the present disclosure discusses brain-state information in particular to derive this information, other data may be used instead of or in addition to brain-state information, while utilizing the content enhancement features of the present invention.

The computer implemented method and computer system of the present invention enables the capture of brain-state data in conjunction with the use of the communication utility. In one aspect of the invention, the communication utility is linked to, or incorporates, a brain-state data capture system for logging brain-state data in a way that may be synchronized with the communication utility such that the one or more user's brain-state data is associated with the expression stored using the communication utility. In one aspect of the invention, the brain-state data is captured continuously, and in real time.

In another aspect of the invention, the brain-state data capture system includes or embodies a series of rules for converting particular brain-state data into enhancements of the expressions, also referred to as "embellishment" in the present disclosure. These enhancements serve a variety of purposes, and these may depend on the particular type of communication utility, and also on its user.

For example, the embellishment of expression, using the present invention may: (a) enable a user to record their emotional context in connection with their expression; (b) to help the user, or the user's audience to comprehend the state of mind that was associated with a particular communication; (c) create content that is more engaging; (d) create content that holds deeper emotive meaning; and (e) create content that provokes recollection of other information associated with the content, based on the fact that people are visual and the linking of visual enhancements linked to state of mind is likely to encode the content in a way that permits the user to access memories associated with the content. In other words, the present information may permits users to encode content with a broader range of memories, and enable these memories to be more readily recollected at some point in the future.

Other implications of the embellishments of the present invention are discussed below.

In another aspect of the invention, the computer system of the present invention also includes an analyzer that analyzes the expression so as to interpret the expression for enabling the embellishment to be made in a coherent way, and in a way that extends the meaning carried by the impression. The analyzer permits the generation of embellishments that truly enhance the content. In one implementation of the analyzer, the analyzer (a) accesses the brain-state data, (b) analyzes the brain-state data, (c) maps the brain-state data into one or more of a plurality of moods or emotional states.

In one aspect of the invention, the brain-state data is captured continuously and mapped to the creation of the content so as to generate over a period of time one or more moods or emotional states, in that the moods or emotional states may vary over the period of time.

Figure 4:
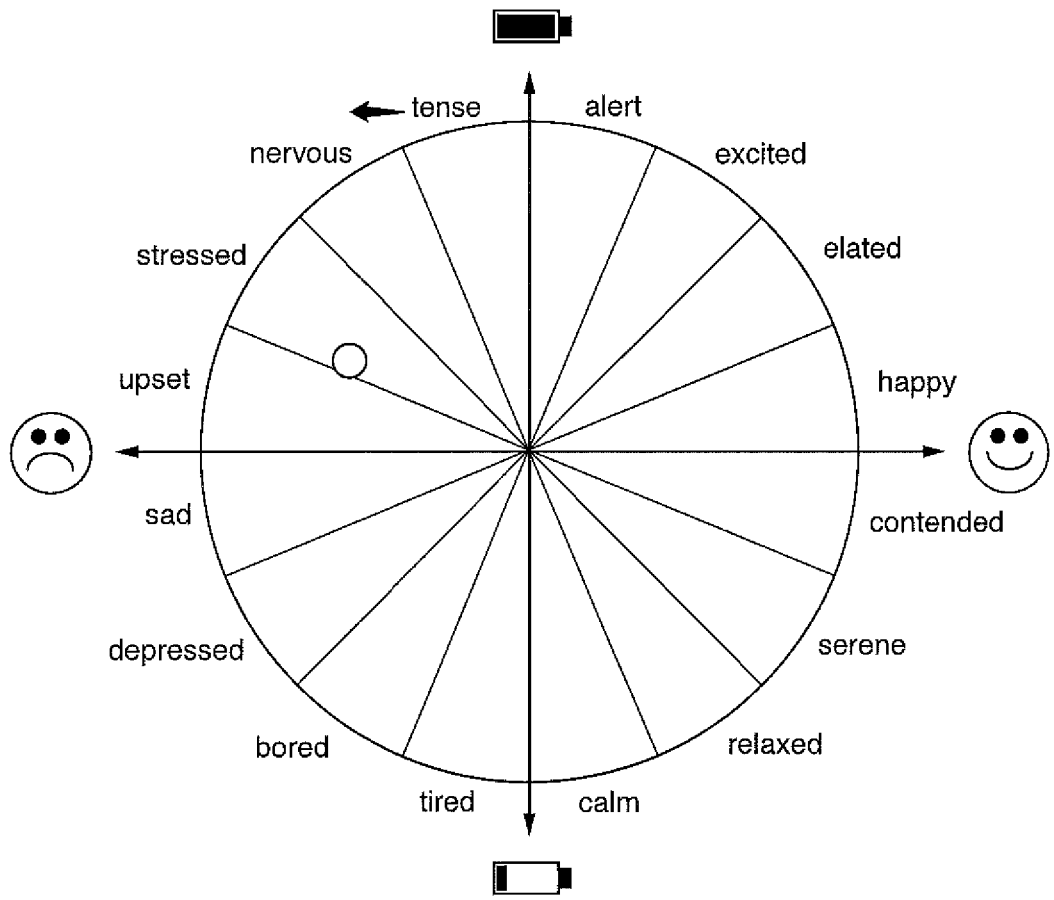
FIG. 4 shows a possible implementation of a mood chart in accordance with the present invention.
Figure 5:
FIG. 5 illustrates a tag cloud modulated by the present invention.

FIG. 4 illustrates a possible set of emotional states to which the analyzer may map brain-state data for a particular user, this case positive vs. negative, lethargic vs. high energy. Various other moods or emotional states are possible such as happy, sad or bored.

In another aspect of the invention, a user interface is linked to the communication utility, and is configured to allow access to the content in a form that is embellished using the present invention.

In one implementation, the user interface modifies the content based on the moods using a set of display rules that are evocative of the different moods or emotional states. The display rules may be generated by a user, or may be established by the system. The display rules may consist of a variety of different rules for encoding state of mind information into content.

Figures 2, 3:
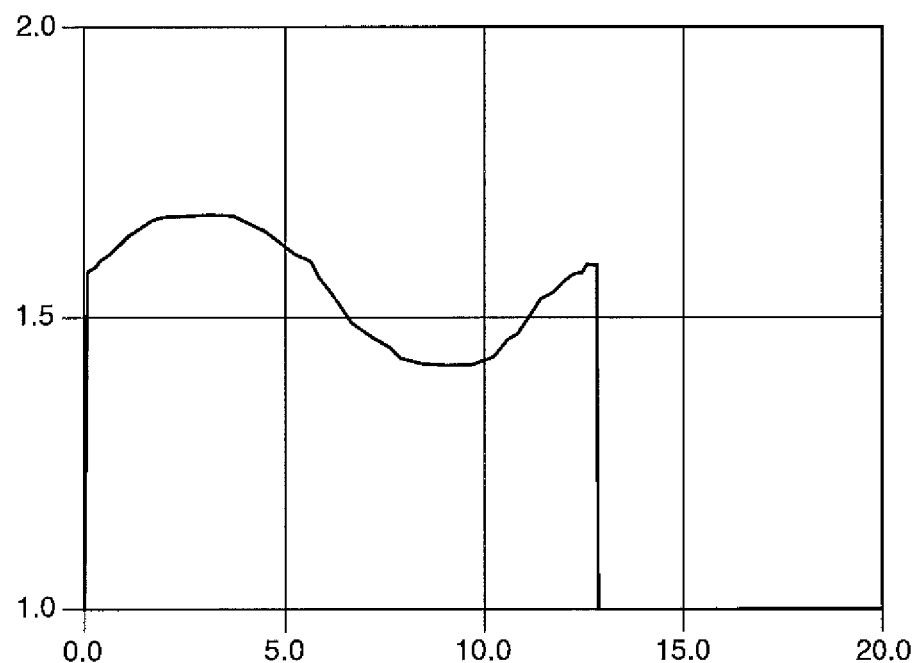
FIG. 2 illustrates a possible output of the present invention, where font of text is varied based on brain state information.
FIG. 3 shows a graph that illustrates variation of brain-state information.

For example, the display rules when executed may adapt content using brain-state data in the following ways: by (1) modifying font size of text as shown in FIG. 2; (2) modifying the fonts used in text where certain fonts are understood to indicate different moods; or (3) modifying line weight. Further details regarding possible display rules are set out below.

Brain-state information may be most evocative if linked to the time of creation of the content, however, there could be a separation between time of creation and brain-state information. For example, an application may be used to generate content, and then an "enhancement mode" may be triggered where a user may consume the content (read, listen to or view the content for example) and then encode the content with brain-state based enhancement based on the present invention. This separation of time of creation and brain-state based encoding may be desirable where the creation of the content does not occur in real time or near real time for example because content is created iteratively (for example because the creative process is iterative because of the need for editing for example) and therefore generation of emotional context using brain-state information may not result in meaningful emotional context to the content.

The computer implemented method and computer system of the present invention enables the capture of brain-state data in conjunction with the use of the communication utility. In one aspect of the invention, the communication utility is linked to, or incorporates, a brain-state data capture system for logging brain-state data in a way that may be synchronized with the communication utility such that the one or more user's brain-state data is associated with the expression stored using the communication utility. In one aspect of the invention, the brain-state data is captured continuously, and in real time.

In another aspect of the invention, the brain-state data capture system includes or embodies a series of rules for converting particular brain-state data into enhancements of the expressions, or embellishing the expressions. These enhancements serve a variety of purposes, and these may depend on the particular type of communication utility, and also on its user.

As previously stated, the embellishment of expression, using the present invention may: (1) enable a user to record their emotional context in connection with their expression; (2) to help the user, or the user's audience comprehend the state of mind that was associated with a particular communication; (3) create content that is more engaging; (4) create content that holds deeper emotive meaning. Other implications of the embellishments of the present invention are discussed below.

FIG. 4 illustrates a possible set of emotional states to which the analyzer may map brain-state data for a particular user. For example, the emotional states may include whether a user is happy, sad, bored. The moods generally may be "positive" or "negative".

In another aspect of the invention, a user interface is linked to the communication utility, and is configured to allow access to the content in a form that is embellished using the present invention.

In one implementation, the user interface modifies the content based on the moods using a set of display rules that are evocative of the different moods or emotional states.

The present invention helps people remember things by creating content that is more layered and evocative based on encoding of mood or state of mind information. This helps users remember context either at the time of creation, or afterwards when the embellished content is retrieved.

Computer System

FIG. 1 illustrates one possible computer system embodiment of the present invention. In the particular embodiment shown, the analyzer and rules engine referred to below are implemented on the client side.

In the embodiment shown, a server computer (10) is connected to the Internet. The server computer (10) may be implemented as a server farm. The server computer (10) may be linked to a server application (12) of the present invention. The server application (12) may be implemented an application repository. The computer system may also be implemented as a cloud computing service.

The server computer (10) may be linked to one or more client devices (14). A communication utility (16) may be linked to the client device (14). The communication utility (16) also be may be an Internet implemented platform accessed using the client device (14). In addition, one or more sensors (18) may be associated with a user for capture brain-state information, or information relevant to brain-state. The communication utility (16) may include, or be linked to, functionality that correlates sensor data to particular content, which may be important for example for applications where brain-state information is captured continuously in order to permit enhancement of content in conjunction with its creation.

In the implementation shown in FIG. 1, the computer system incorporates a brain-state profile system (20) implemented to the server application. The brain-state profile system (20) may be implemented similar to the one described in PCT Patent Application No. PCT/CA2013/000785, the entirety of which is incorporated herein by reference. A profile manager (22) may capture over time a profile (24) that includes one or more attributes for best capturing the mood of a particular user. The profile may also include one or more preferences of the particular user for embellishing their content. Each person's brainwaves are different, therefore requiring slightly different tunings for each user. Also, people learn to control their brain-state over time, and therefore parameters relevant for creating brain-state profile may change over time. New parameters can be calculated based on collected data, and can form part of a user's dynamic profile, by operation of the profile manager.

The computer system may also include a rules engine (26) that includes a series of rules (28) to convert brain-state information into content enhancements. The rules engine (26) may be adapted to apply different rules: (a) depending on the user, and their profile; (b) the communication utility (16); (c) preferred mechanisms to enhance content associated with (b), based on (a). Various additional mechanisms may be used to enhance content.

The rules engine (26) may be linked to an analyzer (30), which may be implemented as an analytics engine. The analyzer (30) may be executable to analyze the content linked to the communication utility (16) as described previously. The analyzer (30) may include or link to various content analysis tools, such as a semantic analyzer or a sentiment analyzer, so as to interpret the meaning of the content to be enhanced. This can assist in the intuitive contextualization of the content using the modulated brain-state information.

For example, PCT Patent Application No. PCT/CA2013/000785 suggests a possible mechanism for modulation of signal information, namely signal modulation, as well as correction of the modulation through "human-in-the loop" feedback control, which yields an error signal that may be used to optimize the bio-state estimation, data collection and then a application of a parameter adaptation method. For example, a maximum likelihood estimator of parameter values based on error signal.

The communication utility (16) can be linked to a user interface (32) which is adapted to enhance content based on brain-state information, as explained in this disclosure. The user interface (32) may be implemented in the cloud as part of the computer system shown in FIG. 1, where the user interface (32) connects for example with a communication utility (16) that may be installed on a client device (14), in order to provision user interface enhancements to the communication utility (16). The communication utility (16) may also be implemented as an Internet utility, and may link to the server computer (10) so as to access content enhancing functionality of the present invention. A communication utility (16) may implement one or more features of the present invention. Various computer network architectures may also be possible for implementing the present invention.

The computer system may be linked to sensor device (18) in a variety of ways. For example, a Multi-modal EEG Data-Collection and Adaptive Signal Processing System ("MED-CASP System") for enabling single or multi-user mobile brainwave applications may be provided. The MED-CASP System can be a cross platform mobile EEG platform specifically for enabling BCI applications that may be adapted to provide the enhancements described in this disclosure. The MED-CASP system platform may be implemented as a hardware and software solution that is comprised of an EEG headset, a client side application and a cloud service component. The client side application may be operating on a mobile or desktop computing device.

A particular MED-CASP system implementation may include a range of different features and functions, for example an EEG headset may be designed to target the meditation (such as health and wellness, or human-performance) market segment, and may be designed to be usable with other BCI applications. Non-limiting features of this headset may include: an unobtrusive soft-band headset that can be confidently worn in public; and differentiation from prior art consumer EEG solutions through the use of 3, or 4, or more electrodes (rather than one or two). This advancement may enable: estimation of hemispheric asymmetries and thus facilitate measurements of emotional valence (e.g. positive vs. negative emotions); and better signal-to-noise ratio (SNR) for global measurements and thus improved access to high-beta and gamma bands, fast oscillation EEG signals, which may be particularly important for analyzing cognitive tasks such as memory, learning, and perception. It has also been found that gamma bands are an important neural correlate of mediation expertise.

In the same or another non-limiting exemplary implementation, possible MED-CASP system features may include: uploading brainwaves and associated sensor and application state data to the cloud from mobile application; downloading brainwave & associated data from the cloud; real-time brain-state classification to enable BCI in games or other applications; transmitting real-time brain-state data to other users when playing a game to enable multi-user games; sharing brainwave data with other users to enable asynchronous comparisons of results; sharing brainwave data to other organizations or third party applications and systems; and support of cloud based user profiles for storing personal information, settings and pipeline parameters that have been tuned to optimize a specific user's experience. In this way, usage of the system platform can be device independent.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience). The core functionality of the MED-CASP system may be wrapped as an externally-usable library and API so that another developer may use the platform's features in the developer's application(s). The library may be a static library and API for Unity3D, iOS, Android, OSX, Windows, or any other operating system platform. The system platform may also be configured to use a pre-compiled algorithm supplied by a third party within the library, including the ability for a third party developer using the library, to use the developer's own algorithms with the library. The system platform may also support headsets from a variety of vendors; personal data security through encryption; and sharing of un-curated data (optionally using time-limited and fidelity limited access) though the sharing of encryption keys.

Various implementations of the MED-CASP system platform are possible. In particular, various different applications may be developed that utilize the system platform and enable different types of biofeedback systems.

For example the computer system of the present invention may be implemented as a hardware and software solution that is comprised of an EEG headset, a client side (mobile or PC based) application and a cloud service component. Various other implementations are possible.

In one implementation, the computer system of the present invention, which may include the MED-CASP system may when executed: (a) receive and log brainwave & associated sensor data ("brain-state information"), and application state data to the cloud; (b) modulate presentation of digital content; (c) optionally, associated profile attributes or preferences are accessed or retrieved; (d) attributes for enhancing content associated with a communication utility are constructed ("enhancement attributes"); and (e) the enhancement attributes are executed by a communication utility so as to generate content that is enhanced using brain-state information.

The brain-state data capture system (20), linked to the analyzer, when executed establishes in real time or near real time the mood for a particular user.

Various different display rules may be used to provide a range of content enhancing features.

Figure 6:
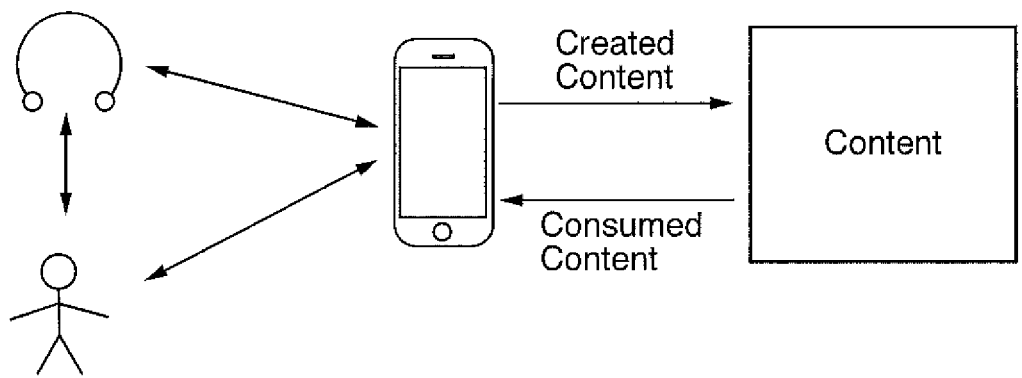
FIG. 6 shows a use case scenario of brain state information.

FIG. 6 illustrates a non-limiting exemplary use case scenario in accordance with aspects of the present invention. The computer system may determine and record one or more emotions associated with a user's measured brain state information. Possible benefits of recording a user's motion may include: obtaining insight into the user's interest in the content being viewed or created by the user; allow a user viewing content to receive information about the state-of-mind of the creator of the content; to create or fine-tune content to be more engaging to a viewing user, to be more thought provoking to a viewing user, or to be more easily remembered by a viewing user.

Figure 7:
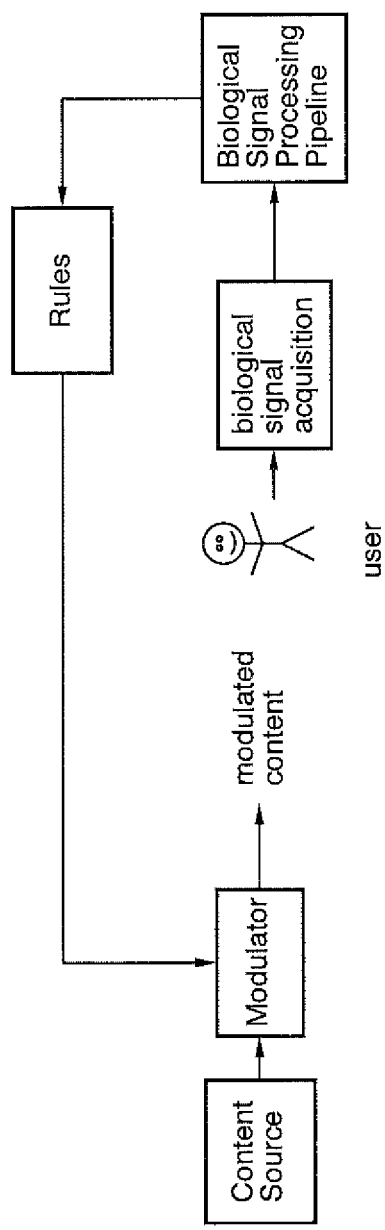
FIG. 7 illustrates a system diagram view of an embodiment of the present invention.

Various embodiments or implementations of the system of the present invention are possible. The present invention may be applied to situations where a user is creating content, or where a user is viewing content. In either case, the content may be digital content that can be created, stored, and viewed on a computing device, such as a desktop computer, mobile phone, tablet computer, wearable computer, server computer, or across a network of computing devices. The present invention may be adapted to any type of computing device, and the use of the term "computing device" in the claims is not intended to be limited to any particular type of computing device. As shown in FIG. 7, a user's biological signal information may be acquired and processed by a biological signal processing pipeline of the computer system of the present invention. The biological signal processing pipeline may be defined as in PCT Patent Application No. PCT/CA2013/000785 and may apply preprocessing, feature extraction, and classification to the biological signal information.

The biological signal information, or bio-signal data, may be obtained from the user through the use of at least one bio-signal sensor in communication with at least one computing device (shown as biological signal acquisition in FIG. 7). The digital content may be provided from a content source, as shown. The digital content may include external content, and may include any one or more of audio, video, text, books, etc. In addition the content source could be biological signal data as well. The digital content could also be a separate application, such as Adobe Photoshop, or Microsoft Word, which may or may not be executing from the computing device at the user. Optionally, the application(s) or other digital content may reside on a separate computer or server, or cloud storage, accessible for viewing, interacting, or otherwise consuming or presenting to the user's computing device over a communications network.

The computing device which the user is using to view, create, or otherwise interact or interface with digital content may or may not necessarily be the same computing device that processes the bio-signal data. For example, the user's bio-signal data may be received by a local computer, then transmitted over a communications network, such as the Internet, other wide area network, or a local area network, to another computing device for processing. The at least one bio-signal sensor may include at least one brainwave sensor, such as an EEG sensor. Such a brainwave sensor may include at least a pair of electrodes positionable on the user to monitor the user's brainwave activity. The brainwave sensors may be included in a wearable headband as described in this patent application or in PCT Patent Application No. PCT/CA2013/000785. The computer system may process the bio-signal data using the biological signal processing pipeline shown in FIG. 7, in order to determine at least one brain state of the user. The brain state data may be determined to have occurred in response to user being presented with particular digital content. The computer system may therefore associate the user's determined brain state with the presented digital content.

Instead of, or in addition to, performing this association, the computer system may optionally modify presentation of the digital content at the at least one computing device based at least partly on the received bio-signal data and at least one presentation modification rule associated with the presented digital content. Application of any such rules may be applied as shown in FIG. 7 for processing by a modulator component interfacing with a content source, as shown.

Optionally, the computer system may be further configured to modify presentation of the digital content based at least partly on at least one presentation control command received from at least one user input device in communication with the at least one computing device. This may be represented by the "manual override" shown in FIGS. 8-12 which may feed into a modulation controller that controls operation of the modulator. The input device may be a keyboard, touchpad, touchscreen, speech input, mouse, or any other user input device. The user input device may communicate with the at least one computing device through wired or wireless communications, such as Bluetooth. All or some of the bio-signal sensor(s), user input device(s) and computing device(s) may be integrated into one wearable computing device or other computing device. Presenting digital content for presentation to the user, or modifying presentation of the digital content may include visual presentation (such as display on a display device connected to the computer system), audio presentation (such as playing sound or music on an audio device connected to the computer system, such as speakers or headphones), or any other type of presentation (e.g. through any type of presentation device or component, such as a tactile feedback device, such as a vibrating game controller or mobile phone). Modulating, or modifying presentation of the digital content, may include changing how the digital content appears or sounds, displaying or playing additional digital content. Changing appearance of the content may include scaling or moving elements of the digital content on a display, or modifying the opacity, contrast, or colour of particular elements of the digital content. The types of digital content to be displayed or modified is not limited to any particular content or modifications.

The modulation controller may include or be associated with a set of rules that are applied to a specific goal established by the user. The modulation controller may receive features or predictions from the signal processing pipeline and apply rules that modulate the digital content. In addition, optionally, only parts of the content may be modulated such as only the audio portion of video. Each time the content is modulated and presented, the user's response may be determined, and the content may be modified further in accordance with the rules. The modulation of the content therefore may therefore be iterative, including based on input from the user. The modification of presentation of the content may include various classes of modification, including: proportional, where there is an amplifier that multiplies the signal by some constant to increase its amplitude or frequency or some other feature; derivative, where the rate of change or acceleration of a feature is used to control the modulator (e.g. if heart rate increased by 20% then send calming audio to the user); and integral, where accumulation or summing up of features used to control the output (e.g. if a user is in a particular brain state for 30 seconds then apply a reward tone for neurofeedback).

The modulator may apply rules to the signal as input by the modulation controller to control media experienced by the user. For example, in the case of audio content, volume or equalizer settings, or other properties of the audio may be changed depending on the mood of the user. In the case of neurofeedback, the modulated content could be the speed of a character in a game.

Figure 8:
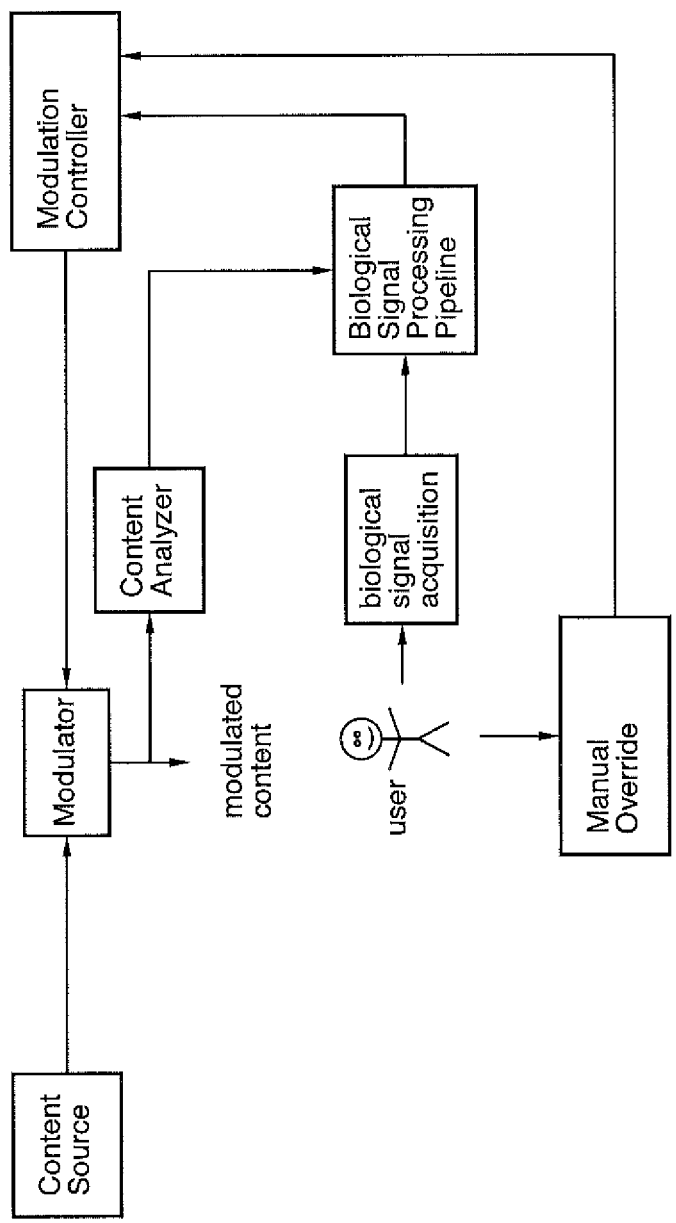
FIG. 8 illustrates a system diagram view of an embodiment of the present invention.

In a non-limiting example of the embodiment of the present invention shown in FIG. 8, the user may be listening to music such that the content source is music playing over a sound system that is being modulated by the modulator. The user's intention is to have background music that has a calming effect allowing the user to focus on a mental task and not have the music be a distraction. The music is being modulated by analyzing the user's brainwaves and re-modulating the music if the user's brainwaves indicate agitation or distraction. The user's brainwaves are analyzed to determine the user's level of calmness and focus through acquiring the user's EEG signals using "Biological Signal Acquisition". The EEG signals are then sent to the Biological Signal Processing Pipeline which may apply preprocessing, feature extraction, and classification. Preprocessing, feature extraction, and classification are described in more detail in PCT Patent Application No. PCT/CA2013/000785. The Modulation Controller may apply a set of rules to the goal of calm and focus. In this case the Modulation Controller takes into account: the brain state of the user as determined by the classifier, their mood goal, and activity. The Modulation Controller can take into account many other variables including: time of day, what music came before, what activity is to follow, what activity calm before, other biological measures etc. In addition, the Modulation Controller also takes into account user preferences as directly controlled by the user by entering commands in the manual override. The user may choose to increase volume of the music, skip a track change the equalizer settings for the music. Acoustic effects could be added based on brain state/emotion. The music may be modulated to adapt to the listener. The musician may passively express himself or herself by adding characteristics of the musician's brain state to the music. The music may become faster/slower, louder/softer, or accompaniments may be added in accordance with a particular musical composition generating algorithm. The music may therefore better express the performer's or composer's brain state.

Music may also be recommended based on brain state. For example, music may be recommended based on how a user's brain signature responds to certain kinds of music, and then match/correlate that to how the user would respond to music that has similar characteristics. A user may also tag music with a brain state or emotion experienced while creating or playing the music. The computer system may also be configured to intentionally modulate music or other audio content to assist the audience in paying attention to the audio content.

The preprocessing described above may include the computer system processing the bio-sensor data. This can involve, as non-limiting examples, interpolating gaps in signals, noise identification, noise filtering, spatial filtering, band-pass filtering. Other solutions may be employed for handling issues related to signal collection and transmission. Signal processing is a broad area that refers to mathematical methods of extracting or transforming signals. The goal is to pre-process the signal to remove unwanted noise and artifacts or to focus on a narrow frequency bands of interest.

Signal processing may include: filters (frequency response characteristics) (may include: low pass; high pass; and bandpass); order of filters; artifact detection method (common spatial patterns, Threshold (e.g. log bandpower, signal power), high frequency EMG with spatial patterns, off); artifact removal method (ICA, repair bursts, ignore sections with artifacts); resample rate; EEG channels to use; electrode referencing scheme (average reference, specific electrode, linked mastoids); data cleaning (remove flatlines, remove broken channels, remove spikes or bursts); baseline removal (off or on); and window definition (size and increment).

The feature extraction described above, may include using the preprocessed data to extract features from the signal. For example, this may be done through linear projection (such as Short-time Fourier transform, "STFT") of the EEG signal or non-linear functions (such as fractal dimension) of the EEG data. The resulting feature space may have greater or lesser dimensions than the original data. This projection may aid in the classification of the collected data, for example, by increasing the separability of classes. Examples feature methods used by the system (operating on original signal or features of the signal) may include: short time Fourier transform; wavelet; AR model coefficients (auto regressive model of the signal); Non-linear complexity features such as fractal dimensions (Hilbert transform); ensemble empirical mode decomposition; signal derivatives; and regularized covariance matrix estimation (such as ledoit wolfe estimator). Feature extraction is also a form of signal processing, however the goal may be to extract features that are useful for machine learning to build prediction models. Frequency domain signal processing may include: fast Fourier transform ("FFT"), wavelet or Hilbert; kernel definition (Hamming window, wavelet type); power spectrum; power per EEG band; power variance per EEG band; peak frequency within a particular band; and phase differences across electrodes within EEG frequency bands. Time domain signal processing may include: window sub-segments; voltage or signal power thresholds; and quantization or discretization thresholds to encode continuous feature value to discrete value. Transforming data to extract features may be accomplished at least by using principal components analysis, linear discriminant analysis, eigendecomposition, and/or whitening transformations.

In a non-limiting implementation of the present invention, the computer system may determine at least one brain state of the user, the brain state being determined based at least partly on received bio-signal data and select digital content for presentation to the at least one user based on the determined at least one brain state of the user. In this case, the computer system is not necessarily reliant upon digital content having already been displayed to the user. Rather, the computer system attempts to determine whether the user is in a particular brain state. If so, the computer system selects digital content for presentation to the user that is somehow associated with the determined brain state, and presents the selected digital content at the at least one computing device. For example, when a user is in a "happy" brain state, the computer system may present a particular advertisement to the user, as showing an advertisement to a happy user may be more effective than showing the same advertisement to an angry or distracted user. When a user is in a "distracted" brain state, the computer system may present a soothing presentation of content, either by modulating sound to be calming, or by reducing the number of items displayed to the user, or by any other content modulation or modifying method that is configured into the computer system.

In a non-limiting implementation of the present invention, the received bio-signal data may include at least time-coded brainwave data of the at least one user, and the determined at least one brain state may comprise time-coded brain state data. The computer system may be configured to record time-coded user activity data representing at least one user interaction with the at least one computing device, synchronize the time-coded brain state data to the time-coded user activity data at least partly by synchronizing time stamps between the time-coded brain state data and the time-coded user activity data, and determine the brain state of the at least one user at a respective time stamp of the respective user interaction based at least partly on the time-coded user activity data. In this way, the computer system of the present invention may determine and record what brain state(s) was exhibited by the user during particular interactions with the computer system. This may be applied to situations where the user is playing a video game, chatting with another user, creating content (e.g. writing text, drawing art, composing music, etc.), or consuming content. The computer system may then know what the user was feeling at any given time stamp, or moment, of the interaction. The recorded brain state information may be used to modulate or modify the display of digital content to the user or to other users of the same content. The user's brain state information may also be forwarded or displayed in some format to other users viewing or interacting with the same or similar content.

The computer system of the present invention may present at least a subset of the received bio-signal data to the user. For example, the computer system may modify presentation of the digital content by also presenting some of the bio-signal data or information derived therefrom. The computer system may determine what of the bio-signal data to display by analyzing the bio-signal data received. For example, the computer system may present a visual indication of a user's determined brain state on a display visible to the user or on a display visible to other users. The presentation modifying may include presenting at least one representation of the user's brain state based at least partly on the received bio-signal data and the at least one presentation modification rule. For example, a presentation modification rule may direct the computer system to enlarge the size of particular text elements displayed to the user upon determining that the user's brain state is indicative of a lack of focus. The presentation modifying may be further modified by at least one presentation control command being received from a user through an input device connected to or otherwise in communicating with the computer system or computing device. For example, the presentation control command may include a direction to the computer system to further increase the size of the text elements, or the presentation control command may include a direction to the computer system to revert the size of the text elements to the originally displayed size, and to cease to increase size of the text elements in the future.

In order to correlate received bio-signal data with the presented digital content, the computer system may be configured to associate time stamps to the presentation of the digital content at particular intervals, and also to the received bio-signal data. Accordingly, the received bio-signal data may include time-coded bio-signal data, and the digital content presentation may include time-coded presentation data. The computer system may synchronize the time-coded bio-signal data to the time-coded presentation data at least partly by synchronizing time stamps between the time-coded bio-signal data and the time-coded presentation data. In this way, the time-coded presentation data may be used to determine at least one presentation state of the presented digital content at a respective time stamp. The computer system may modify presentation of the digital content based on a correspondence between the time-coded bio-signal data at at least one time stamp with the time-coded presentation data at the at least one time stamp.

The time stamps may therefore be used to more precisely determine a user's bio-signal response to the presented digital content. For example, a particular instance in time in presentation of an advertisement to the user that caused the user to be happy or angry, could be determined. The portion of the advertisement causing the particular bio-signal response, could then be modified to either accentuate or remove the portion of the advertisement.

Figure 9:
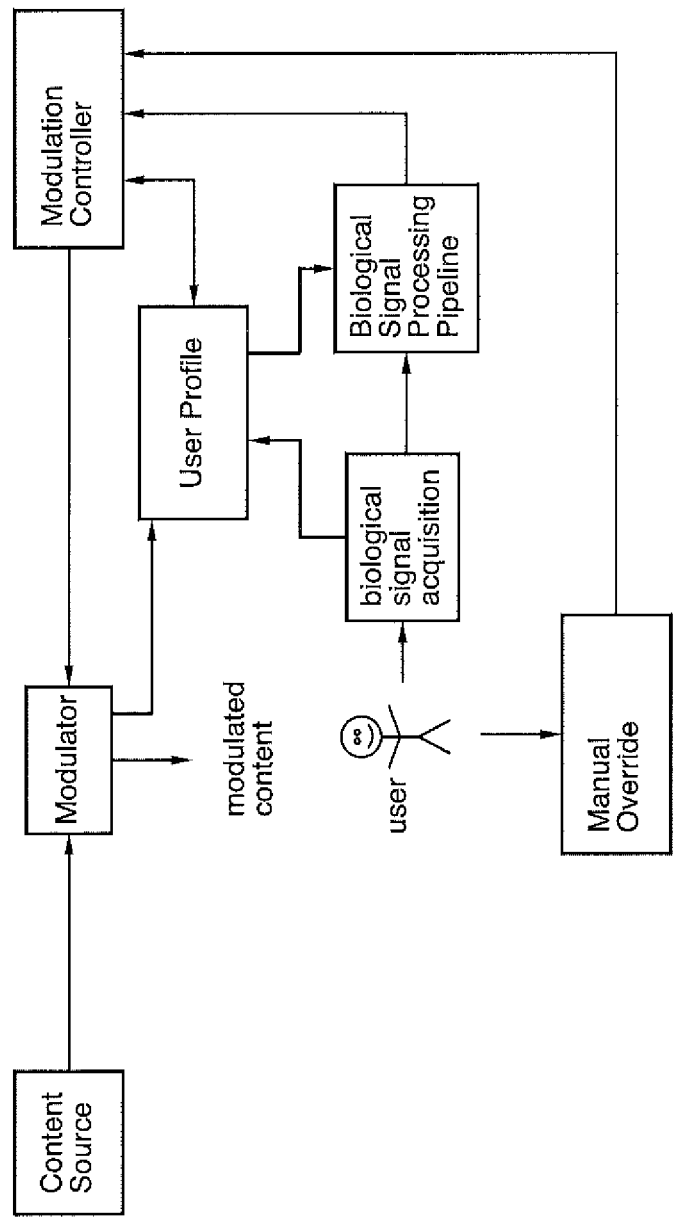
FIG. 9 illustrates a system diagram view of an embodiment of the present invention.

The computing device may store a bio-signal interaction classification profile (as shown in FIG. 9), or the computing device may communicate with one or more other computing devices in order to access information stored in such a profile. The profile may interface with the biological signal acquisition, the biological signal processing pipeline, the modulation controller, and the modulator. The bio-signal interaction classification profile may be user-specific or more generally applicable. The profile may include portions that are user-specific and portions that are not user-specific. Each profile may be associated with a particular user. The profile may include information on how to determine a particular brain state or emotion or the user experience the digital content presentation. The profile may include directions to the computer system on how to modify presentation of the digital content based on the received bio-signal data or the determined brain state or emotion of the user. The computer system may also include a data mining improver, which may interface with the profile, and may learn a user's preferences and change the rules in the Rules Engine (described in greater detail later) for achieving the user's goal.

For example, music may be modulated based on prior knowledge of what works for the user (e.g. what modulation produces particular brain state responses in the user) and is encoded as a set of rules. The rules can be learned from the user directly training the rules engine, or from other users as informed through the cloud. In this example, the user has selected effective working stimulation as their goal. The modulator controls the amount of spatial content that the audio has in order affect its pull on the user's awareness. Audio with higher spatial content may result in greater engagement in the user. Boundaries are set on the levels of calculated engagement by analyzing brainwaves that are optimal for the user. When the user crosses a boundary associated with too little engagement with the music (or too much engagement with the external environment), the spatial content is increased to increase engagement with the music. If the user becomes too engaged with the music and thereby working less effectively because the user is distracted by music, spatial content may be decreased. If the user adjusts the volume, the rules engine may interpret this as a possibility that the user requires a different level of engagement. For instance, two rules added to the Rules Engine may include: "Higher volume (than standard setting)=greater engagement with music"; and "Lower volume=lesser engagement of music". This is a simple example of modulation correction. This information can be used to update the boundaries in the rules engine. Different logics are possible for this update.

Figure 10:
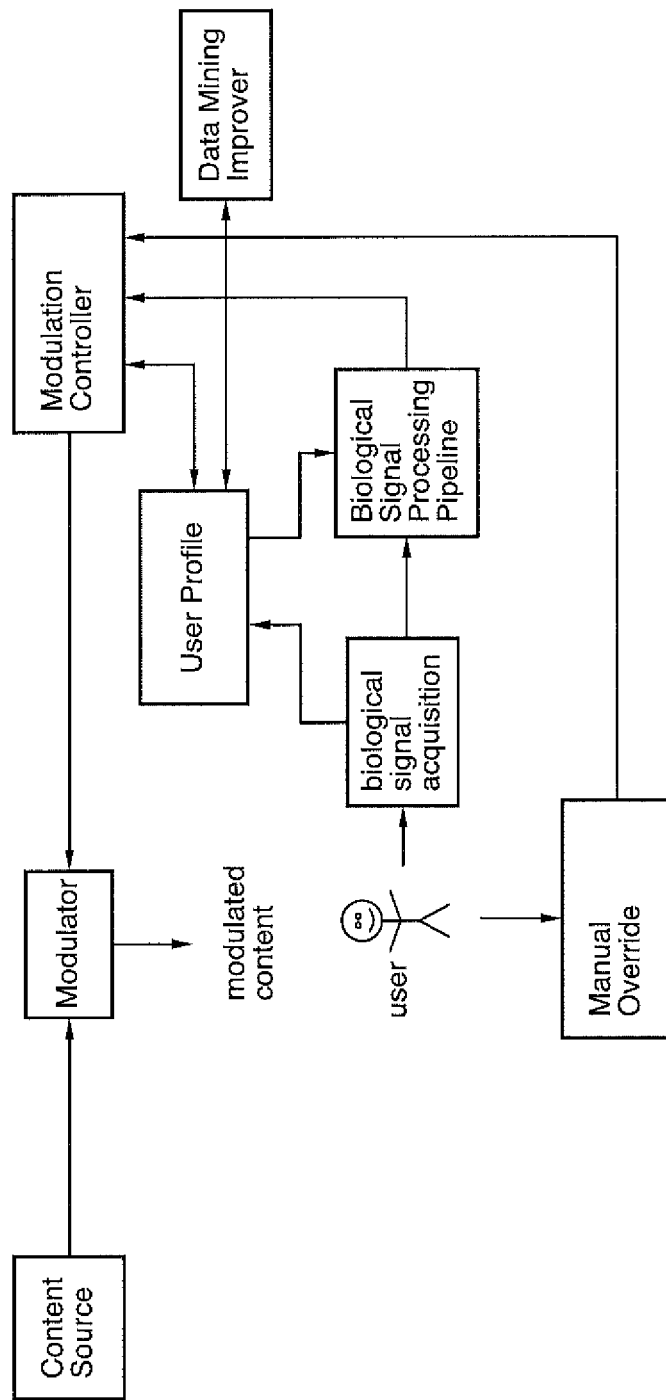
FIG. 10 illustrates a system diagram view of an embodiment of the present invention.
Figure 11:
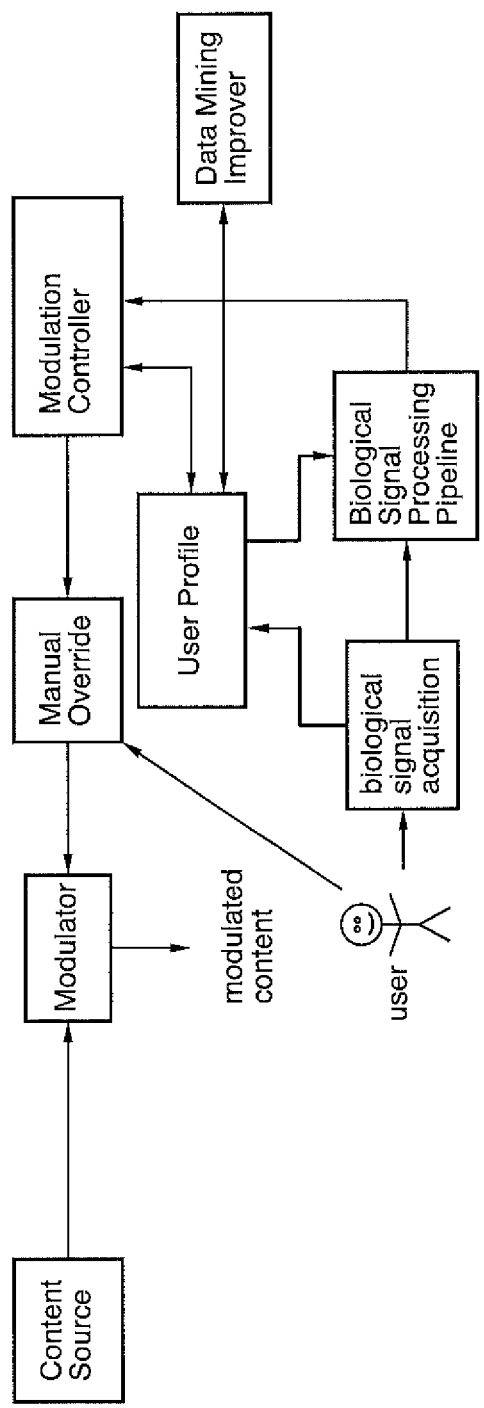
FIG. 11 illustrates a system diagram view of an embodiment of the present invention.
Figure 12:
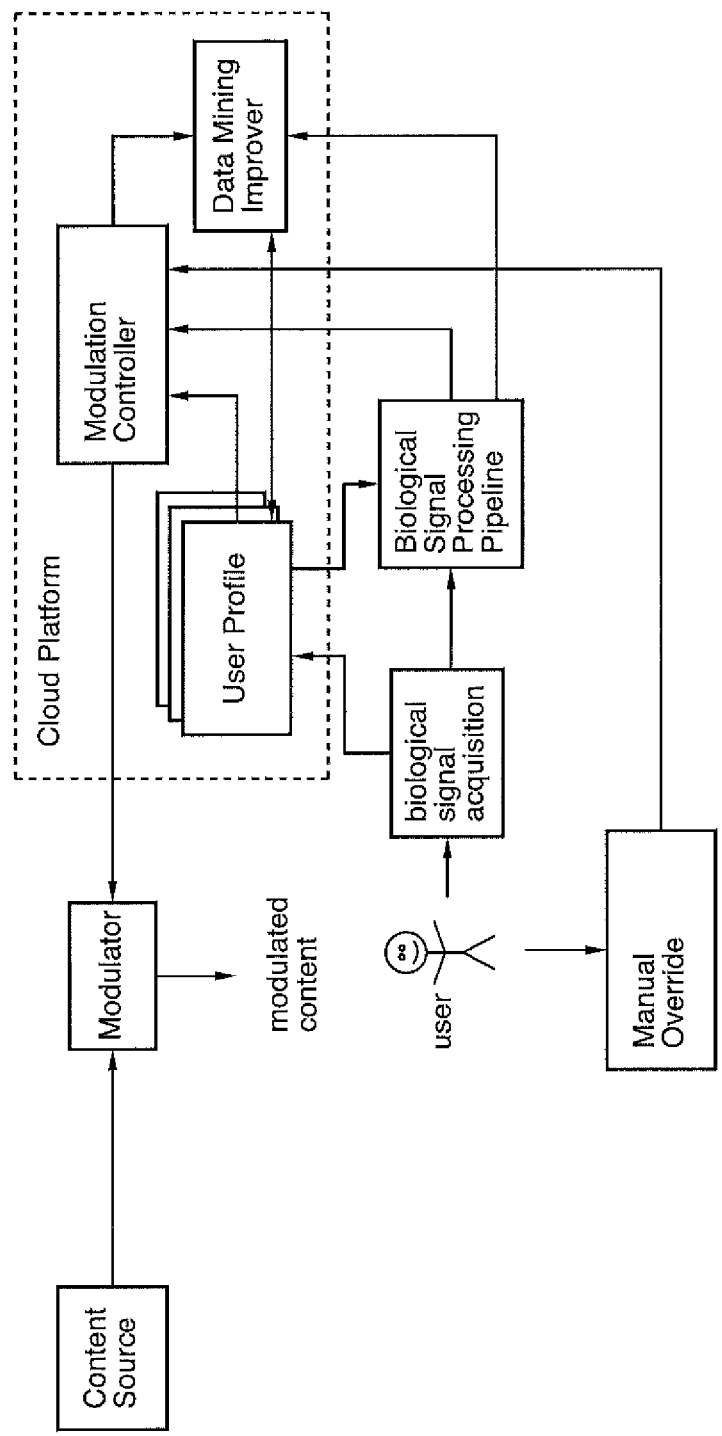
FIG. 12 illustrates a system diagram view of an embodiment of the present invention.

When the computer system receives a presentation control command input from the user, the computer system may override application of any presentation modification, and the computer system may further update the bio-signal interaction classification profile based at least partly on the presentation control command. For example, the user may instruct the computer system to perform or not perform a particular presentation modification, and the user may also instruct the computer system to maintain this instruction. The instruction may therefore be stored in the bio-signal interaction classification profile, which may be associated with the particular user that provided the presentation control command. The presentation control command input may be applied prior to any other presentation modifying (as shown in FIGS. 9 and 10), or the presentation control command input may be applied subsequent to other presentation modifying (as shown in FIG. 11).

The at least one computing device may be configured to update the bio-signal interaction classification profile based at least partly on bio-signal interaction classification data received from at least one computer server over a communications network. The at least one computing device may be configured to update the at least one presentation modification rule based at least partly on presentation modification rule data received from at least one computer server over a communications network. Accordingly, various aspects of the computer system may be stored remotely from the computing device of the user. In particular the profile and modulation controller may be stored on a computer server or servers, at a cloud platform, a shown in FIG. 12. The data mining improver may also be implemented in the cloud, as shown, and may interface with the biological signal processing engine and modulation controller.

The data mining improver may take advantage of looking across a plurality of user profiles to establish modulation controller rules, algorithms, etc. for demographics that are similar to the present user. Such established rules may then be applied to the present user and stored in the user's profile either in the cloud or on the local computing device.

The profile may have a data structure and function as described in PCT Patent Application No. PCT/CA2013/000785, and may store annotated raw biological data, algorithm settings, preferences and demographics of the user.

The at least one presentation control command may indicate a target brain state for the user to achieve. The presentation modification may include presenting digital content that is associated with the target brain state at the at least one computing device. Accordingly, if the user instructs the computer system that the user wishes to be in a relaxed brain state, or in a happy brain state, the computer system may modify presentation of the digital content in such a way that is associated with that targeted brain state, optionally to allow the user to achieve or maintain the targeted brain state.

The presentation modification may include updating an activity feed associated with the at least one user. For example, where the user is registered with Facebook, Twitter, or other social media service, the computer system may update the user's status or timeline, or make a posting on the service based at least partly on the received bio-signal data. The computer system may be provided with login access to the user's respective social media accounts. If the user is determined to be experiencing a particular brain state or emotion, the computer system may incorporate that information into a posting or other type of submission to a social media service. The submission may include information about the activity being performed by the user at the time the respective bio-signal data was received. Accordingly, the activity feed updating may include the at least one computing device transmitting at least one activity feed update command to at least one computer server to update an activity feed associated with the at least one user at the computer server.

Rules Engine (Modulation Controller)

The rules engine, or modulation controller, of the present invention, implemented by the computer system of the present invention may generate, store, update, or modify one or more presentation modification rules that are used by the computer system of the present invention to determine how to modify presentation of digital content to the user at at least one computing device of the system.

Figure 45:
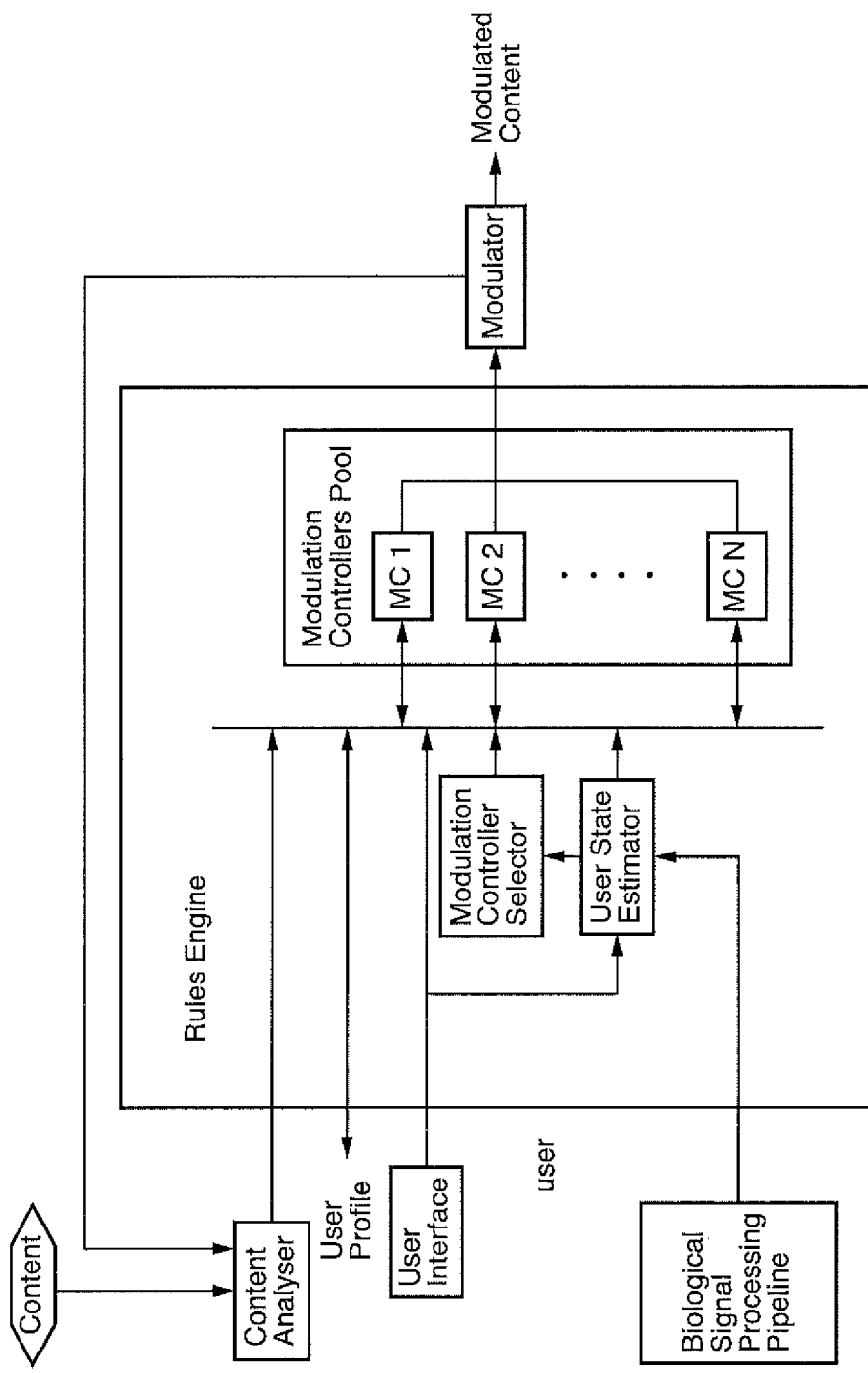
FIG. 45 illustrates a diagram view of a rules engine or modulation controller component in accordance with an aspect of the present invention.

The rules engine, an example architecture of which is shown in FIG. 45, may include a content analyzer component, which may be implemented in hardware or software. The content analyzer may determine events and characteristics of the content. The content analyzer may add labelled timestamps of those events that are synchronized with biological data. The content analyzer may be important as there are many existing technologies that can be applied, that are highly optimized and are available as software as a service or embeddable library (e.g. voice recognition). The content analyzer may be implemented using available content analysis techniques, such as more recent auto-encoder and deep learning methods, as well as commonly used feature and classifier methods.

Input to the content analyzer may include modulated content, and the content analyzer may also receive the original un-modulated content, or information from the modulator to improve the performance in situations where the modulation may introduce too much data corruption (e.g. captcha). For video salience, the content analyzer may receive information about how other users have reacted to the video, to assist in the estimation of what features the current user may react to. For application state information, the content analyzer may determine what to analyze based on the state of the application. For example, for a Youtube advertisement, different feature extraction may need to be used for the advertisement compared to the content the user is awaiting to view.

Input may also include information about the other user's state in the case of a synchronous multi user application (e.g. for online chat, where the emotional content is analyzed by a word analyzer that also considers the other user's available data streams, like level of distraction). The user's brain state may be determined to be distracted, and the user may inadvertently use strong language as a result of the user's attention being divided. By considering other available information, a better estimate of true message content may be produced.

Output from the content analyzer for text content, may include: language/semantic analysis for emotional content; document structural analysis; and user state estimation using offline and real-time keyboard entry dynamics.

Output from the content analyzer for video content, may include: scene change detection in video content (e.g. may use frame differencing methods, motion tracking estimates; may involve interest point detection/description including harris corners, canny edges, or more advanced method such as sift features); face detection, and emotion estimation based on facial expression; and interest point detection based on other user data (e.g. could be accessed from a content server, based on a user's profile).

Output from the content analyzer for audio content, may include: beat detection; musical scale detection; melody extraction; interest point detection based on other user data. (e.g. could be accessed from a content server, based on a user's profile); and voice recognition (e.g. word output, language processing).

The modulation controller ("MC") or rules engine may include a set of rules that map conditions, user state (e.g. brain state), and application state with a modulation output. A MC takes as input events and continuous data and creates signals to control the modulator. A MC is selected based on a presented user interface and user state estimator. A rule in the MC can take inputs from the user profile (e.g. age), type of content, user state estimate, selections from the User Interface including Manual Override, Goal, etc. The Output of the MC controls the Modulator. A modulation controller may be built to operate within a dataflow architecture, so that it can be embedded in the rules engine by an application or a user.

A non-limiting list of types of rules may include: discrete relations (e.g. decision trees; lookup tables; if/then); control laws/relationships (e.g. PID controller, threshold based events with hysteresis); method (e.g. reward based neurofeedback paradigms on normative user data); training systems (e.g. neurofeedback mindfulness protocols; state change methods including progressive stimulus with neurofeedback, and iterative relaxation/excitation state hopping); and stimulus based active state estimation (e.g. ERP based cognitive load monitoring; and ERSP based attention monitoring).

A modulation controller selector component may be provided, implemented in hardware or software that chooses a modulation controller, or set of rules, to apply to the content. The modulation controller selector may include a probability model, a local model update function, and a global model update function. The probability model may include a hierarchical bayes model, that allows for the estimation of what MC should be used given User inputs (e.g. User Goals, Activity, user state estimation, manual override, etc.), application state, and content features. The local model update function may update the probability model based on real-time user inputs, in particular based on the manual override (the presentation control command received from at least one user input device). The global model update function may use the data in the user profile (including recent data produced by the rules engine), and may typically run in the cloud because of the computational complexity. If the model is updated in the cloud, the updated model may be returned to the client device along with the local model update function.

A user estimator component may be provided that takes as input a combination of discrete variables and continuous variables. Its outputs may also be a combination of discrete variables and continuous variables. Output examples may include: mind wandering, thinking, sleeping, etc., as well as a related intensity.

A user interface ("UI") may be provided by the computer system of the present invention where the user may select or presented with a goal (e.g. to be happy, creative, focussed, calm, etc.). The UI may also indicate or allow the user to specify a preferred application to achieve the goal (e.g. meditation exercise). The UI may also provide an indication of or allow the user to specify a current activity performed by the user (e.g. doing homework, writing an email, using Facebook, etc.). The UI may also allow the user to self-report activities or events, and may provide a means for the user to override any application of rules or modification of presentation of the digital content through selection of or manual entry of a presentation control command.

The modulator component may be implemented in hardware or software and may modulate the digital content by changing audio, video, or text as directed by the modulation controller. Types of actions that a modulation controller can output to the modulator for implementation may include: proportional (e.g. this is an amplifier that multiplies the signal by some constant to increase its amplitude or frequency or some other feature; derivative (e.g. the rate of change or acceleration of a feature is used to control the modulator, for instance if heart rate increased by 20% then send calming audio to user); integral (e.g. accumulation or summing up of features used to control the output, for instance if a user is in a brain state for 30 seconds then apply a reward tone for neurofeedback); state machine (e.g. like a computer program); if-then-else (e.g. subset of state machine).

The user profile may be stored on the client computing device or a remote computing device, such as the cloud platform of the present invention. The user profile may use demographic and historical information as input and can be updated by a rule executing.

Rules for the rules engine may be pre-programmed in advance to provide general rules or a default set of rules for the computer system to apply. Rules may also come from third party developers or shared by users with other users, possibly over social media that share similar goals, interests, or demographics. Rules can be automatically discovered and updated. Rules may also come from experience a user has gained using other applications. For example, in a meditation application, the goal may be to achieve a quiet mind and focus. This can be transferred to rules that are for training and mood management to decrease distraction, increase focus. Also these rules can be transferred to social engagement to prepare for a social engagement, or to health management for diagnosis and treatment.

Possible functional components of the rules engine may include: state (update) transition matrix; context estimation; prediction; and stimulation. Other functions of the rules engine may include: needs to be able to generate decisions stochastically based on probabilistic models; needs to be able to update probabilistic models (e.g. cloud global search and annealing, using a user profile or multi-user profile); needs to be able to synchronizes sources of input so that relations can be established; needs to be aware of time delays if interactions between users are needed); needs to have a hierarchy of rules allow its function to be comprehended by the user; needs to estimate the impact of its actions on the user relative to its goals; provides a scripting language to build interaction with pre-compiled modules (e.g. scripted rules can run in the cloud and be optimized as in the case of PYTHONISTA™, or LUA such that the application is sandboxed and can't download malicious code. Rules modules may be downloadable, and may be implemented for example as JAVASCRIPT. The rules engine may be enable the insertion and removal of new rules; and real-time alteration of a pipeline of rules.

Non-limiting examples of features of rules may include: if visible to user; if created by user; if selectable by user; if detectable by user; if overridable by user; output characteristic (e.g. step response, etc.); input variables; output variables; output certainty; priority/precedence; timescale; and compute-scale.

Rules may be put together in a pipeline like a data flow processor (e.g. PD or max/msp). The rules may be applied to input streams sampled at a regular rate. The rules may be event driven where all required data needs to be available at an input before processing. The MC may determine a rule to be applied based on a final value received, or may take the previous values as input, wherein the rules is generated base on a message or subset of a message.

Different types of rules engines may be used, or different implementations of the rules engine may be implement or generate different types of rules. For example, in one implementation the rules engine includes inference rules (e.g. IF some-condition THEN execute-action). In another implementation, the rules engine includes reactive event condition actions, wherein reactive rules direct the rules engine to detect and react to incoming events and process event patterns (e.g. the event part specifies the signal that triggers the invocation of the rule). The rules provided may also implement logic. For example, a rule implemented to the rules engine may include a condition portion that includes for example a logical test that, if satisfied or evaluated to be true, causes an action to be carried out. Or another example of a rule ma include an action portion that triggers updates or other operations on local data. In another example, a rule implemented to the rules engine may include backward chaining starting with a list of goals (or a hypothesis) and works backwards from the consequent to the antecedent to see if there is data available that will support any of these consequents. In yet another example, a rule implemented to the rules engine includes opportunistic reasoning where knowledge elements may be applied either forward or backward, at the "most opportune time". In a still other example, a rule implemented to the rules engine includes deterministic rules similar thereby defining a deterministic rules engine.

Example events and conditions may include for example: (i) goals; (ii) events (such as "drowsy"; (iii) current activity (e.g. reading); (iv) time of day; (v) history (such as past responses to the same condition). These events an conditions may be used by the rules engine to (A) determine one or more relevant rules, and (B) apply the rules by operation of the rules engine so as to establish for example particular parameters for modulating content.

Further possible details regarding a manual override component are now provided. The manual override component may be implemented in software or hardware. The manual override component may receive or process a presentation control command received from a user. The manual override may provide for fine tuning for more or less of the modulation. The manual override may be applied before the modulation controller has determined any rules to apply, in order to modify selection or application of the rules. The manual override may also be applied after the modulation controller has determined the rules to apply, and after the modulator has applied the modulation to the presentation of the digital content, in order to cancel or confirm the modulation, or to modify the presentation further. The manual override may provide for: fine tuning for more or less of the modulation; adjusting the goal (e.g. rules engine behaves differently depending on the goal that the user has selected); adjustment of the modulation, including immediate adjustment; update or correction of the user's state; customizing the rules to be specific to the user; helping the system of the present invention to improve a prediction model by providing better labelled data as reported by the user; system error identification and correction; and change in mode of operation of the system based on user selection.

Accordingly, digital content presented to the user may be modulated (for example by modifying the presentation of the digital content) in real-time both when created by the user or when consumed by the user.

Features extracted from EEG signals vary widely across individuals. Factors such as age, work history, school performance at grade level, IQ, history of drug or alcohol abuse, history of psychiatric or cognitive problems, history of head injury or seizures, current CNS active medications, medical or neurological disorders, gender, ethnicity, weight and height, cigarette smoker or non-smoker, etc. contribute to this wide diversity. In addition to variance across individuals there is variance of EEG feature measurements within an individual caused by: drowsiness, agitation, time of last meal, time of day, etc. (see ref.: L. S. Prichep. Use of normative databases and statistical methods in demonstrating clinical utility of QEEG: Importance and cautions. Clinical EEG and Neuroscience 36(2), pp. 82-7. 2005. Available: http://search.proquest.com.proxytlib.uwo.ca/docview/206350047?accountid=15115).

Analyzing EEG signals to make accurate inferences about emotion, mood, and other brain states requires accumulating large annotated databases both across individuals and across different factors within an individual. Moreover, the ability to discriminate across subtle degrees of brain state requires an even broader collection of annotated EEG data.

The applications referred to in this disclosure that enhance content based on brain state, for the most part, may require an external database of annotated EEG data. As an example, the emotional response of a new user to a video can be estimated based on the EEG patterns that other users exhibited where the data and models of the other users are stored in a database (see refs: S. Koelstra, C. Muhl, M. Soleymani, Jong-Seok Lee, A. Yazdani, T. Ebrahimi, T. Pun, A. Nijholt and I. Patras. DEAP: A database for emotion analysis; using physiological signals. IEEE Trans. Affective Comput. 3(1), pp. 18-31. 2012. Available: http://resolver.scholarsportal.info.proxy1.lib.uwo.ca/resolve/19493045/v03i0001/18_dadfeaps. DOI: 10.1109/T-AFFC.2011.15; and M. Soleymani, J. Lichtenauer, T. Pun and M. Pantic. A multimodal database for affect recognition and implicit tagging. IEEE Trans. Affective Comput. 3(1), pp. 42-55. 2012. Available: http://resolver.scholarsportal.info.proxy1.lib.uwo.ca/resolve/19493045/v03i0001/42_amdfarait. DOI: 10.1109/T-AFFC.2011.25).

Emotagging Content Creation

In accordance with aspects of the present invention, an artist or creator of content may enhance the created content or artwork by adding elements driven by the creator's emotional state.

Figure 40:
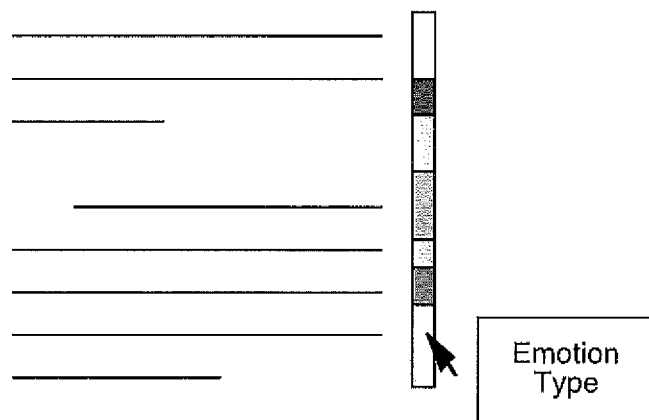
FIG. 40 shows creation of a text document with associated recorded brain state data of the document creator, in accordance with an aspect of the present invention.

As shown in FIG. 40, brain state data that is captured during the creation of a text document may be displayed together with the document. In particular, the brain state may be time coded to be associated with creation of particular passages of the document. The brain state data may then be presented in a graph, chart, or by any other indication type to a viewer of the document together with the document, as shown in FIG. 40. In this example, the brain state data is shown in the form of a bar in a margin of the document text. The bar shows the emotion of the author at the time of writing the particular text located on the same plane as the emotion indicated in the bar. The viewer may position a mouse pointed over particular locations of the bar chart to show more detail about the text and emotion.

As long as styles that are being modulated by brain state are fairly ambient and passive, emotype could represent a new channel of communication online. If e-mails, text messages, social media message, or any other online text communication were coloured based on emotional state, users could gain added insight on the brain state of their communication partners. Such a paradigm would depend on these modulations being easy to ignore, but easy to read when curious. For instance, if the arousal dimension of emotion were paired to blue and red, it would be an easy colour change to ignore, but if one chose to focus on it, could get an idea of the typist's brain state when expressing certain thoughts and ideas.

In the context of a drawing program, brainwave/emotion/state information may be introduced by creating a filters or patch for the respective drawing program (e.g. Adobe Photoshop). For example, the user's brain state may be processed, either destructively or non-destructively, in accordance with the present invention to change presentation of a scene. For example, as the user focussed, the contrast of a scene could increase. If the user was frustrated, the image could have a red transparent filter on it with increasing opacity as the user became more frustrated, or a "shattered" effect could be added on top of the image. The line styles could also change from precise and fine to jagged and thick based on brain state. Similar applications may also apply to movie editing or viewing programs, or to any other program type.

Text-Based Implementation

In one example embodiment of the invention, the brain state of a user is used by the system to modulate the appearance of text input by a user, for example by the user typing text. This may be done continuously and in real time or near real time so as to provide embellishment of the text without adding workload. The modulation may be implemented through an adaptive user interface.

Emotional state classification, based for example on applicable display rules, permits the addition of emotion embellishment similar to the use of emotions, but in an automated fashion, and way that is more closely aligned with various text portions so as to reflect the variation of for example emotional state during writing.

The text may be generated by typing or digital capture of handwriting.

In one implementation, the computer system of the present invention uses a plurality of signal ranges to define emotional state classifications. For example a two-dimensional signal may be used such as brain metrics of "relax" and "focus", and one or more display rules are associated with each of these metrics such as for example a particular font face.

Dimensional scaling may also be used. For example, a higher relax t=larger scale and lower relax=small scale. The same may be true for focus. This scaling may also be adjusted for aesthetic tasks. The adaptive user interface of the present invention may also be programmed to provide smooth front transitions as brain state changes, and to vary size depending on brain stage ranges within an emotional state classification for example for example by changing serif size dynamically.

There are many implications of the present technology. For example, a reader can consume content in a way that reflects the focus of the writer on selected portions, which may have bearing on the relative importance of particular passages for example. For example, attention may be focused on written passages that really matter (as identified by the technology of the present invention) while giving for example relative less attention to detail in other passages.

In one implication of the present invention, written communication is made more similar to verbal communication in that the embellishments serve to allow important content to be emphasized, and also permit less formality for less important content.

Creation of a verbal or written communication may have different stages, and encoding the communication based on brain state may be more evocative of the creator's intent depending on the stage. For example, in connection with modulating a written communication with the creator's emotions, an phase during which the communication is being edited for spelling may not be associated with emotions or strong emotions. In contrast, when a written communication is initially composed, perhaps in free form, and then once editing of the written communication is completed and the creator chooses to review the communication again, and experience the underlying emotions again, there may be stronger emotions that can be captured and encoded to the content, thereby evoking more accurately the creator's intent or the emotional context of the creation of the communication.

Reading-Based Implementation

The present invention may also be used for reading. For example, the present invention may be used in connection with an e-reader. The e-reader may include for example an e-reader computer program that is modified to include programming that, when executed, provides the functionality described.

In one implementation, when a user scrolls over the text as they read, their bio-state affects the font (font-face, size, color) and thus encodes their reaction to the text as the user reads.

This encoding of reaction based on brain state may be used for a variety of purposes. For example, the present invention may be used as a highlighter to embellish content automatically, for example text, to allow the reader to recall it more easily; to draw their attention in subsequent reads; to help them keep focused in the writing; reminding them of their state of mind/body and its relation to the content.

The encoding may be used to embellish activity feeds published by linking an e-reader for example to a social networking platform. When a user is reading a particular e-book, this information may be automatically shared with the user's social network, and the information may be encoded with state of mind/body experienced by the user when reading the e-book.

This encoding is also very useful to the writer (or the writer's publisher), and to other readers (in a multi user scenario). In the first case, the writer may get immediate and detailed feedback about how the writings affect the reader. In the latter case, many readers may contribute to the mark-up of a text, making it visible how the writing affected others as well as forming an automated way to aggregate the responses of many into a simplified model of how it affects people on average. Aggregation may involve generation of statistics regarding engagement of users with particular content, for example using a median, or mean, or mean with outlier rejection using a robust method such as m-estimator).

The information generated may allow writing to be optimized for comprehension through rewrites or similarly to maximize the reading efficiency through optimized highlighting. It also provides a useful tool for insight and exploration into reader interest.

The computer system may use this information for example to aggregate information regarding engagement by users with selected content. This information may be used in guiding the creation of additional content for example in conjunction with an e-learning platform. Also, a social media platform may match users that react to content in similar ways. Other uses and applications may be possible that leverage the advantages of the present invention.

In one particular implementation, the communication utility may be a journaling system. The enhancements of the present invention makes journaling more engaging, and stimulates insight and in some cases more honest an insightful communications. Particularly in the context of the use of journaling as a method for therapy, embellished journal content can provide useful content into non-verbalized emotions.

FIG. 3 for example illustrates how changes in the state of concentration may be captured and shown in regards to a user who is performing a task or completing an exercise.

FIG. 4 presents a representative output of the user interface, in this case display output associated with a self assessment from a journaling application, where content captured is enhanced with a modulated font and word cloud. This type of display provokes thought in users.

The user interface for displaying the enhanced content may also be accompanied with other associated information such as a mood chart which may be used to show an accurate representation of the mental state for the user.

Modulation of Social Media Content and Social Media Interactions

Emotions can be added via brainwaves to one's content feed. For example, on Facebook™, one might post that they are sad. They can do this by sharing their brain state via brainwaves as an emoticon or icon next to their text post. For example, the text post "i am feeling sad today", could be accompanied by a sadness icon or emoticon generated as a result of the users felt sad state. It could also be expressed in the text of the posting itself (in font), in the colour of the post, or some other indication on the user's profile photo or status update such as colour, text, video, etc, that would indicate state.

In a further implementation, others in the users social network could then post their own feelings (sad, happy, caring, loving, positive, etc), to show support for the users emotional state, whether empathetic (e.g. also sad, or angry the person is sad), or supportive by sharing their, for example, happy thoughts.

These other's supportive states and feelings can be expressed on the page by similar means (e.g. an emoticon next to a profile photo or post, in the profile, through colour, etc.).

There is also the possibility for the user to have an arena in which to capture and display the emotion that has been shared with them. So if a friend shares positive feelings with the user, that could show up within the social network, as a graph, series of emoticons, in profile picture, as colour, etc. In this way, users could share their "good vibrations" or "positive thoughts" with the user, and the user could capture them. The user could also receive a notification via email of the positive thoughts they have received.

In all these examples, heart rate and other bio sensors could also add signal or valance information. In particular, a measure of heart rate may determine a level of user arousal, particularly in conjunction with a determined brain state.

Facebook Like Via EEG

Like and dislike can be determined via EEG. One method of doing this is via hemispheric specialisation. There may be greater frontal right alpha activation relative to left activation when one is presented (real or imaginary) with something one likes. Similarly there is greater left frontal alpha activation when one dislikes something.

A "like" or other status in a social network can be determined via EEG, and shared in the social network by tagging content, photos, news stories, news feeds, status updates, etc via brainwave.

HRV, EEG and other bio measures can also add levels of arousal, and additional cross-measure for the degree of like.

For examples, items that are "liked" can be voted up, and items "disliked" can be voted down, or presented less frequently.

Tagging Items You "Notice" in Social Network

Whereas in Facebook we have a "like" button that one pushes manually if one likes something, With EEG one can immediately tag stimuli that one notices. When one notices something salient in the environment, a p300 brain wave may fire. This can be detected via EEG, and the item that was salient linked to the time course of the p300 firing. Items that were salient or noticed can then be tagged in a social network and shared, or if they are items already within the social network, they can be tagged with this "noticed" notification. This can cause them to automatically enter your social network (for example migrating from News Feed to your timeline), tagging or book marking them, sharing with others that you like it, or influencing the popularity and frequency of presentation of the content (influencing the Facebook social graphing back end). This notice allows you to curate your content based on what has caught your interest or attention.

The present invention enables new methods for tagging online content using emotions or brain state. This type of tagging provides a new mechanism for adding authenticity to online communications, such as communications via social networking sites for example by automatically tagging content based on emotional state or brain state, using the present system. This can improve the proximity or authenticity of connections between for example social network users. The tagging of content with emotional or brain state may also be used to filter social networking content, such as activity feeds.

An online identity is an actively constructed social representation of oneself on the Internet. Digital curation may be performed by an individual by hand selecting what the individual believes is great content, commenting and or providing context with a unique perspective to accompany a piece of content. Current online identities allow for the curation of one's self-presentation driven by a user's subjective opinion of content. Information, however, that is extracted from a user's brainwaves may add natural authenticity to an annotation of posted content which is more genuine than voluntary approaches to managing online identify. A user can be more self aware of the user's brain state as the user creates and/or curates content and can be used to determine how one's mood is influencing one's content creation.

Typical online communication tends to be ambiguous because it subtracts many of the normal cues of face to face communication (e.g. body language, facial expression, etc.). Brainwaves provide an opportunity and medium to add an emotional tone which will help users interpret the content created by others. The feeling of social intimacy can be increased when there is a more genuine expression of emotion. Content that is a more genuine representation of oneself has a greater chance of inspiring others to talk back, thereby enhancing engagement through the applicable social networking platform for example.

Technology has contributed to greater social isolation of people and the sharing of emotional state can help partially mitigate isolation. Emotional sharing is often encouraged in a number of group situations. The examples of groups interested in emotional sharing include: families, support groups, or any kind of tight-knit group. In one implementation of the computer system of the present invention, emotional sharing can occur automatically based on encoding of communications.

In a non-limiting embodiment of the present invention, the computer system may tag content based on a user's brain state or determined emotion(s). In one example, a user may post content to a social media service such as Facebook™. The user's post may include text, image(s), link(s), and/or video(s) and may be further annotated or annotatable with a summary of the user's brain state. Friends of the user on the social media service could, for example, click to see details of brain data of the user recorded while the content was created by the user. Any user may intentionally or passively tag a photo, image, or other content with emotions or other state information. When another viewer sees the content, it may be possible to view the state information of a person who previously viewed the content. For example, a user may see a sibling's wedding photo and exhibit a happy brain state, which is captured by the computer system of the present invention. The computer system may then tag the photo with this determined brain state, and the photo may be shared with other users together with the tagged brain state.

As mentioned earlier, the present invention may be used to filter social media interactions. Many social media websites (e.g. Facebook) have many users that curate "fake" personas. In one example of implementation of the present invention, the computer system of the present invention tags a person's post with their emotional state to show the world that they are being genuine. These posts benefit of increasing user's emotional self-awareness and fostering genuine communication and strengthening relationships. The user may want to post something genuine and writes a draft text of the post. A semantic analyzer may be used to determine the emotional tone of the post. The user's brainwaves may be analyzed and compared to the text. If there is not a large gap between the semantic analyzer and the emotional state as estimated by analyzing their brain waves then a genuine tag can be added to the post or one-to-one communication. The rule may be defined as follows: IF (User=Brain state of Mindfulness is Moderately balanced) THEN ACTION: "USER=Moderate Mindfulness Expert".

Figure 20:
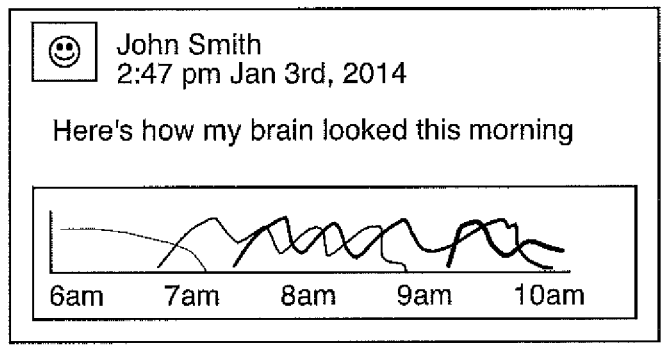
FIG. 20 shows an exemplary post to a social media service sharing brain state data of a user, in accordance with an aspect of the present invention.

Optionally, any brain state information tagged to a photo or other content, may either identify the user who exhibited the brain state, or the brain state information may be anonymized. For example, a tag on the photo may indicate that "10 people were happy when viewing this photo, and 2 people were unhappy when viewing this photo", without necessarily identifying which user experienced which emotion. An exemplary post with brain state information is shown in FIG. 20 which shows a social media posting by a user indicating brain state data for the user on a given day. Brain state information may also be tagged to a video posted to a social media service, or elsewhere.

Further possible details of implementation of the present invention for social networking are now provided.

Typically there is a list of people that the user knows and communicates with on social media, or in various chat services, or other communication services, with an indicator of the user's or the user's contact's current status (online, away, busy, etc.). With the content modulation system, people that have emo-state information available, may share this information and have it available to enhance the interface application for the user. This information would be used to modulate the user's status indication or may be used to modulate the user's current activity, or may be presented as content in itself (user state as content). The modulated content may presented in the same location (or next to) where their status is indicated. Different user will have different preferences on the display, and an interface may be provided to allow the user to customize it and also customize what is available to others. For example, a user will want to limit how much of the user's emo-state is available, and to whom. Different levels of privacy may be assigned to groups or individuals.

For example, the user's current status may appear as a colour that may be modulated using the user's current level of engagement and the user's manually selected state.

Where the user is available for chat and is not trying to concentrate (and therefore would generally be welcome to chatting), green would indicate that the user's has low mental load. High mental load may be rendered as orange. When the user is available for chat, but is trying to work (so they would be not want to be distracted if they are in a groove): low mental load+unfocused (distracted), indicator would be green; low mental load+focused, indicator would be orange; and high mental load+focused, indicator would be red.

The current status may be augmented with a rendering of user state that shows some of their state history. This can help other user's have a better idea of whether they want to disturb them or help them interpret their behaviour (humans are still much better than this than computer algorithms). The user's state history may be rendered as a scrolling line graph showing some of their recent brain state history. Brain-state may be rendered as a one-dimensional, or multi-dimensional graph. An implementation may be a one dimensional graph (so that it is not too complicated for other users to understand), where the x axis of the graph is time and the y-axis is related to brain-state, such as mental load. Greater on the y-axis is related to greater mental load. The time axis of the graph may be linear time (time ranges of 5 min to 5 s have been found to be particularly useful). Another useful feature is to use a non-linear time-scale (logarithmic typically) where the timescale is compressed more at the end of the graph representing more in the past.

Another column of information may be integrated into the UI that displays information about the user's real-time brain-state resonance ("in-sync") with their friends. This type of display is very useful for helping users know who they may have the best communication with, it also helps create feelings of connection between users and their friends, without the need for direct communication. The display may have different privacy settings than other aspects of emo-state modulation. For example, a user may not want to reveal what their current state is, but they may not mind a display of when they are in sync with another.

Useful measures of "in-sync" or "resonance" may involve analysis relative to a common stimulus. For example the application interface may have a dynamic visual aspect (like a video playing in a portion of the interface). Time synchronized analysis is done between the user's bio-signals and the features in the video content, yielding measures such as mental engagement with features in the video content. Correlation analysis is then performed between the measures from different users and used to estimate how "in-sync" pairs or groups of users are with each other. greater correlation being associated with more "in-sync".

The common stimulus may be each user's real-time emo-state, when it is rendered through the application interface. For example, each user's status is modulated with their emo-state (modulation may be the colour and intensity of the user's status indicator). Time locked analysis (for example correlation analysis between hue and intensity time-series of another user's status indicator, and the application user's bio-signals) is conducted to produce measures of coherence between the user and other users. User that are considering their list of friends will produce higher coherence between their biosignals and their friends status indicators, with higher coherence with those friends in the list that they are paying particular attention to. The advantage of computing coherence between the user and the status indicators rather than between the original bio-signals is the reduced amount of information transfer that is necessary, the reduction in privacy concerns. It also involves considerably less computation. Coherence scores are in themselves a time series that is shared with the application or website over the internet connection. The application (website) server can then process the collection of coherence scores between user's that are visible to each other, to create measures of "in-syncness" or "resonance". This analysis can be as simple as adding up the coherence scores over the appropriate time frame based on the individual user's behaviour, however in practice a probabilistic model is learned that can be user specific to improve the accuracy of the "in-sync"-ness measure. Different optimization criteria may be chosen depending on the application. For example, in a social site, the model would be optimized to produce longer conversations with more positive content, or greater content sharing with other users. For a work environment, the model may be optimized for greater discussion of work related issues. or less distraction (by monitoring how quickly people end the conversations).

Users may elect to share an experience together. For example a group may decide to listen to the same piece of music or video (ideally time synchronized). Analysis in this case would be similar to the first example, however stronger conclusions because user's will be focusing more intently on the same content. In example the user interface may be expanded to include a higher fidelity real-time modulation of the user's state indicator, since user's will be able to more directly connect with other individuals state indicators (and better understand relationships than a computer algorithm) because of it's time locked nature (time locked because the user's are all experiencing the same thing at the same time). In the case where there timing is asynchronous, or when user's attention may be moving to different portions of the application interface (or to other things in their environment), a computer algorithm would typically do better as it can look for correlations across large time ranges.

Other useful measures of "in-sync" or "resonance" may also be measured without a shared content experience. In this case a deep user profile may be useful as it can allow for more robust emo-state estimations and can be analysed with respect to interaction data with friends to yield a probabilistic model for what states are ideal for specific users to interact in. In this way "resonance" may be calculated by using emo-states from pairs of users (this may be computed on a trusted server, if people don't want to share their information). A "resonance" estimate would need emo-states of both users and the probabilistic model. This model would typically be initialised with a symmetric relationship (where users of like states yield the highest "resonance" probability) or with a more sophisticated model based on available data, but would be improved as more user data is collected (for example, high resonance may be estimated between a user who is "sad" and one who is feeling "loving"). Resonance may also be introduced into interface less directly by having user's with greater resonance come up in the interface as, for example, "maybe you would enjoy talking to friend X".

Figure 21:
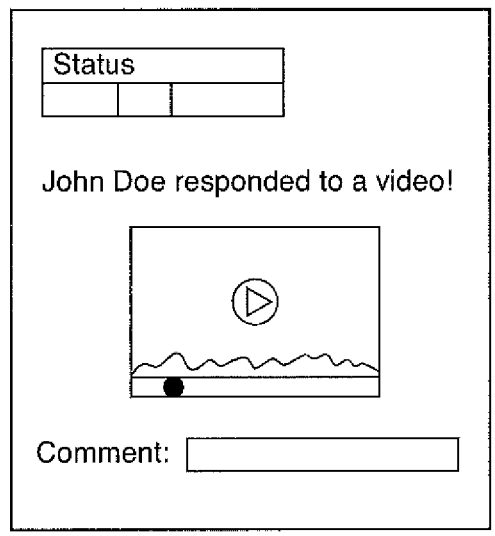
FIG. 21 shows an exemplary post to a social media service sharing brain state data of a user associated with a shared content item, in accordance with an aspect of the present invention.

Another example is shown in FIG. 21 which shows a video posted to a social media service. The video includes an indication of the user's brain state while watching the video. The user's brain state may have been recorded and time-coded, then the computer system may have uploaded the time-coded brain state information to the social media service to tag the video. The tagged brain state information may be shown as an overlay of the video, as shown in FIG. 21, or may appear in a separate table or window, or may appear in textual instead of graphical form.

Figure 22:
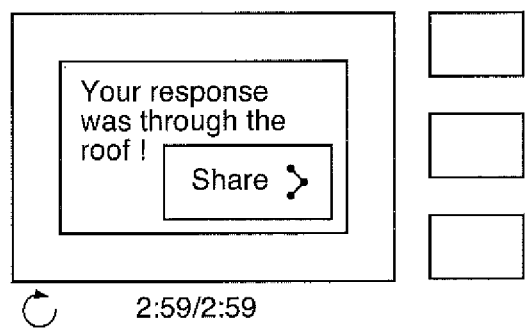
FIG. 22 shows an exemplary indication of a user's brain state upon completion of presentation of a content item, in accordance with an aspect of the present invention.

An example of video tagging is shown in FIG. 22 which provides an indication of the user's brain state upon completion of presentation of the video. The user may be notified of a particular brain state response determined from the user's bio-signal data obtained by the computer system of the present invention. The user may then be prompted to share the brain state response or not, or to maintain the brain state information, but only show it to the user, and not share it. The options for sharing this information may be shown as buttons to click or check off to the right of the video window, as shown in FIG. 22.

While wearing the bio-sensor(s) of the computer system of the present invention, the user may watch a video on a video sharing service, such as Youtube. The computer system may determine that the user is exhibiting a particular brain state or emotional response and notify the user accordingly. The user may respond to the notification to share the user's response on Facebook, Youtube, or any other suitable service. The user may manually login to the respective service or the computer system may be configured to automatically login for the user. The user may be prompted to select users or groups of users with which to share the brain state data. The user may include text for posting together with the brain state data, and optionally a link to the video.

In the case of Facebook or any other social network, the user's timeline or equivalent may be shown with a post including the user's brain state data. Such a post may be referred to as an "emotagged" post. Other users with whom the post was shared may view the emotagged post in a format determined by the user. For example, the user may choose to present the brain wave data as a "happy face" representation, as a graph or chart, as text, by a colour or any other graphic or embellishment or enhancement or modification of the shared content. For example, the shared video may be shared with a coloured border surrounding all or part of the video window. A colour of the border may be selected to be indicative of the brain state or emotion of the user who has shared the video, as shown in FIG. 26. For example, a red border may indicate that the user was angry when watching the video; a blue border may indicate that the user was sad; and a green border may indicate that the user was not experiencing any significant emotion while watching the video. If a user watches a video while not wearing the bio-signal sensors, the user may opt to re-watch the video while wearing the bio-signal sensors in order to record bio-signal data for sharing.

Figure 23:
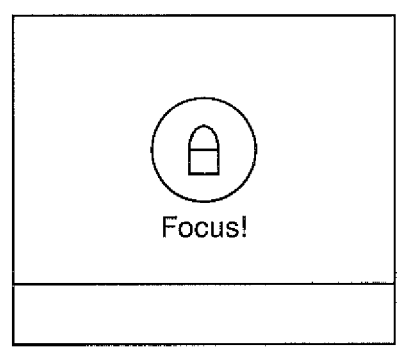
FIG. 23 shows an shared video locked for viewing until a viewer achieves a particular brain state, in accordance with an aspect of the present invention.

FIG. 23 shows another implementation of the present invention, where a particular shared video is locked for viewing until the viewer achieves a particular brain state. The uploader or sharer of the video may select the brain state, or intensity of brain state to achieve before viewing is granted by the computer system or video sharing service. The video may be unlocked once the brain state has been achieved a single time, or the viewer may be required to maintain a particular brain state for the duration of the video in order to continue to watch. Optionally, should the viewer's brain state not meet the established requirements, then the video may pause or stop. Optionally, a message may be displayed directing the viewer to "focus" or try to achieve the desired brain state in order to resume playback. Accordingly, a set of rules may be associated with content that require the user consuming the content to achieve certain brain state parameters in order to be permitted to consume the content, or unlock particular content sub-components.

Figure 24:
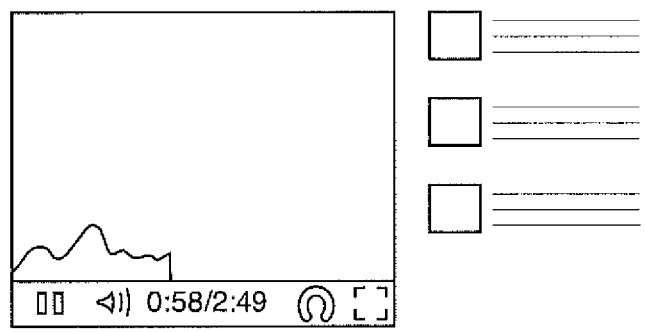
FIG. 24 shows an implementation of an aspect of the present invention, where a shared video is being viewed and the viewer's bio-signal data is being tracked and recorded.

FIG. 24 shows an implementation of the present invention, where a shared video is being viewed and the viewer's bio-signal data is being tracked and recorded. As both the video and the bio-signal data is time-coded, an overlay or separate window may be presented on the video showing the viewer's bio-signal data, or brain state response to viewing the video at the particular time codes indicated by a video playback progress indicator. An icon or other indicator may also be shown either in a status bar of the video window, or elsewhere, to indicate whether current bio-signal data is being recorded, as such bio-signal data recording may be toggled by clicking an appropriate control input displayed at or around the video playback window, or by pressing a suitable keyboard key, or by providing a suitable voice control command.

Figure 25:
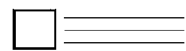
FIG. 25 shows an implementation of an aspect of the present invention, where photos or other content are grouped and displayed by brain state information tagged thereto.

FIG. 25 shows an implementation of the present invention where photos or other content are arranged, organized, filtered, or otherwise grouped and displayed by brain state information tagged thereto. The user posting the content may have tagged each content item with brain state information when uploading, posting, or sharing the respective content item. Accordingly, content items tagged with a brain state of "happy" may be retrievable and displayable together by suitable query.

When a user is consuming digital content presented to the user, the user's current brain state may be communicated to the user. For example, a graphic may appear on a display screen of the computing device used by the user to indicate the user's current brain state, as shown in FIG. 27. This graphic may take the form of an avatar or representation of a person or face, that is made to appear happy when the user is in a happy brain state, or is made to appear sad when the user in a sad brain state. A brain state graph may also be shown indicating a value of the user's present brain state, which may be updated in real-time or pseudo-real-time.

Optionally, when either consuming presented digital content, or viewing shared content having associated brain state data of a user, a graphical representation of the brain state data available may also be presented with radiating lines or rings that increase and decrease in size, intensity, or in any other property based on the brain state data. For example, as the brain state data indicates more intense feelings of happiness, the radiating lines may increase in intensity, and when feelings of happiness decrease, the radiating lines may decrease in intensity.

Figure 28:
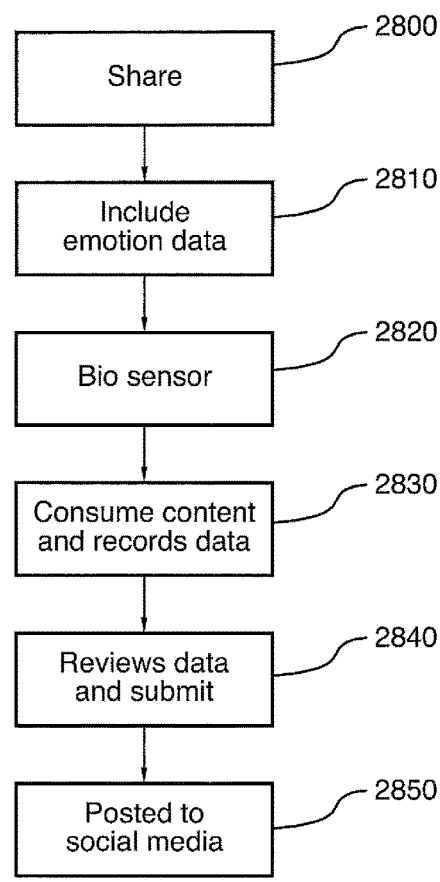
FIG. 28 shows exemplary method steps of an aspect of the present invention, to share content.

FIG. 28 shows a non-limiting method of the present invention. The user may click to share content (e.g. a video) on Facebook at 2800. At 2810, the user may be asked to include emotion or brain state data with the shared content. If the user clicks to share this data, the user may be prompted to put on the bio-signal sensor(s) at 2820. At 2830, the user may watch the video, and the user's bio-signal data, and determined brain state data may be recorded by either the user's local computing device, or a remote computing device in communication with the user's computing device. The recorded bio-signal data may be time coded to correspond to time codes of the content presented. At 2840, the user may be prompted to review the recorded/determined brain state data. Once satisfied, the user may click to submit the shared content with the associated brain state data. At 2850, the shared content and associated data may appear on the user's Facebook profile. The user may share such content on other content sharing services as well.

Figure 29:
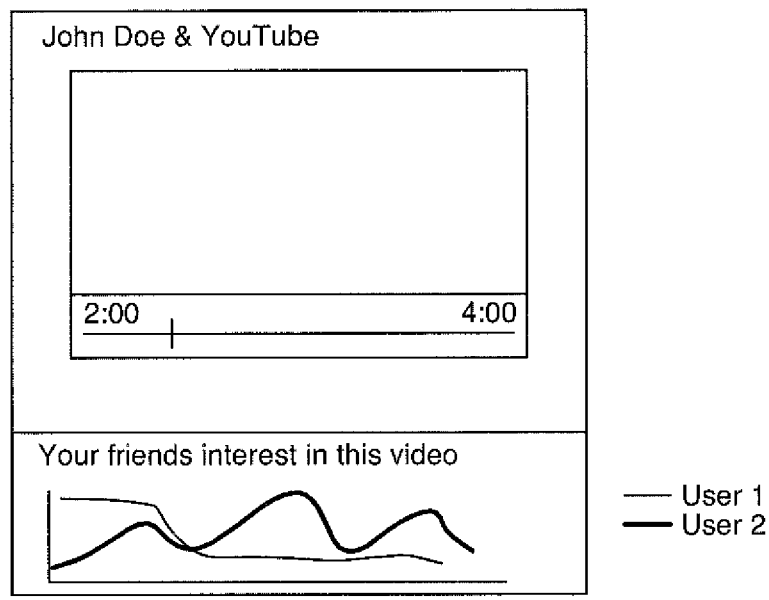
FIG. 29 shows an example of a shared video in accordance with an aspect of the present invention.

FIG. 29 shows a non-limiting example of a shared video in accordance with the present invention. Other users may have subsequently viewed the shared video, also when wearing their respective bio-signal sensor(s). The brain state data of the respective users viewing the video may also be shared and associated with the shared video. Accordingly, this brain state data may also be displayed to subsequent users accessing or viewing the shared video. The brain state data may be shown in a time-coded graph, as shown in FIG. 29, or by any other format.

Figure 30:
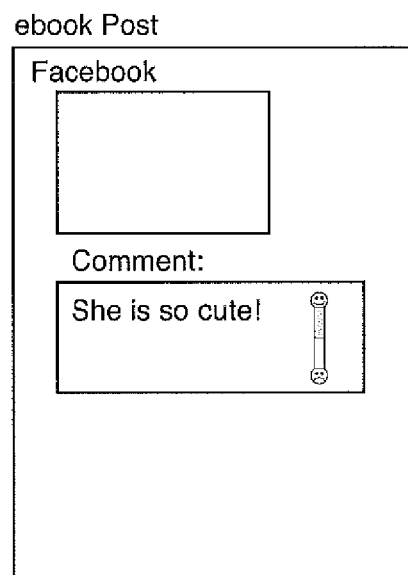
FIG. 30 shows an example of a representation of a user commenting on a post on social media service.

FIG. 30 shows a non-limiting example of a representation of a user commenting on a post on Facebook. Together with the user's text comments, if the user's bio-signal data is also being recorded, a graphical indication approximating the user's brain state may be associated with the user's comment to indicate. Optionally, this graphical indication may indicate whether the user was happy or sad when posting the comment, and may optionally indicate an approximate intensity of the determined brain state.

Figure 31:
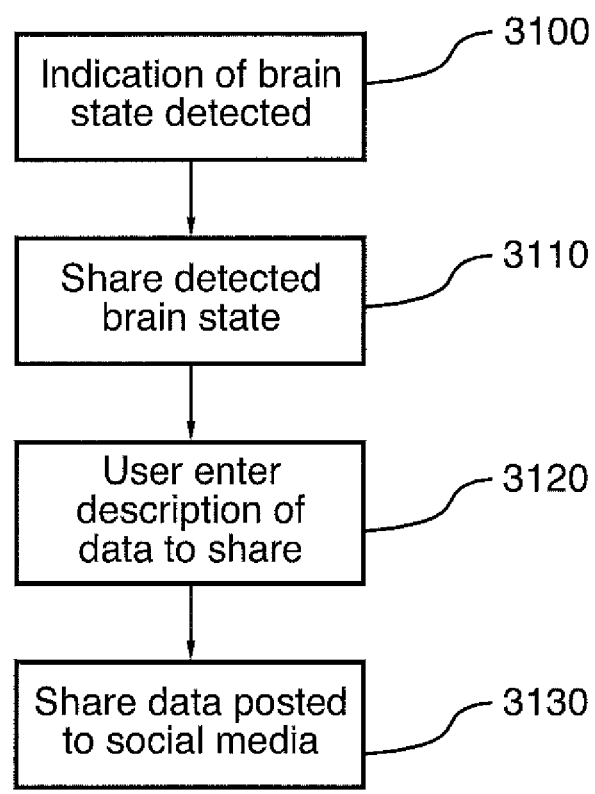
FIG. 31 shows exemplary method steps of an aspect of the present invention, to share content.

FIG. 31 shows a non-limiting example of a method of the present invention. The user may be viewing a video on Facebook, Youtube, or any other video service, or simply on the user's computer in a video player application, while wearing the bio-signal sensor(s). At 3100, An icon or other graphical or audio indication may be provided indicating to the user that a particular brain state has been detected from the user. For example, the icon may indicate that the user is experiencing above-average happiness. At 3110, the user may click the icon, or interact by any other means, to share the video. At 3120, the user may be prompted to provide a text comment for the shared video or shared link to the video. The user may be prompted to share the determined brain state, either by sharing an approximate emotion associated with the entire video (e.g. happiness) or by sharing more detailed time-coded brain state data of the user. At 3130, the shared video is posted to the video sharing service with the user's comments and optionally with the shared emotion or brain state data. An embedded video player (such as a Youtube video player) may be implemented in an application, or web browser using an Application Programming Interface (API) supplied by Youtube. Other video players may provide similar APIs. Once a video player is embedded into an app, it may be polled to determine information, including: YouTube Video ID specifies and identifies the played video; video player status (e.g. not started, ended, playing, paused, buffering, video cued; elapsed time in seconds since the video started playing; and total bytes of video that can be used to derive duration of the video.

Tagging videos or other content with brain state data, or "emotagging", may be accomplished by installing an application on a user's computing device. The application may include an embedded video player or the app may communicate with a web browser application installed on the user's computing device. The browser may provide the ability to query the video player for information and send the information to the app (or the app can query the embedded player and receive the information), the information including: video identifier ("ID") (may specify and identify the played video); video player status (e.g. not started, ended, playing, paused, buffering, video cued; elapsed time (in seconds since the video started playing); and total bytes of video that can be used to derive duration of the video. The user may open the browser and visit a video service such as YouTube while wearing the bio-signal sensors and search for a video. The user may click a video from the search results. The app, or a separate app interfacing with the bio-signal sensor(s) may receive a message from the player that the user is watching a video identified by the video ID. The app may assign a session ID based on the current calendar date and time. The app may also assign information including: User ID; Activity Type (e.g. "watching video"); and app data including Signal Type (e.g. EEG), timestamps per EEG sample, timestamps associated with start and stop of watching the video, and raw EEG data per channel. The app may label the timestamp "start of video" into the EEG data. The app may poll the video player to get elapsed time of video. The elapsed time plus the start time may be used to label timestamps in the EEG signal. Event timestamps of the location in video may be sent if video is paused. There should be an association of the timestamps of the EEG recording with the progress timestamps of the video in order to associate events in the video with particular bio-signal data at particular times. This may be accomplished by using event timestamps that have the timestamp as well as an event label such as paused video. The app or the cloud platform may analyze the EEG signal for classification into an emotion somewhere in the continuum from sad, stressed to happy, elated corresponding to time scale of the video. A graph of this continuum may be displayed as well as the average and peak emotions felt while watching the video. The user may click a share button located at, under, or near the video. Clicking a Facebook icon in the sharing options pane that appears may prompt the video to be shared on Facebook. The user may be prompted to login. The user may then be prompted to select which users may see the video (e.g. Friends Only, Public, Family, etc.). The user may also be prompted to determine how much, if any of the emotagged data is to be shared (e.g. full continuum of emotion along timescale or just one word summarizing the user's emotion). The user may be prompted to enter a message to post with the video. Clicking a share link button may then post the video with the optionally attached emotagged data. The EEG signal and analysis may be provided to the user's profile in the cloud platform.

Figure 32:
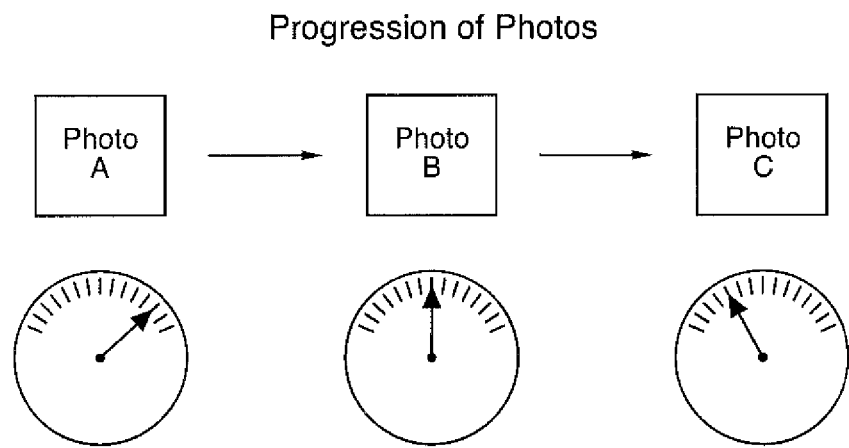
FIG. 32 shows a brain state indicator that may be presented for respective content items, in accordance with an aspect of the present invention.
Figure 33:
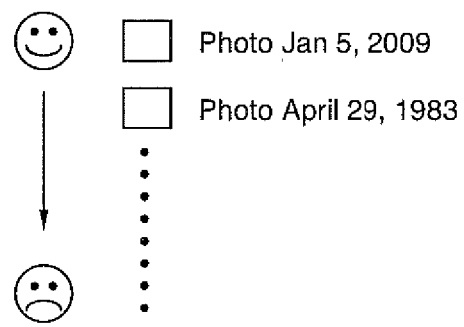
FIG. 33 shows an implementation of an aspect of the present invention, where a list of content items is sorted by brain state data.

In a non-limiting exemplary embodiment of the present invention, one or more digital content items may be presented to the user, in succession. The user's bio-signal data may be measured by the bio-signal sensors and the user's brain state may be determined. For each content item presented, the user's bio-signal data or brain state data may be associated with the respectively presented content item. This feature of emotagging content items in succession may be referred to as "emocrawler". This may be accomplished by tagging the content item with metadata, or storing a separate data store with the associated data, or by any other means of association. The user may cycle through the presented content by clicking buttons such as "previous" or "next" or any other navigational buttons. The user may be asked to confirm the determined brain state determined by the computer system before associating it with the presented content item. Content items may then be later retrieved, grouped, displayed, presented, filtered, or prioritized by the respectively associated bio-signal data or brain state data. In particular, the associated data may be used to curate categorize and/or curate the user's content based on the user's emotional reaction to the content. For example, a video montage can be edited based on the editor's emotional reaction to the video content. As shown in FIG. 32, a brain state meter may be displayed when presented each content item. The brain state meter may update in real-time or pseudo-real-time while the user views or otherwise consumes the content, or the meter may display a previously recorded brain state associated with the content. The user may be asked to re-record new bio-signal data for the content, especially if the user wishes to discard the currently associated data. FIG. 33 shows sorting a list of content items by brain state data (e.g. emotional valence). The content items may be sorted by happiest associated brain state or saddest associated brain state, or by any other associated brain state. Optionally, when the user is navigating through a plurality of content items (e.g. vacation photos) and associating a brain state with each photo upon viewing the photo, the photos may then be sorted by emotional response. A list of all the emotional responses associated with all the photos in the photo set (e.g. all the photos grouped for a particular event or vacation, etc.) may also be shown along a side of the presented content. Clicking on one of the associated emotions may cause a specific action to occur on the respectively tagged photos. For example, all photos tagged with that emotion to be displayed in thumbnail form, or a slideshow may begin for those photos.

Tagging content items in this way may be advantageous due to the proliferation of social media which encourages users to generate and share an abundance of content, optionally with other users over the Internet, which directly relates to the user. This abundance tends to have a very low signal to noise ratio, as posts, pictures, events, videos, etc. are produced and shared every day. Brainwaves represent a quick and entertaining way to genuinely annotate content and increase the signal to noise ratio on any user's massive online store of self-referential content. Just like Facebook is a cloud-based database for photos and life events, the present invention may provide for a cloud-based repository for brainwave data and processed brain data (e.g. with emotional state or level of focus, etc., determined), that can be stored separately or together with Facebook's content. The user may also tag content on other social media sites and through other social mediums, such as Twitter, My Space, Snap Chat, BBM, SMS, etc.

In another non-limiting application of the present invention, journal content may also be emotagged. For example, a user may write a diary or journal for therapeutic purposes. The user's emotion(s) may be detected and recorded using the computer system of the present invention. These emotions may be used to tag passages of the journal with emotions that the user may not even be aware of. An avatar may be used to represent the emotions or mood felt by the user making a journal entry. The avatar may be animated by emotions that are driven by the actual emotions of the user as detected by the computer system of the present invention. By becoming more aware of the user's emotions tied to certain journal entries, the user may gain increased self-awareness which can be therapeutic. Content could be shared with a spouse or doctor. Text to speech conversion could read journal entries back to the user modulated with the emotion that the user felt when writing the respective entry. The journal may be written in a word processing application with time stamps synchronized to time stamps of the recorded bio-signal data by the computer system in order to determine what journal entry triggered what brain state in the user. Writing therapy may have a positive impact on health outcomes such as a reduced number of physician visits, improved immunity, and a reduction of negative emotions (see reference: Pennebaker, James W. 2003. Writing about emotional experiences as a therapeutic process. p 362-368 Psychology Press, New York, N.Y.). In addition, increasing self-awareness of unconscious motives, and beliefs may beneficial to mental health (see reference: Wilson, Timothy D., and Elizabeth W. Dunn. 2004. Self-knowledge: Its limits, value and potential for improvement. Annual Review of Psychology 55: 493-518). Similarly, other digital content including text messages, emails, word processor documents, presentation documents, or any other type of digital content may be tagged with brain state data, more general bio-signal data, or emotions either generally or time-coded with creation or viewing of the respective content. In a non-limitation example, the user may compose a text message, wait for a period to settle on particular feelings regarding the text message, and the text message may be modulated based on the user's determined brain state. The user may encode a dynamic feeling such as a 30 second movement of emotion. The user could re-examine the user's emotion, adapt, iterate, and determine if it is consistent with the intended effect. This may provide for a collaborative creative process that is done with the computer that cycles through compose, feel, compose, feel, etc.

Figure 34:
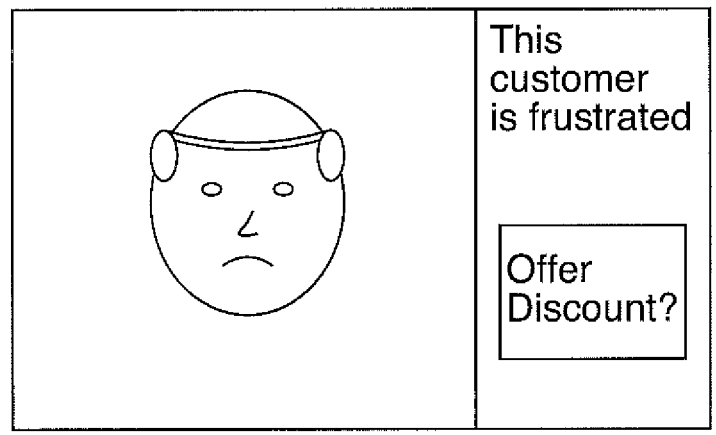
FIG. 34 shows an example of a video conference where a conference participant's brain state data is also presented, in accordance with an aspect of the present invention.

FIG. 34 shows another non-limiting embodiment of the present invention. A video chat window is shown, showing the other chat participant wearing bio-signal sensors of the computer system of the present invention. In this example, the video chat is specific to a technical support video chat where the customer, the chat participant shown is determined to be frustrated by the computer system of the present invention. The chat participant's brain state data may be communicated to the other chat participant (e.g. to the technical support representative) who may be prompted to offer a discount, coupon, or other incentive to the other chat participant. Accordingly, a user's brain state may be communicated to other chat participants in video or audio chat conferences. The respective user's brain states may be shown to the user who generated the brain state, and also to any other users participating in the chat. The presented brain state may be representative of the respective user's current brain state, or a full or brief history of the user's brain state may be shown or available to be shown, from either a part of or from the beginning of the communication session.

Figure 35:
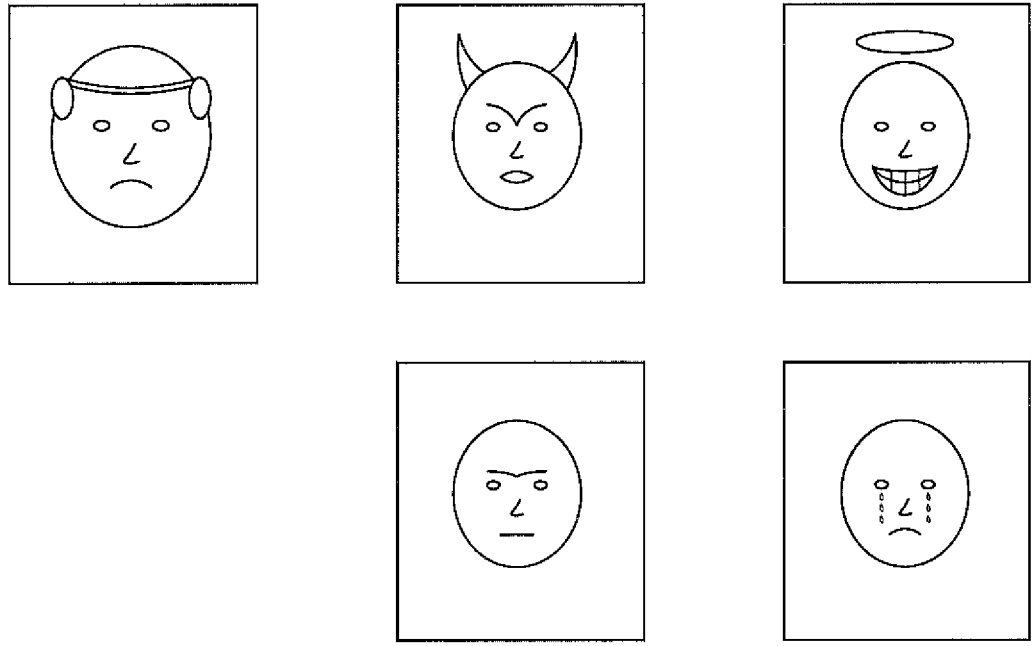
FIG. 35 shows an example of a video conference where the received brain state data of a chat participant may be used to overlay a visual representation of the emotion over the video, in accordance with an aspect of the present invention.

FIG. 35 shows another non-limiting example, where the received brain state data of a chat participant, shown on the leftmost box of FIG. 35, may be used to overlay a visual representation of the emotion over the video chat image of the chat participant experiencing the particular brain state. Examples of such overlays are shown in the remaining boxes in FIG. 35. For example, if a chat participant is determined to be experiencing a happy brain state, the video stream of the user may be modified to overlay happiness graphics, such as a halo, sunshine rays, or other graphics, over the video image. The contrast, brightness, or other properties of the video stream may also be modified accordingly. Where the user is determined to be sad or angry, other graphics, such as lightning bolts, horns, or angry eyebrows, or darker colours may be overlayed on the video image, or other video properties may also be modified. When the user is disinterested or confused, or judgmental, the user's brow may appear furrowed. When the user is sad, tears may be overlayed on the user's face. The video image itself may also be distorted to enlarge certain aspects of the chat participants visual appearance, or minimize other aspects, according to the chat participant's determined brain state and any modification rules provided by the computer system of the present invention.

FIG. 44 shows another non-limiting example where a list of a plurality of callers are waiting in a queue. The length of time each caller has waited for is indicated, as is the respective caller's brain state. Calls may be answered in priority of the most frustrated or angry caller to the least frustrated or angry, or by any other brain state measure.

Other examples of brain states affecting live or asynchronous communication between people may include: emotions change robotic telepresence (e.g. Robotic flower reflects communication partner's brain state. Robotic telepresence body language reflects communication partner's brain state. Emotional state of one partner can be sonified and sent to the other partner. The distraction level of the communication partner can be monitored, using for example the computer system of present invention for measuring brain state and phone in accordance with the present invention can give feedback to the communication partner for example on the other party's distraction level.

In one possible implementation, the present invention can provide an enhanced communication tool for individuals with cognitive deficits (for example people that have difficulty expressing themselves such as people on the autism spectrum or having dementia). Such individuals can used the system of the present invention to represent their emotions to people around them. This would make it easier to understand a person with a cognitive deficit. A caregiver can more easily recognize when the person being cared for is upset or agitated but may not have external signs of agitation.

Another non-limiting embodiment of the present invention may be provided where, as previously described, content viewed or created by the user may be tagged, sorted, or ranked based on respectively associated brain states. The computer system of the present invention may use this associated information in order to rank user preferences or provide recommendations to the user. For example, the user may effectively rank preferences of music, video, movies, television shows, or other content by the computer system processing the user's brain state associated with each of the respective content items. The brain state information may be provided together with the user's personal content preferences. Preferences provided by the user may also be used by the computer system to fine tune the brain state determination. This may allow for increased accuracy of content recommendations to what the user would actually prefer. For example, particular content items (e.g. movies) that have been viewed by the user and have respective user brain state data associated therewith may be presented to the user in a list. The respective associated brain state data for each content item may be shown. Content items determined to produce a happy, alert, aroused or other "positive" brain state response may be determined to be preferred. Other content items or movies having similar properties to those determined to produce the positive responses may be recommended to the user. Optionally, other users that have responded similarly to the movies viewed by the present user, may have experienced positive brain state responses for other movies as well. Those other movies may then be recommended to the present user. Optionally, other users having bio-signal classification profiles, or user profiles, similar to the present user, may be identified by the computer system of the present invention and content items preferred by those respective users may also be recommended to the present user.

Rating content is generally done in prior art systems and solutions in a subjective way. In contrast, brain state can add an objective element to rating content. Typical content rating systems involve a single rating (e.g. number of stars from 1 to 5) which takes place after a user engaged with that content. Live brainwave algorithms could get more nuanced detail subconsciously while users are engaging with the content. Further, the temporal nature of a real time measure would allow the recommendation engine to detect a user's response to a specific moment, or specific sections of the content. Machine learning algorithms which currently underlie most recommendation systems may benefit from having recommended content also measured based on output from the computer system of the present invention. in terms of brain state algorithms of the present invention. Machine Learning algorithms typically use a training paradigm, thus real-time and immediate feedback on the accuracy of every recommendation may be of benefit to the improvement of recommendation engines in general.

Figure 13:
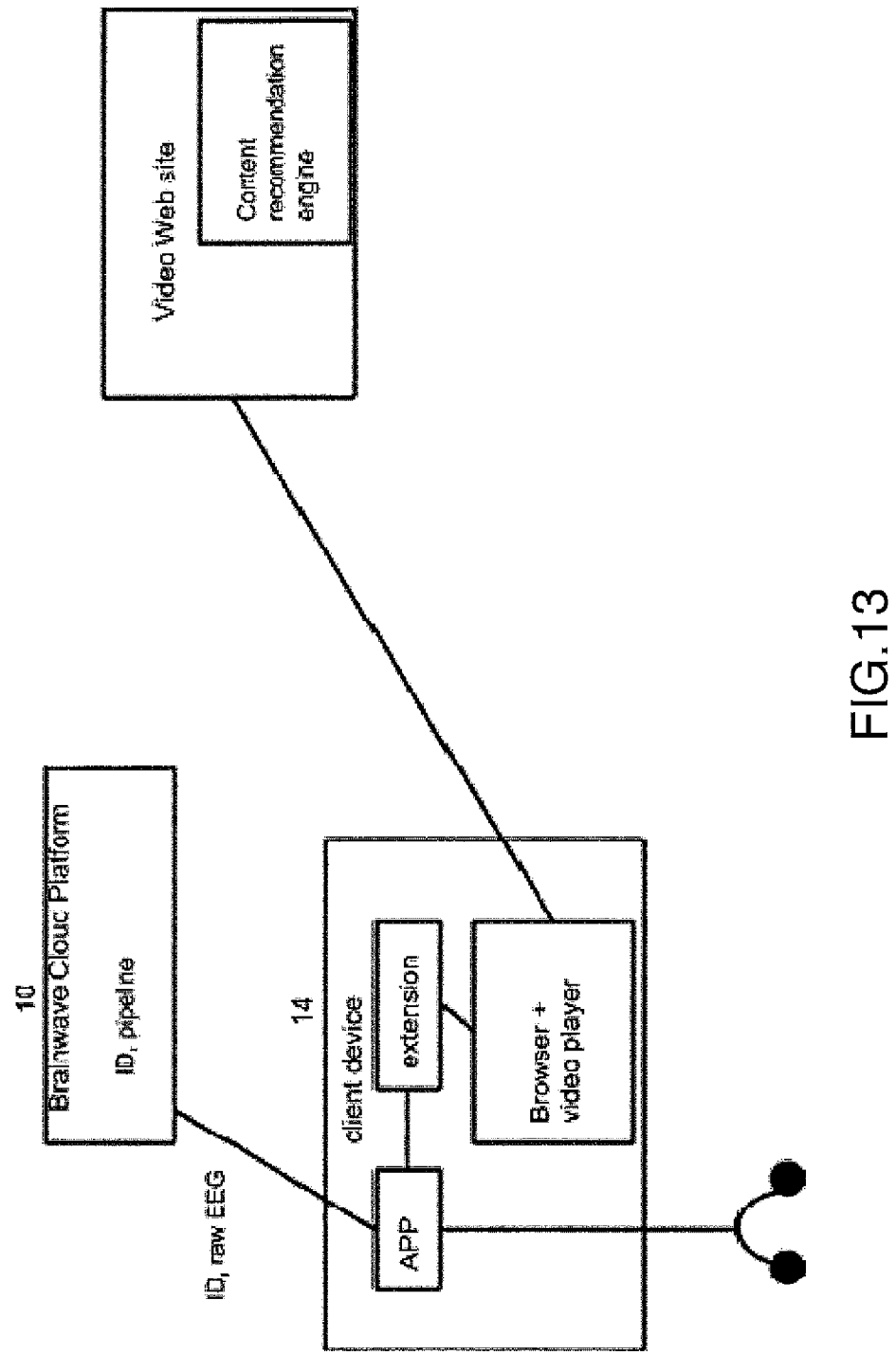
FIG. 13 illustrates a system diagram view of an embodiment of the present invention.
Figure 14:
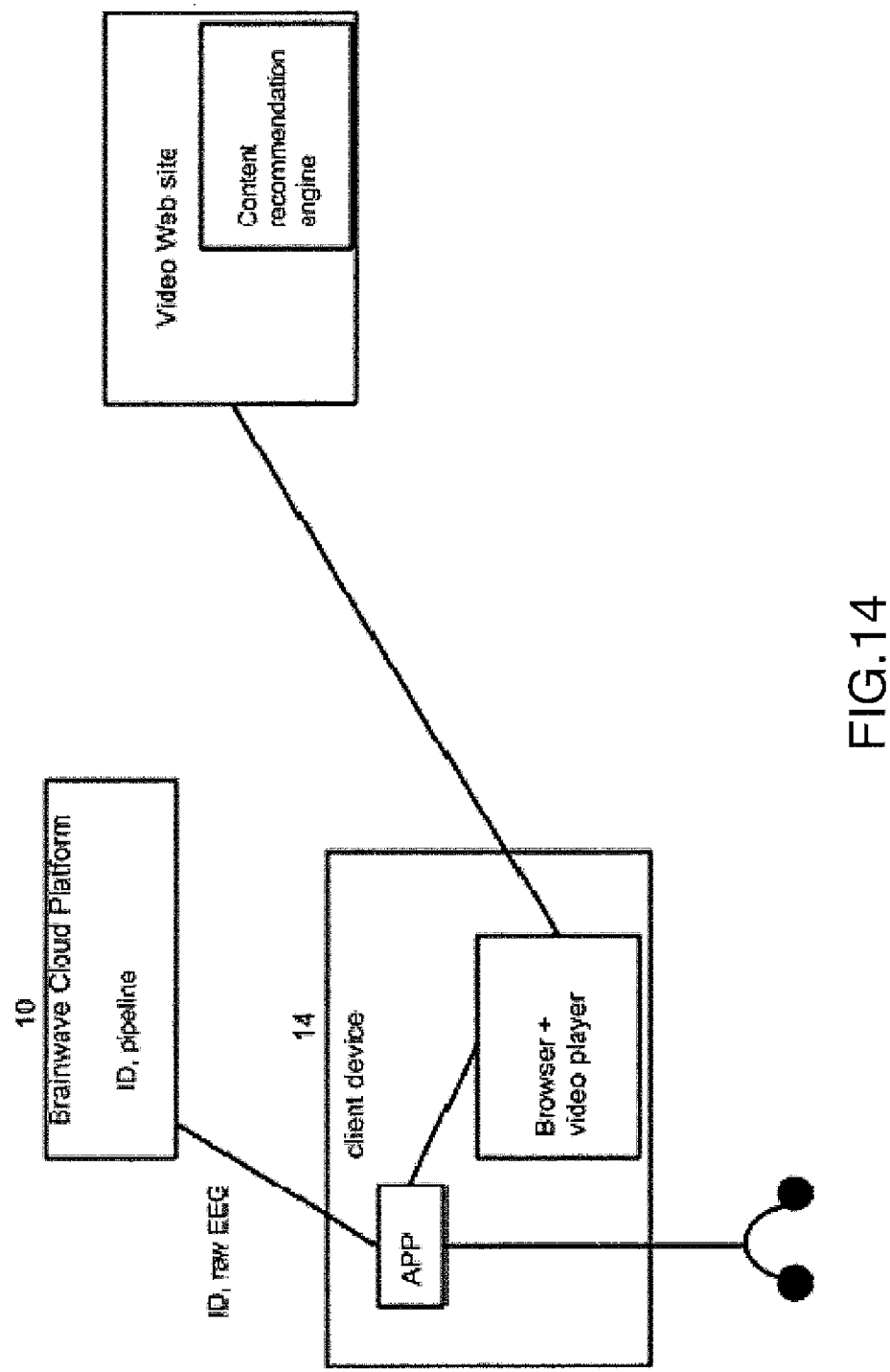
FIG. 14 illustrates a system diagram view of an embodiment of the present invention.

Shown in FIG. 13 is a non-limiting implementation of the present invention showing a client computing device 14 in communication with a brainwave cloud platform 10 of the present invention. The client computing device may include a bio-signal processing application, as described, linked through a web browser extension or video player extension to a web browser or video player. The web browser and/or video player may connect to a video sharing web site which includes a content recommendation engine. Optionally, as shown in FIG. 14, the bio-signal processing application may interface directly with the web browser or video player. The application supporting emotagging may be installed on the user's computing device. The application either may have an embedded video player or may communicate with the user's web browser. The web browser may have the ability to query the video player for information and send the information to the application (or the application can query the video player through a browser extension to receive the information), the information including: Video ID specifies and identifies the played video; Video player status (not started, ended, playing, paused, buffering, video cued); Elapsed time in seconds since the video started playing; and total bytes of video that can be used to derive duration of the video. The user may open the browser and send a HTTP query to a web site that hosts the video and logs in. The web site may send an HTML page to the user's browser with a search box for videos plus recommendations for movies to watch based on the user's preferences as stored in the web site's "Content Recommendation Engine". While the user is wearing the bio-signal sensors (e.g. an EEG headset), the user may enter keyword text to search for a video. This HTTP message is sent to the web site. The web site returns HTML with a list of videos that match the user's request possibly sorted by a ranking algorithm weighted by the user's preferences. The user may click on a video from the search results. The application may receive a message from the video player that the user is watching a video identified by Video ID. The application may assign a session ID based on calendar date and time. The application may also assign information including: User ID; Activity Type "watching video"; and application Data including Signal Type (e.g. EEG), timestamps per EEG sample, timestamps associated with start and stop of watching the video, and raw EEG data per channel. The application may label the timestamp "start of video" into the EEG data. The application may poll the video player to get elapsed time of video. The elapsed time plus the start time is used to label timestamps in the EEG signal. Event timestamps of the location in video are sent if video is paused. There needs to be an association of the timestamps of the EEG recording with the progress timestamps of the video if we are to associate events in the video. These are done by using Event timestamps that have the timestamp as well as an event label such as paused video. The application may send raw EEG data plus timestamp data to the Brainwave Cloud Platform of the present invention. The platform may analyze the EEG signal and classifies into an emotion somewhere in the continuum from sad, stressed to happy, elated corresponding to time scale of the video. A graph of this continuum can be displayed as well as the average and peak emotions felt while watching the video. The platform may send the emotional classification to the user's application. The application may associate the Video ID with the emotional classification received. The application may send this to the Browser. The Browser may send a message with the Video ID and emotional classification to the video web site. The video web site may use information about the movie to build a feature set for that Video ID. The feature set can include emotional classification based on the user's brainwaves while watching the video. The video web site may build a classification model and or rules using machine learning. The web site content recommendation engine can make recommendations based on the rules it has learned about the user's preferences.

In a non-limiting example, educational or learning content may be provided by the computer system of the present invention where the presentation of the content is modified based on the level of concentration or focus or other brain state experienced by the user, determined as described. Similarly, in another example, a feed of web-based content (e.g. a live or pre-recorded feed) may be changed based on user's brain state. The delivered content can be made more engaging, relaxing, etc. based on the brain state of the user. Similarly a scroll rate of a text or web browser view can be modified based on a determined level of focus/alertness of the user which may be indicative of the user's ability to retain information. The difficulty level of the learning content may be modified based on the degree of focus of the user at the relevant time.

Figure 36:
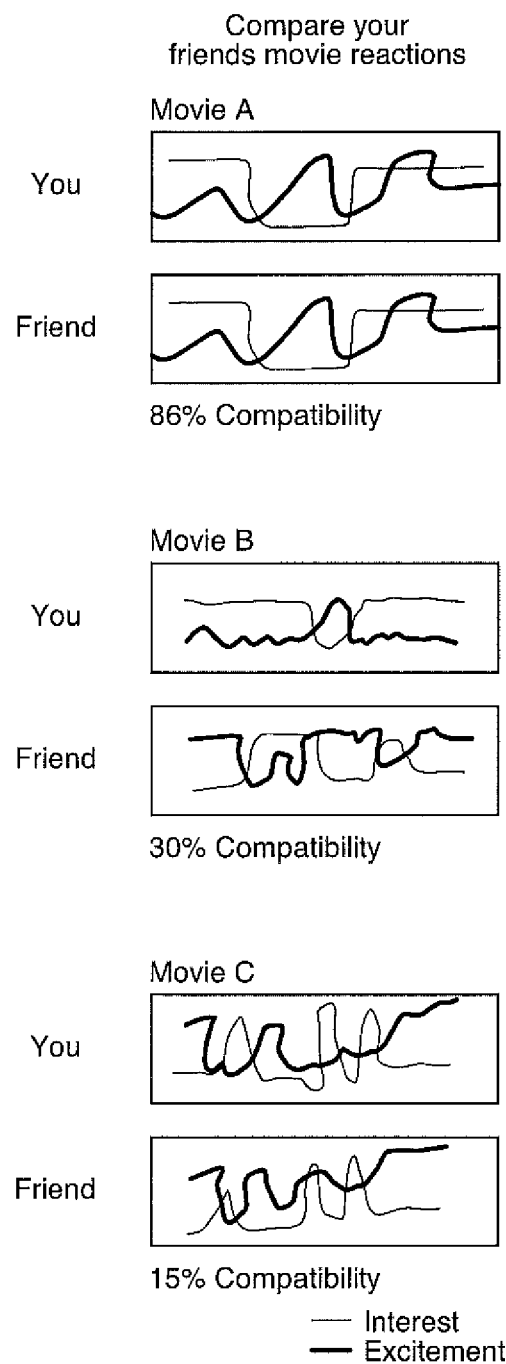
FIG. 36 shows comparing a user's brain state response against the respective brain state responses of one or more other users, in accordance with an aspect of the present invention.

FIG. 36 shows a non-limiting implementation of the present invention, where a user's brain state response determined in accordance with the present invention may be compared against the respective brain state responses of one or more other users. As shown in FIG. 36, s first user and a second user may have each watched the same content items, or movies, while having their respective brain states determined and time-coded corresponding to the timing of the respective movie. Each user's brain state response may then be presented in reference to the movie. The computer system may identify similarities or differences in the brain state responses of each of the users, and determine a compatibility match between users based on the determination. Where the respective users are not known to one another, and a high similarity in brain state responses is determined, the computer system may then recommend a friend match between the users. Each user may perform a search for other users having similar brain state responses to the same content, for matchmaking or other purposes. This functionality may be used in connection with an online dating platform for example. As modern society tends to be isolated and saturated with media and advertising that creates unrealistic expectations about relationships and the nature of true emotions, brain states can help make communication more genuine if one party can see that the other party has a similar emotional dynamic or is in the state of mind that is compatible to the party making selections for chatting. While online dating has had success with matching algorithms based on self-report, simply the fact that a chat partner, online date, or even a fellow gamer, has been matched up with a user based on brainwaves will generate the shared context necessary for smooth social interactions. The authenticity of non-voluntary brainwaves matching one with a partner or group online will likely motivate curiosity and openness in an online forum.

Figures 37, 38:
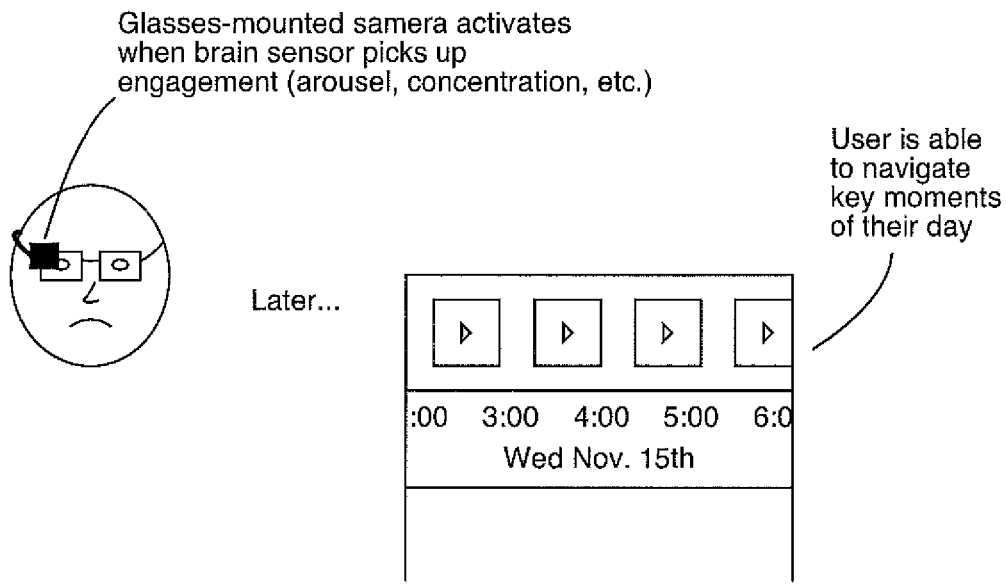
FIG. 37 shows an example of using brain state data with a wearable computing device, in accordance with an aspect of the present invention.
FIG. 38 shows changing an alert notification based on the user's determined brain state, in accordance with an aspect of the present invention.

In another non-limiting exemplary implementation of the present invention, brain state data may be used in conjunction with a wearable computing device such as Google Glass™. As shown in FIG. 37, a user may be wearing a Google Glass-style device including a glasses-mounted camera. The computing device may be configured to activate the camera when a bio-signal sensor detects a particular brain state in the user. The bio-signal sensor may be integrated or attached to the Google Glass device, or may be in wireless communication therewith through Bluetooth or other suitable wireless communication protocol. The user's brainwaves may be monitored for markers of interest. The video camera may be mounted like an eyewear whose camera has the same line of sight as the user looking straight ahead. When the user sees something of interest that is above a particular brain state threshold as determined by a profile or brain state classification rule, the video camera may record what the user is looking at. The device may perform life-logging by keeping track of interesting things during the day. The device may also map the user's location when recording was triggered by something of interest using GPS. Brain state information recorded in this may assist retailers, city planners, or others determine what people find interesting with respect to advertisements out in public spaces, architecture, public performances, political speeches, or other events such as car accidents, etc. The camera may also be activated to record when the user is determined to experience a particular brain state response when seeing, talking to, or meeting another particular person. In this way, first meetings with a future friend, partner, or spouse may also be recorded. This implementation may work in the following way. The user may first turn on a brain state camera application. The user may select to calibrate the application to the user. The rules engine may select a pipeline ID to use with the calibration. The user may complete a relaxation exercise that invokes a neutral state of mind. The user may complete a second exercise that is based on watching an interesting and or entertaining video. A histogram of the distribution of beta brain wave power when relaxed and a second histogram of the distribution of beta power when interested are built. A message with the values of both histograms can be transmitted to the user profile of the user stored in the cloud. The level of interest based on beta power exhibited can be calculated based on the probability by using the reference values in the two histograms. The brain state camera may now be ready to record. The user may select the brain state camera application for active recording. Several pipelines for signal processing, extracting features and classification may be implemented in the application each identified by a pipeline ID. The application may communicate with the cloud platform of the present invention. The pipeline ID may be selected and may be used to extract features for this application tuned for this person (e.g. the histograms of relaxed beta distribution and interested beta distributions discovered during calibration). The pipeline ID may instruct the application to calculate relative beta power from the EEG signal of the user. The EEG along with time stamps are continually being streamed to the cloud. The probability that the user is in an interested state based on their relative beta power is calculated based on the histograms built during calibration. If the probability exceeds a threshold then a signal turns on the video camera. The application assigns a session ID based on calendar date and time. The video and the timestamps of when the recording was started and stopped with each session ID and APP ID is transmitted to the Cloud and stored in the User's profile. The start and stop time stamps are used to identify the segment of EEG signals associated with the video recording along with an Activity Type called "interest based video recording". The time stamps are labelled with start of activity, end of activity respectively. Additional information such as the user's GPS location may also be transmitted to the Cloud. New EEG information may be stored in the user's profile that can be used to enhance the histograms and hence ability to predict the user's level of interest. Additional processing can be done in the Cloud to determine a geographic map of interest. Level of interest and time of day. A plot of interest scores across the day. Analyzing the information in the Cloud across the sessions of the user can determine behavioural patterns that are helpful to the user and help them retrieve videos that he/she has accumulated.

As shown in FIG. 38, in a non-limiting implementation of the present invention, the computer system may change an alert notification (e.g. ringtone) of the user's computing device (e.g. mobile phone) when the user's brain state is determined to be of a certain type. The user's ring tone may therefore reflect the user's mood, or the ring tone may be modified based on the caller's brain state, where the caller is also wearing bio-signal sensors in accordance with the present invention. The ring tone may be adjusted to the user's mood so that the call is less disruptive when the user is in a particular brain state. A ring tone may be shut off when it is detected that the user is annoyed or sleeping. However, some filtering or selective choice of expression is needed depending on the who the called party is as persons express differently to loved ones, colleagues, superiors, etc. Ring tones can be used to create an audible emoticon.

Figure 15:
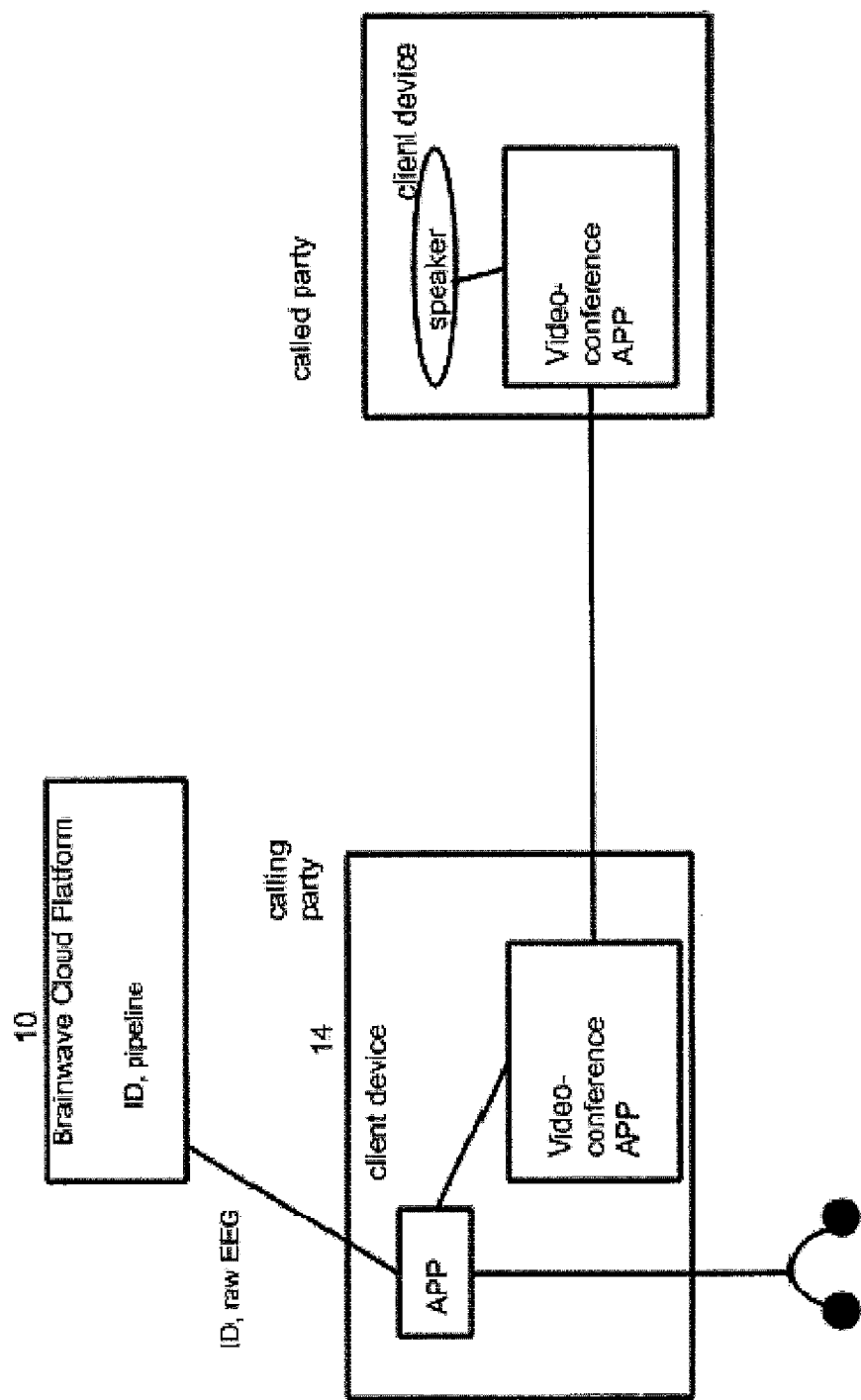
FIG. 15 illustrates a system diagram view of an embodiment of the present invention.

Modulating a ring tone by emotion over Skype may be provided as follows. An application in accordance with the present invention may classify EEG data. The application may send classified emotion to Skype through a web browser or through the Skype application. The calling party may initiate a call with another Skype user (the "called party"). Skype may send a ring tone based on a classified motion of the user wearing the EEG sensors that plays over a speaker of the called party. Furthermore, the present invention may provide for a user communicating with another user may to enhance any such communications with the respective user's brain state such that both users may be able provided with an indication of the user's own or the other user's brain state, or the computing device of one of the users may be configured to modify presentation of the communication based on one or both of the brain states received. The architecture of the present invention for such an implementation may be seen in FIG. 15.

In another non-limiting example a user may effectively provide a comment on content or shared content without explicitly stating an opinion. The user's brain state may be determined and this may be shared to the author or poster of the content without the user having to spend any time composing a comment. In this way, collaboration may occur between users.

Brain State Response to Advertisements

Figure 39:
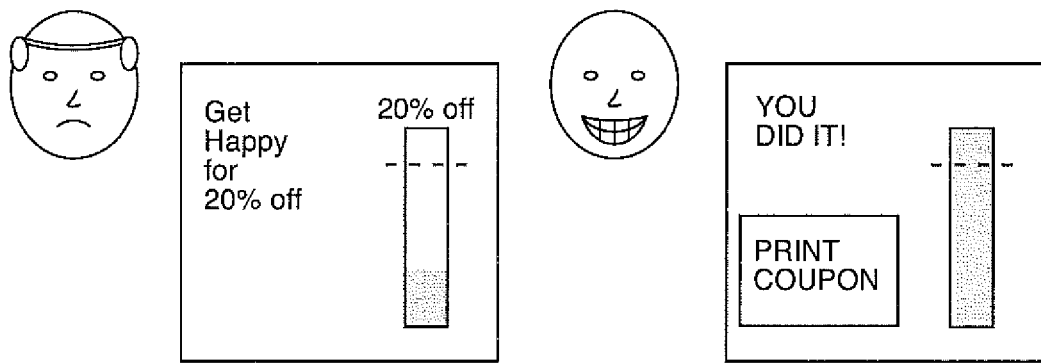
FIG. 39 shows an implementation of an aspect of the present invention, where a user's brain state response may be used to modulate presentation of an advertisement.

FIG. 39 shows a representation of an aspect of the present invention where a user is presented with an advertisement. The advertisement may appear on a web page, overlayed on a video, in a game, or on other digital content. The advertisement may prompt the user to achieve a particular brain state in order to trigger an event. For example, the user may be asked to "get happy" to received a coupon code. The user's brain state is determined and transmitted to the advertisement or computer controlling the advertisement. If the user is able to achieve a happy brain state above a particular threshold, the advertisement may be modified to indicate to the user that the brain state was achieved, and present the user with the coupon code.

There is often a need to make a number of decisions in marketing about product features, style, advertising effectiveness, etc. The status quo for gathering information for marketing is to conduct focus groups, surveys and other means of product testing where potential customers and users are asked for their thoughts and opinions. Neuromarketing is a new field of marketing research that studies consumers' sensorimotor, cognitive, and affective response to marketing stimuli. Monitoring a user's brain waves in real-time in response to interactions with or presentations of advertisements may provide for more information about how users react to particular advertisements, or the products, services, or brands associated with them. While a user is viewing an advertisement, an additional icon or indicator may be shown to the user at the edge of the ad that is an indicator of mood. The user may receive feedback on the user's mood (e.g. increasing smiley face). The advertiser may offer a better coupon based on how strong a brain state response the user is able to achieve. Also, the user may be rewarded to achieve a better mood because when a consumer is in a good mood, the consumer is more likely to buy the product being advertised, or engage with an associated brand in a positive manner.

Focus groups wearing bio-signal sensors of the computer system of the present invention may also be used for testing audience response to a movie or a television show, or to a product such as a new tablet computer or a children's toy. Often directors and producers want to tailor movie endings or key scenes depending on the demographics of their audience (e.g. European, North American). Directors can test different endings of movies with test-audiences to determine which leads to the most entertaining ending.

The emotional impact of online advertising may be estimated by analyzing a person's brainwaves. A web browser may present an advertisement. Timestamps associated with advertising events may be output by the browser along with the brainwaves of the person. The timestamps allow analysis of brainwaves occurring at the same moments as the advertising events. Events may include: click through; pointer brush; click close; and other events. An example of how this can work is through the use of interstitial ads. An interstitial ad displays before a user can access requested content, sometimes while the user is waiting for the content to load. The emotional response of the ad can be assessed for users wearing the bio-sensors of the present invention. It is presumed that people are online while for other reasons and not for the ad itself. Over time advertisers may understand the impact of their content on a user and change the format or type of information or messages that are sent for tailoring to the specific user.

Bidding for Advertising

Figure 16:
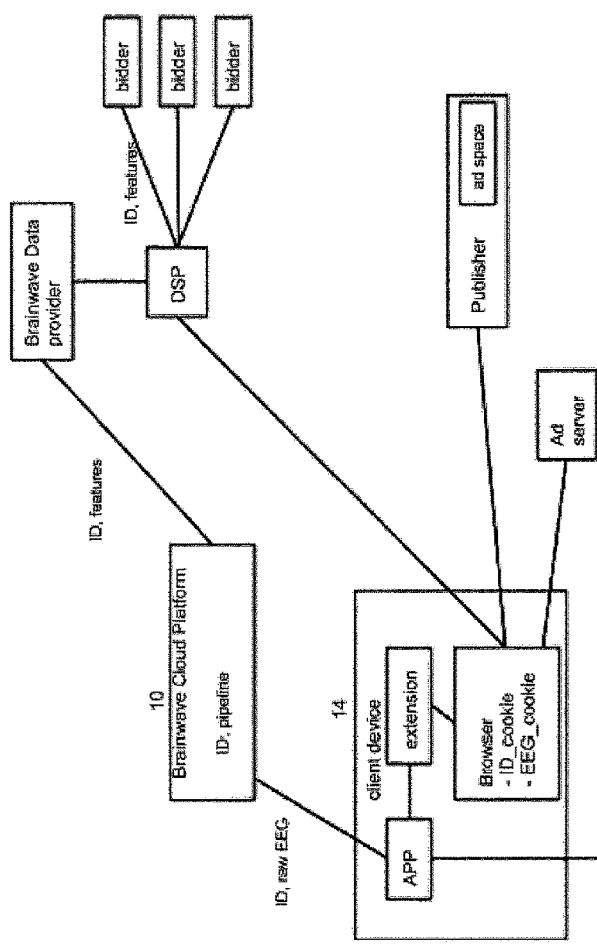
FIG. 16 illustrates a system diagram view of an embodiment of the present invention for real-time bidding for online advertising delivery.

In another non-limiting example, real-time bidding for online advertising delivery may be based at least partly on brain state, and implemented by the architecture shown in FIG. 16. Online advertising uses the internet to deliver promotional marketing information to consumers. Real-time bidding may be executed using for example one or more ad networks. Real-time bidding permits selling and buying online advertising based on computer algorithms that analyze metrics of the consumer. The intent is to increase the effectiveness of advertising by analyzing data about a specific consumer. In current use today consumer information can include, age, gender, geographic location and possibly search engine queries. In this invention, the data about the consumer is supplemented with analysis of the consumer's brain state. The brain state can include longer term metrics over time (e.g. an average of emotions over a long time period) to shorter term emotions. Emotion, mood and feelings may play an important role in a person's financial decision making. When a person is in a good mood, the person may be more likely to be influenced by visual stimulation and hence more likely to make a decision to purchase. Moreover, a person in a good mood tends to be more receptive and open to new products, or encouraged to purchase because the person is more willing to take risks and the person is more likely to buy impulsively. Advertisers may be willing to pay a higher premium for placing ads to users that are in a good mood.

Figure 47:
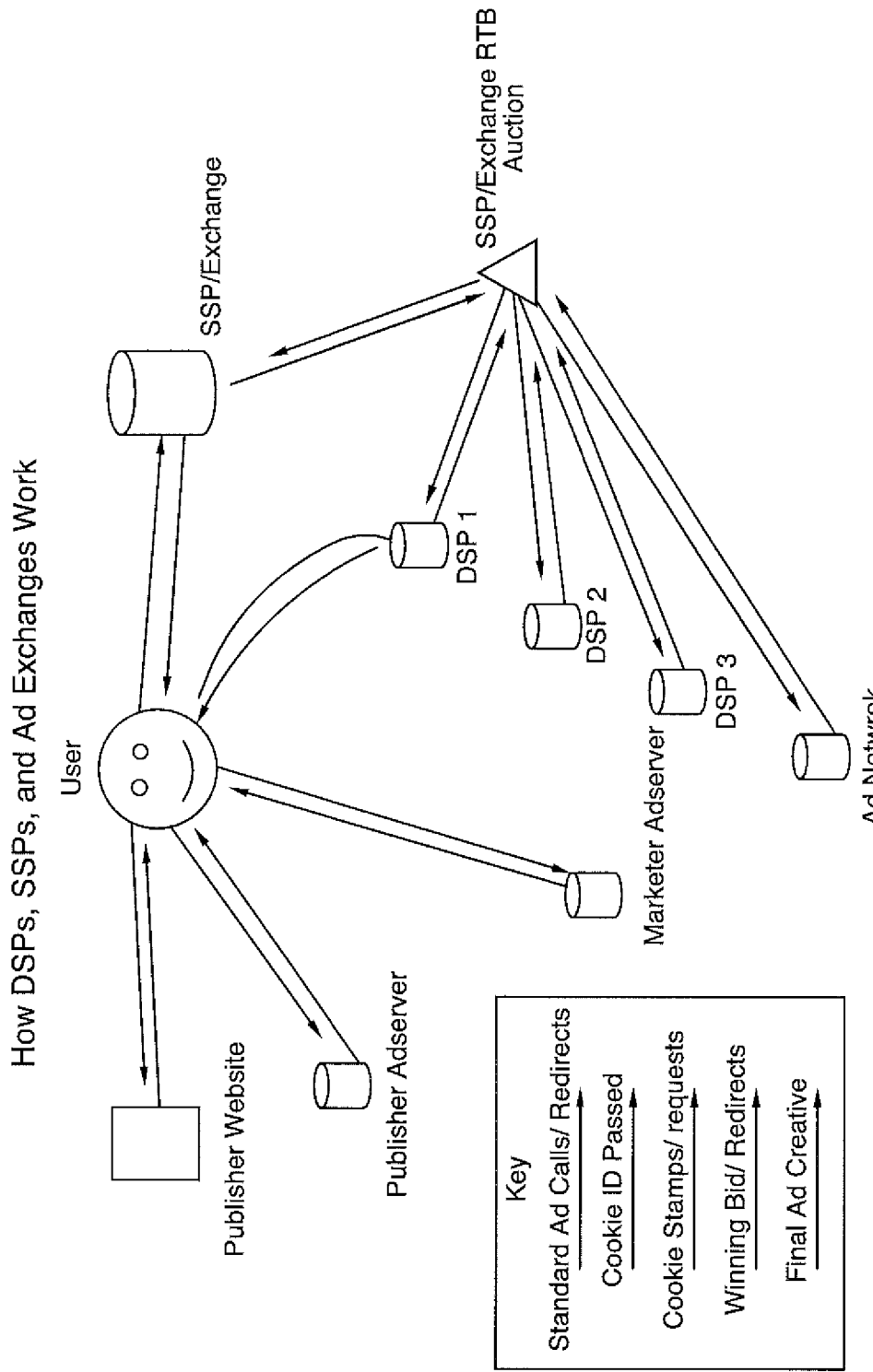
FIG. 47 illustrates how real-time advertising bidding may be implemented.

Real-time advertising bidding may occur as follows, with reference to FIG. 47. A Publisher of a web site supports real-time-bidding to place an ad on a per consumer basis. The Publisher is a supplier of ad space. A user clicks on a link in their browser that sends a query to the Publisher's website. The publisher's web server sends HTML code to the user's browser with the address of where to get the content. The user's browser sends a message to the Publisher's ad server. The Publisher's ad server returns the address (site ID) of a Supply Side Platform (SSP), the publisher's ID and the dimensions of the ad space. The SSP is an exchange that brings together suppliers of ad space (i.e. Publisher) to advertisers bidding for ad placements. If the user has a cookie ID associated with that SSP, the user's browser sends a bid request along with their cookie ID to the SSP. Large SSPs in the USA have 90% coverage of the US internet population. The SSP starts the auction. The SSP sends messages to each advertisers' Demand Side Platform (DSP) with the user's cookie ID, the URL the ad will be delivered to and the user's frequency of visits is for that site. Each DSP determines the value of placing that ad by considering the information they have about the user. The cookie ID sent by the user is searched in the DSP database to find data about the user. The DSP sends a bid back to the SSP. The SSP picks the winning bid and sends the address of the winning adserver back to the user's web site. The user's browser displays the ad.

Advertisers may be willing to pay more than the normal rate for ad impressions associated with consumers with specific characteristics (e.g. 10 times more than the normal rate). Also, consumers are willing to give up some privacy to brands that they like. The user is aware that advertisers will have access to features of their brainwave data. They may allow this because of incentives offered by advertisers, or the user is willing because they are offered some control over the content they receive. This is particular true of consumers who have become "advocates" of a specific brand.

In exchange for having their brainwave features available to advertisers, the user may be able to control the quality (i.e. reduce annoying ads), or source of ads (e.g. not receive ads from a particular political party) and control content (e.g. favour ads that have pleasant scenery) of advertising messages that they receive.

Figure 17:
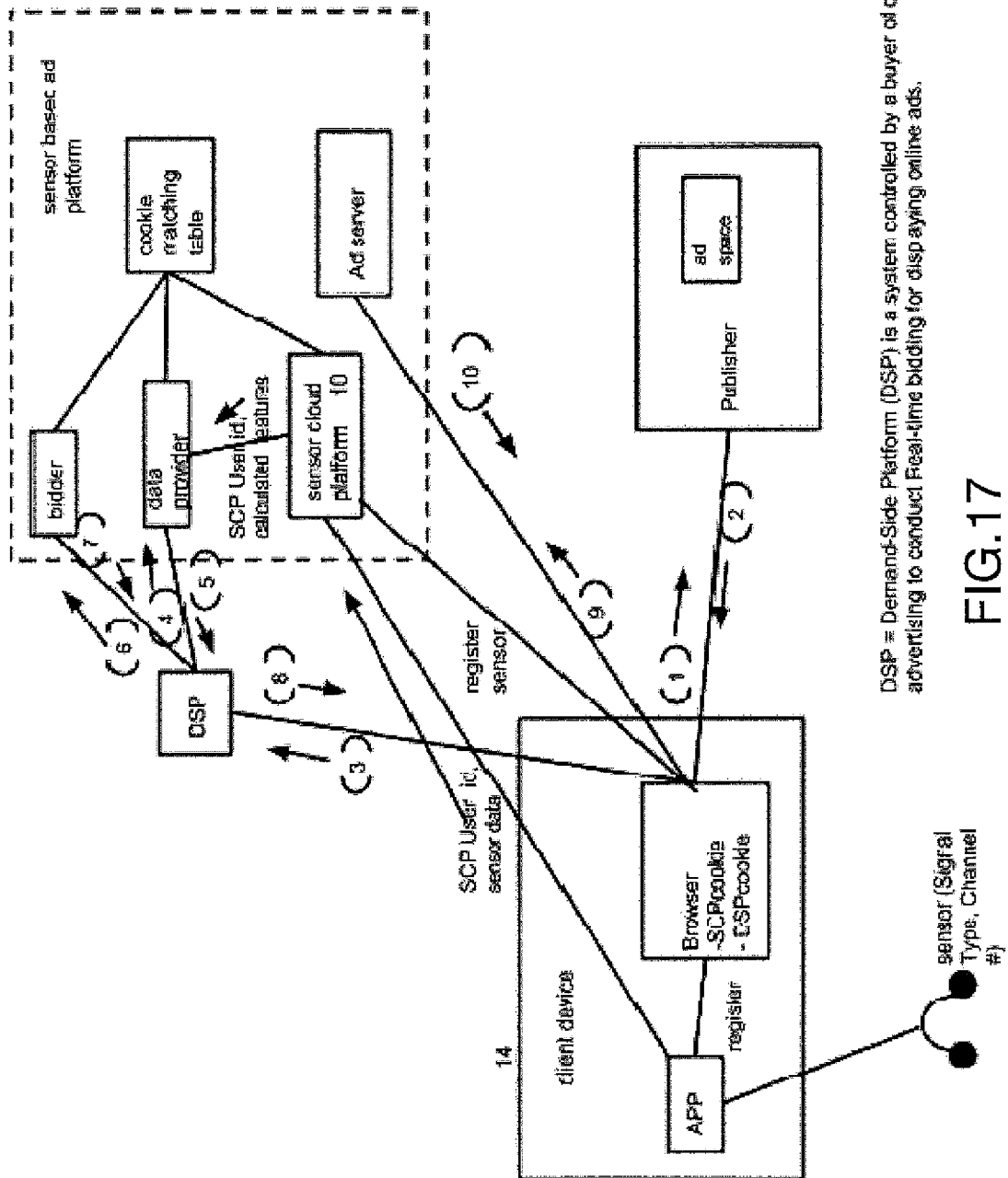
FIG. 17 illustrates a system diagram view of an embodiment of the present invention for real-time bidding for online advertising delivery enabled via a sensor application.

In a non-limiting example, real time bidding for online advertising may be enabled via a sensor application, as shown in FIG. 17. A Publisher web site has ad space to sell to advertisers. They sell the space based on a bidding process across advertisers competing for the ad space-real-time-bidding. The Demand Side Platform (DSP) is an exchange that brings together suppliers of ad space (i.e. Publishers) to advertisers bidding for ad placements. Data Providers (DP) are connected in close proximity to a DSP to allow them to return data quickly to a DSP (e.g. 10 ms). Sensors can be biological sensors or other kind of sensors hosted by the client device (e.g. outdoor air temperature thermometers, other environmental sensors, accelerometers, light, environmental molecules, ambient sound, wind speed, water temperature, etc.). A user with a client device (computer) with one or more attached sensors (e.g. EEG headset) opens an application on the device that manages connectivity and streaming of data of one or more sensors. The user logins into the Sensor Cloud Platform (SCP) with a User ID and password for authentication. Raw sensor data is streamed from the application to the Sensor Cloud Platform (SCP) with the information as per PCT Patent Application No. PCT/CA2013/000785 (e.g. session id, signal type, channel #, etc.) header in the streamed sensor data. The APPLICATION invokes each browser on the client device instructing it to send an HTTP query to the SCP with its SCP user ID (i.e. John Doe). The SCP sends a HTTP response back with a set cookie instruction that is uniquely associated with that SCP user ID called SCP cookie (for example SCP789 and the SCP user ID in the cookie, e.g. John Doe). The SCP selects a pipeline that classifies sensor data into features/predictions of interest to advertisers. The SCP applies the Algorithm Pipeline ID in the User's profile by looking up the User ID to find the corresponding algorithm pipeline for analyzing sensors associated with online ads. It extracts features from the user's sensors and applies a classifier to predict a state, e.g. mood. The SCP calculates either the sensor features, its prediction (e.g. good mood) or both. The SCP sends on a frequent periodic basis (e.g. every 100 ms) features/predictions to Data Providers (DP) along with the SCP user ID. Cookies may be synchronized in the following way. The DSP has previously seeded the internet with DSP cookies using a unique User ID for each browser that has received an ad from an auction the DSP has run. Large DSPs have 80-90% reach rates to the US internet population (See ref.: http://www.adopsinsider.com/ad-serving/diagramming-the-ssp-dsp-and-rtb-redirect-path/). A new entry is entered into the Cookie Matching Table whenever the bidder has won an ad placement. The Cookie Matching Table allows the sensor based ad platform to associate SCP User IDs and hence sensor based information about that user for future auctions involving the user's sensors.

The cookie matching table keeps track of associations among cookie IDs based on previous winning bids. On a previous visit by the user's browser to a web page with real-time bidding for online ads, the DSP sets a cookie in the browser, e.g. DSP456 as shown in the cookie matching table example below. Anytime after the DSP cookie is set, the user's browser visits a website with ad space for auction, the browser is redirected to a DSP. The bidder enters DSP456 for this auction into the cookie matching table. The bidder wins this auction and sends an ad placement to the user. The User's browser is informed where to get the ad and embedded in this response is the DSP User ID. The DSP User ID uniquely identifies this user across all online ad auctions. The user's browser sends an HTTP request to the Ad server with the DSP User ID. The ad server responds with the ad and the cookie SCP789(John_Doe) and the user's browser stores the SCPcookie. The ad server associates Cookie Matching Table is completely filled based on winning this auction. Other Cookie Matching schemes are available as described in the prior art. For instance, Google runs an external Cookie Matching Service (see ref.: https://developers.google.com/ad-exchange/rtb/cookie-guide). Matched cookies allows the sensor based ad platform to associate future bid requests with a particular SCP based User ID. This will allow subsequent ad auctions that involve this user to use sensor information to make an informed decision for bidding on an online ad.

An example of a row of a cookie matching table may include: DSP User ID=DSP456; SCP Cookie ID=SCP789; SCP User ID=John_Doe; and Signal Type=EEG, Heart Rate, etc.

A method implementing the architecture of FIG. 17 may be as follows. The user clicks on a link in their client device browser, e.g. www.acme.org. Client device sends an HTTP query to www.acme.org (denoted in FIG. 17 as reference (1)). At reference (2), the Publisher's website sends the address of a DSP with the publisher's ID and the dimensions of the ad space to the client device browser. At (3), the client device sends its DSPcookie to the DSP. At (4), the DSP sends a request for data to its data providers with the DSPcookie. The DP looks up the DSP cookie in the Cookie Matching Table and finds the associated SCP User ID of this user. At (5), the DP returns the sensor features of one or more Signal Types of the SCP User ID, as calculated by the SCP, to the DSP. The features may be real-time or an historic average or aggregation across a long period of time. The DP has 10 ms to return its response. the DP has cached data from the SCP indexed by SCP User Id and calculated features or predictions of the sensor data. This cache allows the DP to respond quickly to queries since features are based on features/predictions that are already calculated. At (6), the DSP starts the bidding process by sending calculated features/predictions to bidders along with the DSP User ID associated with the browser that initiated the web request to the publisher. At (7), each bidder determines the value of placing that ad by considering the information they have about the user including the calculated features/predictions (e.g. mood classification). The bidder may also have historic features of the user. Other information of the user is searched in their database to find all data available about the user. In the case that the sensor is off, the bidder may want to consider historical information that it has received and or stored about the user. The bidder sends a bid back to the DSP. At (8), the DSP picks the winning bid and sends the address of the winning ad server back to the user's browser. At (9), the user's browser sends an HTTP request to the ad server. At (10), the ad server fills the ad space and sends the graphics animation etc to the user's browser to displays the ad.

An advertising system can determine whether or not the user clicked through. The SCP is still receiving sensor data from the User. During and after the ad has been placed, the SCP calculates sensor features/prediction based on the sensed reaction of the user. Over time advertisers will understand the impact of their content on a user and change the format or type of information or messages that are sent tailored to reaction (e.g. emotion) of the user.

Figure 18:
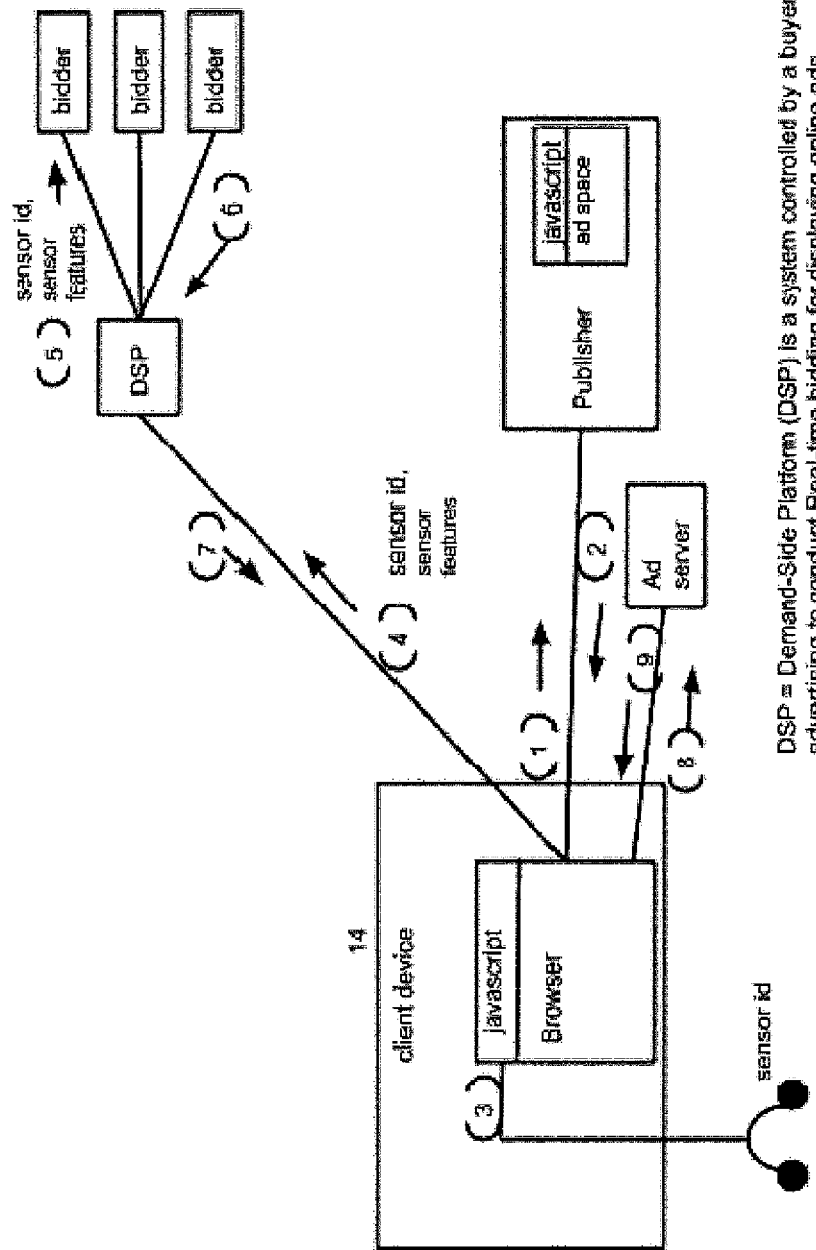
FIG. 18 illustrates a system diagram view of an embodiment of the present invention for real-time bidding for online advertising delivery enabled via instantaneous reading of sensors.

In a non-limiting example, real time bidding for online advertising may be enabled via instantaneous reading of sensors, as shown in FIG. 18. At (1), the user clicks on a link in their client device browser, e.g. www.acme.org. Client device sends an HTTP query to Publisher www.acme.org. At (2), the Publisher's website sends the address of a DSP with the publisher's ID and the dimensions of the ad space to the client device browser with JavaScript to determine the sensor id and sensor data. At (3), the JavaScript runs on the client's browser and it gets sensor id and sensor data/ features. At (4), the client's browser sends the sensor id and sensor data/features to the DSP. At (5), the DSP starts the bidding process by sending sensor features to bidders. At (6), each bidder determines the value of placing that ad by considering the information they have about the user including the brain features and mood classification. The bidder may also have historic brainwave features of the user. Other information of the user is searched in their database to find all data available about the user. In the case that the sensor is off, the bidder may want to consider historical information that it has received and or stored about the user. The bidder sends a bid back to the DSP. At (7), the DSP picks the winning bid and sends the address of the winning ad server back to the user's browser. At (8), the user's browser sends an HTTP request to the ad server. At (9), the ad server fills the ad space and sends the graphics animation etc to the user's browser to displays the ad.

Figure 19:
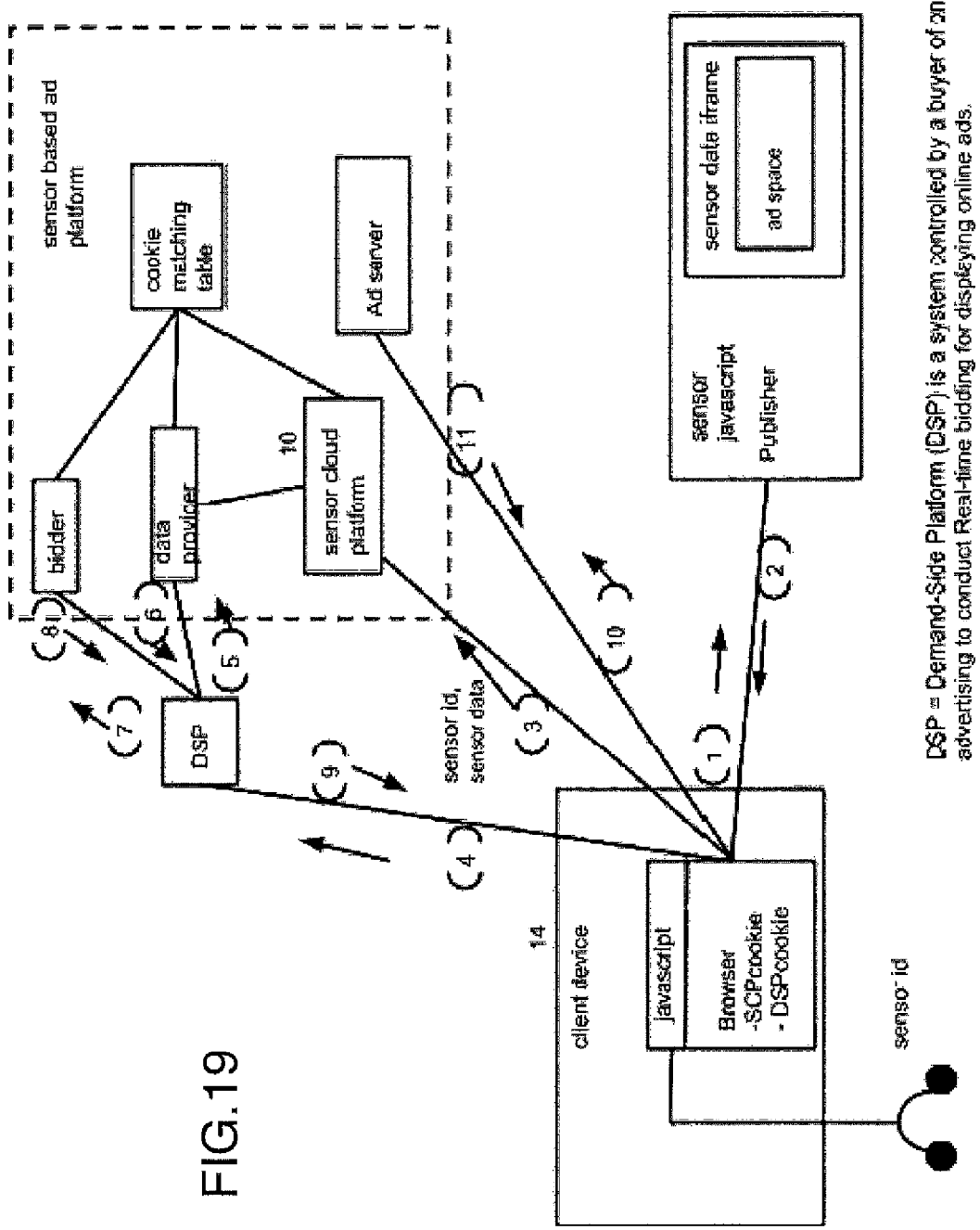
FIG. 19 illustrates a system diagram view of an embodiment of the present invention for real-time bidding for online advertising delivery enabled via streaming sensor data requested by browser JavaScript.

In a non-limiting example, real time bidding for online advertising may be enabled via streaming sensor data requested by browser JavaScript, as shown in FIG. 19. This option may require cooperation from a Publisher's website to embed JavaScript to redirect sensor streams to sensor cloud platform. At (1), the user clicks on a link in their client device browser, e.g. www.acme.org. The Client device sends an HTTP query to www.acme.org. At (2), the Publisher's website sends the address of a DSP with the publisher's ID and the dimensions of the ad space to the client device browser. The Publisher's web site also sends JavaScript to the user's browser. At (3), the JavaScript runs in the user's browser. The JavaScript obtains the sensor id and sends it and streams sensor raw data to the sensor cloud platform. At (4), based on the HTTP code delivered in step 2. The user's browser sends DSPcookie to the DSP. At (5), DSP sends a request for data to its data providers with the DSPcookie. The DP looks up the DSP cookie in the Cookie Matching Table and finds the associated sensor ID of this user. At (6), The DP returns the sensor features of the sensor id as calculated by the SCP to the DSP. The features may be real-time or an historic average or aggregation across a long period of time. The DP has 10 ms to return its response. the DP has cached data from the SCP indexed by sensor id holding calculated features of the sensor data. This cache allows the DP to respond quickly to queries since features are based on features that are already calculated. At (7), the DSP starts the bidding process by sending sensor features to bidders along with the DSPcookie associated with the browser that initiated the web request to the publisher. At (8), each bidder determines the value of placing that ad by considering the information they have about the user including the brain features and mood classification. The bidder may also have historic brainwave features of the user. Other information of the user is searched in their database to find all data available about the user. In the case that the sensor is off, the bidder may want to consider historical information that it has received and or stored about the user. The bidder sends a bid back to the DSP. At (9), the DSP picks the winning bid and sends the address of the winning ad server back to the user's browser. At (10), the user's browser sends an HTTP request to the ad server. At (11), the ad server fills the ad space and sends the graphics animation etc to the user's browser to displays the ad.

Feedback on Performance

Figure 41:
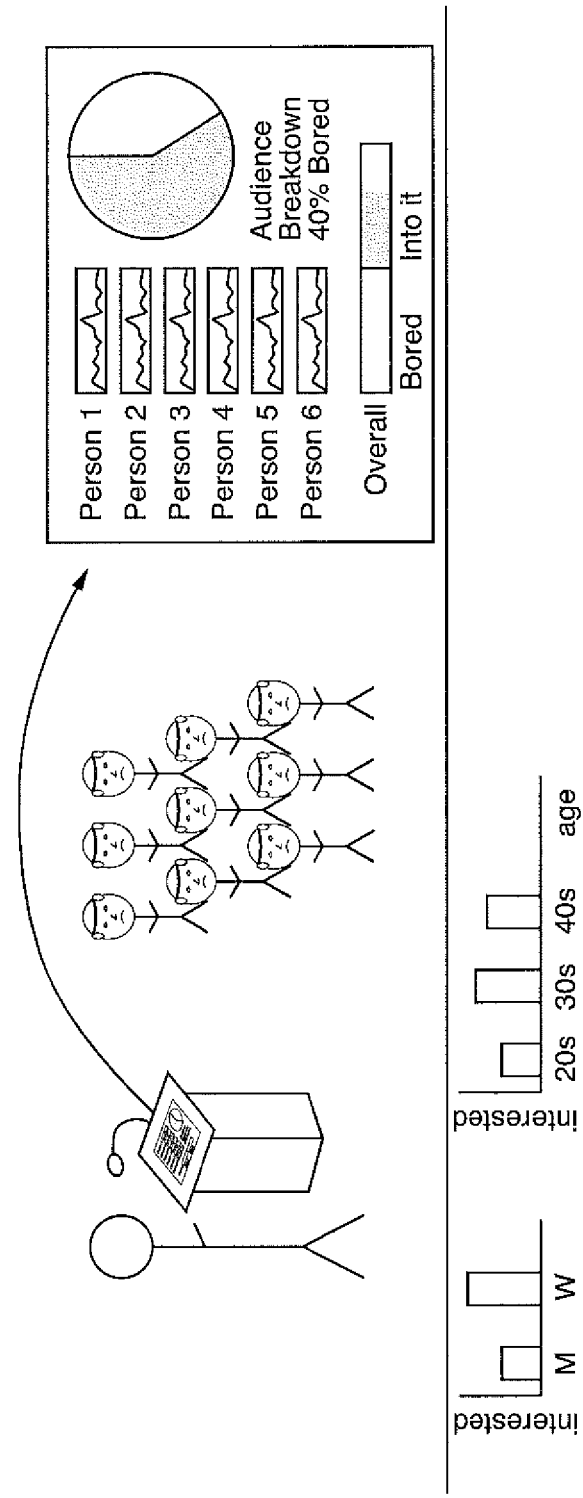
FIG. 41 shows an implementation of an aspect of the present invention, where brain state feedback may be received during a public performance.

There are many situations where people seek to feedback on their performance either during practice, preparation or rehearsal or during a venue where a person is performing a task with upon or in front of others. This can include a number of categories such as business people making a sales presentation or pitch to investors, an educator in front of a classroom, a business person making a report during a meeting or teleconference call, a healthcare worker providing a service for another person. Brain state can add a deeper dimension to feedback by eliciting feedback that a person themselves may not be able to voice such as the depth of focus, moreover minimizing bias that people may have. For example, you could note the parts of a presentation that are interesting by monitoring P300s, both their presence or amplitude, or other event related potentials (ERPs). You could assess audience member's emotional state, or like/dislike (using frontal alpha asymmetry, for example), or level or focus or attention (using, for example, frontal beta, frontal mid-line theta, or other measures), or level of drowsiness/alertness. This could be assessed for a single audience member, or averaged across a number of audience members. For example, a teacher performance may be based at least partly on brain states of the students. A new teacher can develop the teacher's teaching style in front of students by monitoring the efficacy of the teaching approach on the attention garnered from the students. The effectiveness of an investor pitch may also be tested prior to making the presentation to actual investors, by using brain state data of an audience receiving the test pitch. An example of performance feedback for public speaking is shown in FIG. 41.

There may also be applications for speech writing. A politician or executive may wish to test and optimize a speech by examining the emotional impact their speech is having on a test-audience at particular points in time. A test-audience wearing headsets including bio-signal sensors of the present invention may listen to a draft version of the speech. Their emotions are captured at each point in time of the speech. The test-audience emotional response is compared to the intended emotional profile that the politician/executive wishes their audience to experience. With an understanding of the differences of the actual compared to the intended emotional responses, the speech can be modified to optimize emotional response.

Public speaking is a major source of anxiety in people, and it is also one of the most important transferable skills to be successful in the modern world. whether you are in business, politics, academia, or even service, your ability to communicate in front of people defines your success to some degree. The ability to use brain state to get genuine, involuntary responses sidesteps the usual problem of politeness in self-evaluation (especially compared to conventional clicker responses). The fact that public speaking and communication for leadership can only be rated by subjective observers makes it very difficult to evaluate one's performance in any reliable way. Brainwave technology can overcome this obstacle by its reliance on algorithms which can help determine objective response. In addition we have a precise temporal mapping of emotional responses that given manual systems that depend on users pushing a button is more accurate.

Figure 42:
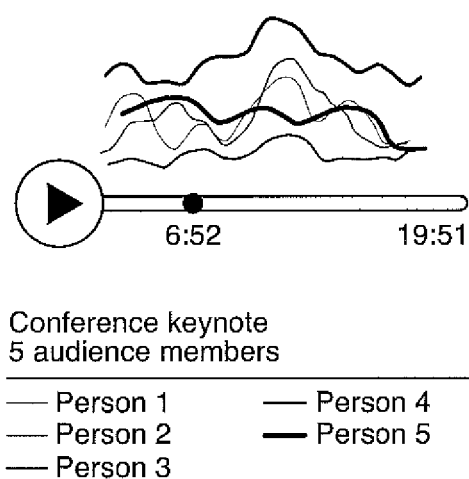
FIG. 42 shows playing back recorded live content together with a presentation of brain state responses of audience members, in accordance with an aspect of the present invention.

An exemplary method of applying brain state feedback for public speaking is described. A user may be engaged to speak at some upcoming event. The user works on a first draft and gets to a first version of the speech. The user may decide to solicit feedback from some group (peers, team, hired sample, etc.). Group members arrive and are given bio-signal sensors of the present invention to wear of the computer system of the present invention. The user may connect a multi-bluetooth peripheral to a computing device. The user starts data collection on the application. The application may detect connection problems or signal quality problems, and the user is informed and instructed on how to fix issues. The application may facilitate calibration of emotions to brainwaves for each user's individual brainwave profile. The user opens dashboard and sees data coming in. The user hits record and delivers a speech to the group. When completed, or at any time, the user may stop recording the data. Multiple interaction modes may be provided including: User can read speech text with emotags compiled from group embedded into the document; User can dive into individual or subset of participants; User can listen to audio recording of speech with audio manifestations of brainwaves overlaid; User can visualize brain data over time; and User can export data, audio, visualization etc. Data types may include: emotion (arousal, valence); focus vs distraction; and focus vs distraction can filter relevance of emotional data to speech. FIG. 42 shows an example of the user playing back a speech and viewing individual brain state responses of speech attendees. Optionally, the brain state responses may be used to modulate the playback of the speech, by varying the volume in accordance with variations in the brain state responses, or by mixing in additional sound effects representative of moments in the speech that provoked particular responses from the audience.

Other applications of receiving brain state feedback on performance may include: Marking School Grades (e.g. A professor wears a headband while marking student tests assignments to detect if they have any bias towards students, the order of marking or if fatigue is setting in); teleconference monitor (e.g. The participants of a teleconference call in an organization can be monitored to help the person with the "floor" determine if their audience is fatigued, bored, and or distracted); Masseuse (e.g. A masseuse can monitor the person receiving the massage for levels of relaxation); Actor's Studio. (e.g. an actor can improve their performance if they have feedback on the actual emotions they are feeling. If a scene requires sadness, then the depth of their sadness can be reflected to them by the computer system of the present invention); Learn Skills by Gaming; Surgical training game; Driving test game, and others.

The present invention may also be used to appraise a person's capabilities to assess a level of competence (e.g. by testing composure under stress of a candidate in a job interview of a stressful job such as an air traffic controller or call centre employee; or in a driving test to track emotions of the person undergoing the driving test).

Augmented Reality Applications

Elements of a scene as viewed through a camera/Google Glass may be modified to appear based on brain state/emotion. For example, if the system detects confusion, a help button can come up. If the user looks at someone the user loves, the EEG could detect the brain state of love, face tracker could detect the face of the person in front of the user (or even do face recognition off of Facebook), and hearts can swim around the person's head on the augmented display.

Other Examples of Modulating Content

Various other examples of modulating content, or modifying presentation of digital content will be described.

Modifying Display of Desktop Icons

Figure 43:
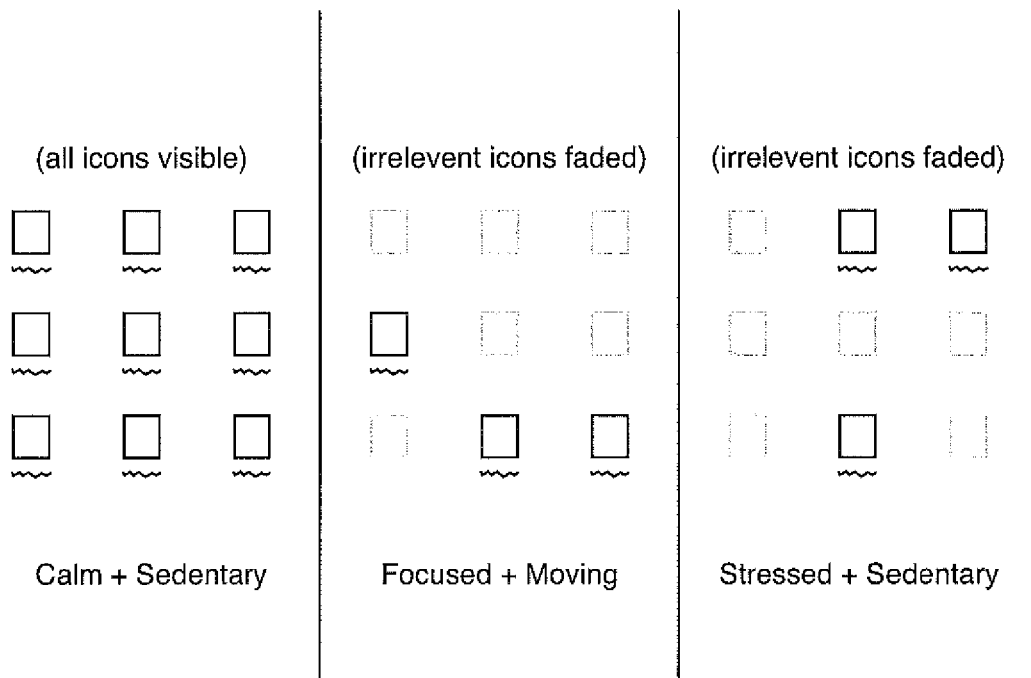
FIG. 43 shows modulating presentation of desktop icons in accordance with an aspect of the present invention.

With reference to FIG. 43, a desktop of icons may be visible on the user's computing device. The display of the icons may be modulated to rearrange the icons on the desktop by the user's brain state. For example, if the user is determined to be calm or sedentary, all icons may be visible. If the user is determined to be focused or moving, irrelevant icons to that brain state may appear faded. Likewise, if the user is determined to be stressed and sedentary, other icons irrelevant to that brain state may appear faded. Accordingly, the system of the present invention may fade irrelevant icons to the user's current context. The bio-signal sensor(s) and an accelerometer connected to the computing device may communicate with the computer system to detect the state of the user and modify the home screen. Other modulations may also be possible based on a combination of brain state and accelerometer. In particular it may be beneficial to the user to minimize the visual load presented to the user when the user is stressed, or when the user is moving, or both.

Encouraging Homework Completion

In another non-limiting example, the user may set a goal to finish homework that has a particular deadline. The user's brainwaves may be monitored by an EEG headband. The system may provide generic rules that apply to all users when they first use the system. The classifier detects the event that the user has become drowsy. The following may be a generic inference rule that applies to all users when they first start using the system: Event="Drowsiness Detected" IF Condition=Critical Activity THEN ACTION="Play Stimulating Music". The user may respond by inputting a manual override command (presentation control command) and turns the music off. This manual intervention is kept in a log with this rule that includes all of the information at the time such as date and time, algorithm used to detect drowsiness. Because of the User's Manual intervention, the ACTION part of the rule may be changed to poll the user's brain or emotional state and more details about the activity. The next time the rule is applied, the system may perform a brief survey of the user's emotional state. The survey determines that the user is apprehensive and they are doing math which requires a great deal of concentration. The survey also determines that the User's preferred action is to get coffee. After getting this self-report, the EEG associated with this event is labelled as stress and added as training data in the User's Profile to the data mining improver. Another rule is added to the Rules Engine. This rule is added to the User's Profile as a discovered rule, and may be defined as follows: Event="Drowsiness Detected" IF (Condition=Critical Activity) AND (Condition=Concentration Required) THEN ACTION="Suggest Getting Coffee".

Fostering Creative Writing

In another non-limiting example, the user may set a goal to create a new work of fiction writing. The user may be facing a blank page and may want feedback on what thoughts or feelings are holding the user back in the creative process. The user wants to use brain training tools to achieve a state of innovative thinking and creative ideation. The method is to detect when the user is having constricting thoughts and or emotions that are getting in their way through mindfulness practice. Mindfulness is the awareness that arises when one places their attention fully and non-judgmentally in the moment. Awareness can be of thoughts, feelings and physical sensations. In this example, the user is new to mindfulness practice and hence the generic rule that is applied is one that tries to improve the user's self-awareness of breath through mindfulness based practice. The generic rule may be defined as follows: IF (Condition=Started Creative Activity) (Condition=Novice Mindfulness Practitioner) THEN ACTION="Suggest Starting with Mindfulness on Present Moment". The action performed by this rule is to provide feedback to the user when either agitation or drowsiness are detected. This exercise is training towards a more creative state of mind. After the user has completed this exercise they will be a more creative state of mind but may still slip back into undesirable states. When the user shifts to creation, the system sets up a timer for periods of time that will ring a chime when the brainwave detects that the user has sustained a period of drowsiness, agitation or exceeded a time limit. For that duration of time the user's brainwaves are monitored and then feedback is given to the user. The user also provides a self report of the quality of their creativity after the chime rings. The emotional profile of this time interval is provided and the user is asked to drop into another mindful exercise. This will replenish the user's creative reserves and allows user to act in full velocity. In addition, this information is added to the User's Profile. This data adds to the training data allowing the data mining improver to analyze the brainwave conditions associated with creativity, drowsiness and agitation to improve the quality of feedback. This rule is expressed as a nested rule as follows: IF (Condition=Creative Activity) (Condition=Novice Mindfulness Practitioner) THEN ACTIONs=[IF "LENGTH AGITATION>5 minutes" OR "LENGTH DROWSINESS>3 minutes" OR "Elapsed Time>10 minutes" THEN "Play Chime and ask user if they want to do a separate refreshing exercise OR "keep working with breath guidance" OR "no interventions please"].

The user may respond to this request and provide feedback that they want to keep working with breath guidance. This preference is updated and the rule is updated to automatically do this action until the pattern of User's manual intervention indicates to change the intervention. Accordingly, the rule may be defined as follows: IF (Condition=Creative Activity) AND (AGITATION OR DROWSINESS DETECTED) THEN ACTION="keep working with breath guidance", IF "AGITATION" Then ACTION=play soothing music AND unobtrusive audio instructions to a breath guide to adjust breathing in real time for long, calm, slow, smooth breaths, IF "DROWSINESS" Then ACTION=play stimulating music AND unobtrusive audio instructions to a breath guide to adjust breathing to Very Deep Breaths.

In this intervention, as agitation is detected then a rule fires. The system may play music that either soothes or creates a higher state of alertness, and there could be a breath guide to adjust breathing in real time. If drowsy then deeper breaths may be encouraged with stimulating music.

In addition, the frequency and quality (or score) of these sessions has been kept track in the User's Profile. If the User reaches a certain level of mindfulness practice then they will have a moderate expert status as expressed by the following rule: IF (User=Brain state of Mindfulness=Moderately balanced) THEN ACTIONs: "USER=Moderate Mindfulness Expert".

Mood Management

In another non-limiting example, applications in accordance with the present invention may be provided that enable users to manage their mood. For example, a user may select that the user wants to be happier. A brain state application may be launched and a base line recording may be made of the user's brain state. The application may suggest a number of ways that the user could get happier, including using a number of applications that modulate content based on brain state and the rules engine of the present invention. The user may select to get happier by watching movies. In the video application, the user may click on a "get happy" link so that the rules engine is notified of the user's intention. The video application may recommend putting on headphones to watch the intro to happiness video (e.g. be shocked with a sound and light show). The short intro allows a baseline reading to be made and it also prepares the user to get happy watching videos. In other words, the rules engine in an evaluation mode may create stimulus as part of the get happy video help determine the user's brain state.

With the data collected from the calibration video and the user's profile, a number of movies to watch may be recommended that should make the user happy. The movies are summarized with a sequence of thumbnails spanning the timeline. The summaries are tuned to the user's profile based on their and other similar user's reaction to the movies. The rules engine may modulate the video content in accordance with happy mode, and present results to the user.

As the user watches the movie, the movie content is modulated in real time in order to tune it to the user's brain-state and to help provide better estimates of brain-state when will be helpful for producing better modulations and content recommendations. The rules engine monitors the user's brain state and controls the modulator.

Inputs received from the user where the rules engine receives the user input requests and implements the appropriate state change include: volume up and down, FFwd, Rwd, Skip (e.g. inputs that builds on the profile for the user and the particular media); Modulation up/down (e.g. inputs that change the intensity of modulation to meet the user's preference, and is an input that control a one or multi-dimensional property); and Modulation tuner (e.g. inputs that change modulation properties in a multi to multi dimensional mapping).

When the movie finishes, or the user presses skip, results may be presented to the user and the rules engine may control results if they serve the end goal. Self report questions may be asked that facilitate the mood transition and the rules engine may control inquiry. New movies may be recommended that use the updated information of the person's mood and real-time reaction to the content that just played and the rules engine may suggest the content.

Where the user is interested in managing the user's mood, the user may wish to stabilize the user's mood, preserve a particular feeling, or stay in a particular brain state once achieving the brain state. Other goals may include: keeping yourself from dropping into undesirable feelings; a safe place to experience an particular negative state and to offer a process for finding your way out (detachment); mood altering; intensifying mood (make movies more exciting); and changing from one mood to another.

The rules engine may need to be able to build up (cluster) states that the user experiences, without necessarily labelling the states. The rules engine may then also need to provide a means of labelling unlabelled states/clusters of states.

User State as it Relates to Content Creation

When the system of the present invention is used to enhance the content creation, or content editing, process, consideration of the different phases of the content creation process may be considered. For example, the user may not want any content modulation during a phase where the user is formatting a document, adding headings, etc. The user may want to record the user's emo-state during the creative process, but not during the composition or editing part of the process, since the permutation of language or word hunting may bear a likeness to the emotional component of the content. Accordingly, in an aspect of the present invention, the system of the present invention may determine a phase of the content creation process in which the user is engaged, and consider the phase determination when applying any modulation rules. For example, the brain-state of the user may be determined by the system of the present invention prior to the user beginning to actively create the content, while the user is only thinking of what to do.

A user may go through various activities in the content creation process. For creation of a text document, the user may imagine, where the user is creatively ideating on plausible content. The user may add content through composition (e.g. converting mental idea into written form), editing (e.g. editing the content to improve its effect), or emotifying (e.g. adding brain-state content as a discrete process, either through the addition of symbols (like emoticons), or modulation of existing content in the document (painting text with feeling—adding color, modifying font, animating the text, etc.)). The user may feel, by perceiving composed content to consider its effect. The user may be inspired by considering other content to provide material for the user's imagination/ideation. Inspiration may also involve content modulation as it may be used to help the user enter or stay in target states, including: Listening to music; Watching videos; Reading content; and Taking part in online conversations/collaborations. The user may also experience inspiration and not want content modulation, when organizing content (e.g. Non-linear busy work, containing actions/additions like: content reorganization, titles/headings, references, links). The user may transition between the imagination, inspiration, feeling, content addition, and organizational phases of content creation.

The system of the present invention may attempt to estimate the phase of content creation, based at least partly on the user's keyboard or UI usage patterns. Optionally, a statistical model of pattern analysis may be improved through monitoring the user's manual selection of phases, and self-annotation. The system may monitor what words are being entered; where the cursor is moving throughout the document; and what part of the document is in view. Estimated brain or bio-state may also be considered when determining the content creation phase, including: brain state; facial expression monitoring; muscle tension; eye-tracking (e.g. one or more methods such as EOG, optical, visual evoked potentials); patterns of usage of the keyboard (e.g. keystroke rate); breathing rate; and body movements as estimated by accelerometer readings or video analysis.

User Interface for Content Creation

A user interface of an app implementing aspects of the present invention may provide controls that allow the user to effectively capture the user's emotional state or brain state, or "emostate" relative to the different phases of content creations, and to apply the emostate to the content either in real-time, or retroactively.

Some system and UI functions may include monitoring and storing user's brain state. The user also may be provided with control to allow the user to retroactively record the user's brain state from some time in the past (e.g. the last minute). This may be important because the user may realize that how the user was feeling in the last moments were relevant to the content that the user is creating. It is hard to feel on command, and easier to recognize how you have been feeling, and how you are feeling in the moment.

The UI may provide control to allow the user to select a phase of content creation so that the system know how to interpret actions and apply modulation rules. Some phases that the user may want easy access to in the interface include: feel; compose; edit; organize/no modulation.

In the feel phase, the system may record the user's brain-state so that it can be post-applied as a modulation. For example, there may be an editing step where the user selects the relevant portion and/or modifies the content of the recording before applying it to the content. Brain-state estimates may be made using the prior knowledge that the user is simply reading or considering what has been written. For example, in the case that the user has the user's eyes closed, or if there is little saccadic movement the system may assume that the user is considering rather than reading.

In the compose phase, the system may have prior knowledge of how to interpret the user's bio-signals based on previous statistics and or calibration that the user has performed to help train the system. With respect to calibration, the user may read a short passage, and then rewrite from memory, or the user may be shown a picture that is to be described in writing. The set of calibration exercises may also may be designed to elicit emotional responses so that they can be more effectively detected during a writing composition task. The system may record the data for doing post-modulation or if the user has selected real-time modulation. The system may modulate the text that is being entered using the user's estimated emo-state. Optionally, the system may analyze the user's bio-signals to estimate the user's emo-state, using affect priors that come from analyzing the word that the user has entered for their emotional content.

The system may include a word analyzer component implemented in hardware or software, that extracts context and semantics about text. The output of the word analyzer may supply prior probabilities to the classifier about probability that the text conveys an emotion or some other state. This prior probability is sent to the classifier. The classifier includes the prior probability (e.g. using Bayes Rules) to estimate the probability that the user has a particular emo-state.

In the edit phase, the functions may be similar to the compose phase, except that emo-state priors may also come from the content in the region that the user has selected for editing). If real-time modulation is selected, modulation may be applied to the neighbourhood of the cursor using a curve fitting method, to reveal to the user what the user's current state is, and how added content could affect the document the user is adding to.

In the organize/no-modulation phase, emo-state is not considered, since the user in engaged in a task that is not-conducive to state estimation, or the user feels that the user's state is not relevant in their current task.

Emo-State Editor

Brain-state "emo-state" may be embellished using an emo-state editor, which may be provided in accordance with a non-limiting aspect of the system of the present invention, that allows the user to view the user's state at some point in the past, on a graph where time is one axis of the graph. As the user scrolls and zooms through the timeline, a content display window can also display a review of the user's actions at that point in time. For example during that reading of a document (where the user is in the feeling phase), the content display window may display what part of the document the user was considering at that point in time. There may also be a preview option that allows the user to see the modulation effect using the region the user's has selected. The emo-state editor is also used for content tagging, as well as content creation. For example, if another user has shared some content (e.g. text, video, audio, other) and the user would like to tag or comment using the user's emo-state, the user may record the emo-state and select a portion that may also embellish or be annotated to the content as a response. For example, a user may share a picture to a group of users. Members of the group may respond to the video using short emotags (e.g. perhaps 6 seconds of dynamic emostate). Emotags may be summarized and be included in the display of the content, similar to likes and comment tags currently are in many content sharing applications.

The emo-state editor may allow the user to edit or embellish the user's emo-state. In editing, it may be provided to select a region that is relevant to the content that the user wants to modulate. In embellishment, the emo-state estimator may be producing estimates of the user's level of focus, and present it on the graph, The user may recall the user's affective state at the time, based on the memory cue of the presented time-line and content display. The user could then embellish the graph with the user's affective state by dragging an emoticon onto the timeline An application of the emo-state edited using the editor may include, in a content experience with a definite timeline, such as a video or audio clip, or with text where text-to-speech or a scrolling display window may be used, the association between content and emo-state can be made directly without user intervention. In an asynchronous experience the user may need to apply the emo-state timeline to the content manual using a time-warping operation. A region of text may be selected to apply the modulation. In the option where the text is considered sequentially as a timeline in itself, the emo-state may be applied linearly, or with time based control points that allow for a non-linear warp to align the writing content with the emo-state content modulation. Sections of text may also be considered as a block and the emo-state can be used to modulate it using a rules such as: apply the average emo-state; apply the most extreme emo-state; apply the most-common emo-state; and apply an emo-state timeline as a dynamic modulation through animation (e.g. making the letters dance to your emo-state).

The UI may also provide a means of editing the emostate or blending it with other states in the case that portions of the document are reorganized or the user inserts content.

In an example, emo-state content modulation may be blended with existing modulated content using curve fitting. Typically the curves are fit such that the modulation transitions are characteristic of the user's typical brain state dynamics. For example, instantaneous transitions are not seen in emotional state. Emotional transitions take time, where speed depends on the states the user is transitioning between, the stimulus and the individual. The user may also be presented with manual control to affect the blending operation (e.g. the transition steepness), as there are many instances where the user's own real-time state dynamics are not ideal, which may occur, for example, in the case where the content is related to a discontinuous experience (e.g. like a scene change in a story), or where the content may relate to an experience with discontinuous or non-uniform, or accelerated time.

Youtube Enhancement

In an example modulation of video content, the portion of a video that had the highest positive emotional impact as classified by the user's brainstate may become the thumbnail to represent that video.

An enhancement of video content may include video playback speed enhancement. The user may choose to view a video clip with brain-state speed enhancement, where portions of the video that are un-interesting are played back at a higher speed so that less time is wasted (e.g. all of the clips will be visible but played faster). The user can go back at any time and watch the clip at regular speed. Playback speed is estimated using user's current brainstate combined with the prior information from brain-state observation statistics from other like users, or the current user if the current user has seen the content before. User likeness may be determined through user profile analysis as described herein. The user may provide manual inputs into the player control for controlling playback speed, and these manual inputs may improve any playback speed estimation rules as well as allow the user to have manual control over speed when desired.

Modulating Presentation of Content—Examples

Many ways to modulate presentation of content in accordance with aspects of the present invention may be possible. Further examples or details regarding examples previously discussed are now provided.

Training

Where the user goal is to get better at something, several activities may be available. For example, the computer system may provide prescribed or guided exercises to improve the user's ability at the activity. The user may select a specific goal that may be suggested based on data that has been recorded. Exercises may also be suggested based on the goal. Different exercises may be appropriate given the context or media. The user may want to train with videos, audio, video games, or interaction with other users.

Neurofeedback exercises may be provided where input is taken from the user's bio-signal sensors and other inputs to create or modulate stimulus in real-time that allows the user to learn. The learning may be reward-based learning based on specific brain states. Rewards could be based on different channel than the stimulus (e.g. watch movie, and get popcorn when you are in the right state), or the reward could be in the same channel as the content (e.g. watch movie, and it becomes clearer when you are in the right state).

Training procedures may not require real-time feedback but are comprised of a sequence of steps, and involve content.

The rules engine (modulation controller) may operate to use the output of a signal processor to generate the right real-time feedback to achieve the user's goal, and gather information about a user doing an exercise.

Creation

Where the user goal is to create content, the creation activity may involve feeling, imagining, composing, editing, and getting inspired. Goals of the rules engine may include: providing a short exercise to get the user to start the content creation activity; modulate content so that the user is encouraged to continue the content creation activity; embed brain state information into the content; generate creative insight; getting feedback on contact from others; learning to optimize the different phases (activities) in the creative process; creating content that depends on brain state; discovering what is blocking or dampening creativity.

The rules engine (modulation controller) may need to be able to estimate what activity of the creative process the user is engaged in, so that it can do the right thing (like give real-time feedback or not). The rules engine may need to be able to take user manual input of what Activity of the process they are in (e.g. (Feeling, Imagining, composing, editing, getting inspired). The rules engine may need to take user input about how the user would like the system to function in order to achieve the user's goals (e.g. start/stop/edit an emo-state recording). The rules engine may use the output of signal processor to generate the right real-time feedback to achieve the user's goal.

Social

Social goals of the user may include: enhanced communication (e.g. easier; deeper; and faster, etc.); entertainment; inspiring; regulating mood (e.g. detach yourself from intense mood that may come from a social interaction which is usually negative but could also be related to positive emotions as well); methods for getting in the right frame of mind for relating with others (e.g. exercise interventions, real-time); methods to put two or more people in greater synchrony (e.g. exercise interventions; real-time); generating an extra band of communication that could help overcome miscommunication; validate communications; non-verbal communication; and non-verbal ways of being present with another or a group.

Corresponding goals for the rules engine may include: match other users based on the emotion brain state of a single user; match other users based on type of shared goal; compare brain state of one user to another user (this can be in real-time or asynchronously); create real-time modulation to represent the state of one or more people simultaneously; and create real-time modulation to help people get more in sync with each other.

The rules engine may provide for collaborative brain art/music or a collaborative brain game to achieve the same brain state or to do a brain obstacle course together. The rules engine may provide for multiple users to listen to music together and render real-time engagement or affective state. The rules engine may uses the output of a signal processor to generate the right real-time feedback to achieve the user's goal. The rules engine may use a semantics engine to examine written or verbal text to get an emotional tone, and compare this emotional tone to estimated emotion of user to determine genuineness of communication.

The rules engine may need to know what the user is doing, is responding to, or considering (e.g. which messages in a chat), such as whether a user is doing something unrelated to an emo-conversation.

The rules engine may connect with a social media web site and manage communication therewith.

Content may be recommended driven by emotion. The user's response to recommendations or viewed recommendations, may cause the rules engine to adjust recommendations for the particular user, as the current emotion of the user may be determined to have changed based on the content received.

Content that a user posts may be tagged with the user's emotion when they created they content (Emotagging). The user may have access to emotagged events/posts of the user's friends. A user can search or sort by event and or state.

Personal content may also be tagged by emotion or brain state. A user's social media history may be crawled while recording a user's response. Content is curated that has emotional meaning to user.

The user may also find chat partners that feel the same as the user.

Health Management

In a health management application, goals may include: monitoring across a number of variables; diagnosis (physiological state estimation); asynchronous feedback based on statistics (suggestion to change a behaviour); recommend neurofeedback based therapy; and administer neurofeedback based therapy.

The rules engine may have an evidence database with probabilities of conditions based on measured physiological symptoms plus demographic and user self-report. The database may be tied to personal health records which is an external repository of health information.

The rules engine may estimate a diagnosis based on aggregating probabilities found by measurements and other variables such as applying Bayes Rule.

The rules engine may have a list of recommended strategies and prioritized by cost of level of effort and find common advice that is the root of many problems (e.g. get more exercise, eat more healthily, get plenty of rest, manage your stress better).

The rules engine may track and monitor progress of the user over time to determine patterns of improvement, or rates of improvement or decline (e.g. longitudinal analysis).

An application may include managing/treating a psychological disorder. In this case, a user's brain state may be tracked. Treatment may include the user engaging with exercises that can improve the user's brain state. Performance in the treatment is monitored by the rules engine and may recommend exercises that engages the user. Neurofeedback may be provided for depression or anxiety.

Another application may include early warning of panic attack. A warning cloud may pop up when the user is showing signs of receding into a panic attack. Content can be switched into something that is soothing or relaxing.

Another application may include emotag journal content. A user's emotions may be detected and recorded. These emotions may be used to tag emotionally strong passages that the user may not even be aware of. Text to speech conversion reads the journal back to the user modulated with the emotion that the user felt. The user may experience increased self-awareness. Content could be shared with a spouse or doctor.

Another application may include adding a brain state to a yoga session. Tension in the mind is related to tension in the body. A user can more easily release tension if the user is in the right frame of mind. Guidance can be given to improve self-visualization exercises.

Another application may include a healthcare worker viewing a brain state of a user. For example, a masseuse may see feedback of relaxation/stress of a person receiving massage. The person needs to be relaxed to receive maximal benefits of massage.

Mass Audience Input

For brain state determined for a mass audience, content of a television broadcast may be changed, or a most excited town may receive a film premiere.

Employee Management

For employee management, modulation of presentation of content may include: Test candidate composure under stress-objective evidence of their brain state; Change employee's environment based on focus or stress; Employee monitors emotional state to prepare themselves for meeting; Employee self-monitors for stress, focus etc.; Employee communication enhanced by adding emotional information while they communicate to each other; Managers monitor employee mood and system recommends productivity/fun actions; and Employee wellness increases by having them brain fitness exercises.

Customer Service

For customer service, modulation of presentation of content may include: tech support can see how frustrated user is; priority of callers to call centre changes by frustration level of caller; brain-sensing on call centre employees.

Video Games

For video games, modulation of presentation of content may include: emotions change appearance of an avatar—focus/calm could also improve aim, accuracy, strength, etc.—adapting game mechanics; emotions directly drive game (e.g. provide a game where you have to induce brain states in somebody else like a stand up comedy game; handicap other players' power if you are focussed; if you are sleepy, game difficulty rises); Online Poker (e.g. user cannot play without using the computer system of the present invention; other player sees emotional states as tells; player must suppress these as part of the game).

An avatar may represents a user in a virtual world (e.g. 2nd Life). The avatar can be animated by emotions that are driven by the actual emotions of the user as detected by computer system of the present invention. A profile can be set up that maps the actual emotions of the user to the emotions output by the Avatar. One mapping profile could be that the avatar represents the actual emotions that the user experiences. Another mapping could be to mask and redirect emotions expressed by the avatar to influence other users in the virtual world. For example, in a virtual game of poker, the avatar would express emotional responses based on the strength of the hand to facilitate strategies such as bluffing with a weak hand, or acting sheepish when holding a strong hand and vary the responses so as not to be predictable by other players.

Education

In an education environment, students may be monitored to determine how the students feel when being taught material. Monitoring the students may help to determine when to intervene and what to focus on. For each student determine a time of day when the student is most receptive to learning. This may help the teacher determine when to teach difficult subjects (e.g. teach math in the morning or afternoon). Monitor how well students are doing (online e-learning). Course material may be modified in response to be more difficult or easy.

Monitoring special needs students may provide for early detection of an episode.

An instructor may determine which course material is effective by examining brain states of the whole class, and adjust content and learning style accordingly.

Level of student focus/stress may change course content.

For language training, spoken sentences (cadence, speed, emphasis) may be re-modulated to optimize recognition of words.

For speed reading, pace and format may be modulated to ensure it is effective.

Emotional Intelligence

It can be therapeutic for a user to understand the emotion(s) the user is feeling. This could occur in a therapist/patient setting or within a support group. Emotional intelligence could be taught by compiling the statistics of emotions across a classroom in response to scenes or photographs. Another example of classroom teaching is the impact of music on emotion. For example, Daniel Levitin along with Kitchener Waterloo orchestra played a piece of Beethoven to an audience and then polled the audience as to which of 7 emotions were evoked. The histogram and statistics of responses were displayed back to the audience. It was instructive to learn that 80% of the audience had chosen the same emotion.

Enhanced Communication Tool for People with Cognitive Deficits

People that have difficulty expressing themselves (e.g. autistics, people with dementia) can use the computer system of the present invention to represent their emotions to people around them. This would make it easier to understand a person with a cognitive deficit. A caregiver can more easily recognize when the person being cared for is upset or agitated but may not have external signs of agitation.

Actor's Studio

An actor can improve his or her performance if the actor can receive feedback on the actual emotions the actor is feeling. If a scene requires sadness, then the depth of the actor's sadness can be reflected to the actor by the computer system of the present invention.

Mood Ring/Mood Headband

A person's emotional state can be displayed as jewelry such as a headband that has colour and intensity of light to represent their emotions. The purpose of to have fun in a social setting. This is similar to the popular mood rings that change colour depending on the warmth of the user's fingers.

Journal or Diary Entries

Entries in a diary may be enhanced with actual emotional state as characterized by the Muse. This could be a good complement to therapies such as Mindfulness Based Cognitive Therapy.

Video Modulation

The present invention may be used to provide real-time modulation of video from a camera/augmented reality.

Content Modulation Generally

Types of modulation of content may vary based on the type of digital content. For videos and movies, content modulations may include: trails on motion; reduced saturation (less emotional content, becomes more audio centric, perhaps more motion centric; increased contrast, edge detection, selective blurring.

For audio content, content modulations may include: increased volume; audio event intensification (e.g. increased volume for events; decreased background audio for events to make movies scarier, if it is not intense enough, or if the user's attention is waning); pitch shifts and discord creation in order to change the mode (e.g. detune slightly to make melody droop flat in order to make it sadder); add reverb to increase spatial content and increase immersion; make audio monaural if the user is in a distracting situation or are trying to concentrate on something and a high coherence is noticed between the music and the user brain waves.

For text content, content modulations may include: font face; colour; font animation (motion attracts attention). If the computer system of the present invention is used in conjunction with an eye tracker, it may be possible to determine per-word brain state responses for the user. Words can blink and generate ERPs. The text reader may be presented with a sound accompaniment based on text content and brain state. The reading environment could also be modulated in order to achieve a particular goal.

The present invention may provide positive feedback magnifying the range of experience (trip out). Emotional states may modulate the visual field with filters that match the user's mood, thereby accentuating the user's mood. For example, slow laziness can be indicated by rendered motion trials, silliness can be indicated by fun colors, attention and focus can be indicated by accentuated edges.

The present invention may also be used to reflect negative feedback to stabilize the experience. For example distraction may be reflected with a narrowing of visual field, and colour may be varied to reflect excitement or lack thereof.

The present invention may be used to for modulation of audio content such as a recording prepared using a microphone or a musical track. For example, enhancements may be provided based on the present invention in order to magnify the experience by modulating the frequency response by tuning out for example low frequencies and boosting the highs with greater attention). Musical content for example may be enhanced by introducing high levels of alpha waves.

The present invention may be used to modulate content that helps a user fall asleep. The present invention may be used to introduce feedback of the sound of your own breath and modulate the sound with your brain-state. Negative feedback may be used to dampen out emotions. When a user experiences anxiety, sounds may be modulated to be more reverberant with the reverb model being tuned by a user's specific state. This draws the mind's attention outwards toward the environment and away from internal thought. As the mind becomes quiet (emotional states conducive to sleep), the sound may be modulated to becomes closer and drier (less processed), producing a sound that is less engaging and more relaxing and provides a better foundation for sleep entry.

The present invention may also be used to provide a steerable microphone array that modulates the sound to improve SNR in noisy situations. An array can be pointed (either using hard or soft selection) to amplify sounds from a particular direction of interest. A lock in algorithm tracks the user's response using brain-state estimates of auditory strain.

The present invention may be implemented as a real-time modulation filter for picture or video capture. The present invention may be used to embed the emotional state of the photographer, using filters that set a mood, for example for use in conjunction with a photo sharing application such as Instagram™.

The present invention may be adapted so that one or more possible enhancements are presented, and these may be selected or rejected by the user. Selections may be used to capture user preferences over time.

The present invention may be used to modulate music based on how a first user experiences the music, for the purpose of sharing the experience with one or more other users. This may be accomplished by modulating frequency response (for example by tuning out the low frequencies and boosting the high frequencies, so as to modulate relative attention paid to music segments). Different filter associations may be chosen much like presets on a graphic equalizer so that the user's affective state embellishes the music in a fashion that makes sense given the genre or specific musical composition.

The context of an activity may also be determined and considered by the rules engine when determining a modulation to apply. A microphone may be connected or in communication with the user's computing device. The computer system may then monitor ambient acoustic noise input captured by the microphone to determine engagement of ambient environment and content. A level of engagement with the outside world may then be determined so internal audio may be modulated to mask the ambient noise.

Other non-limiting content modulation applications may include: 1. Compare your brain state to the brain state the Author had when writing the book; 2. Compare your brain state to the brain state the Musician or Singer had when recording the song; 3. Have your brain state response to music also connected to the lights in your home OR project some wicked images on the laptop or TV screen to enhance the experience in a visual form; 4. For the drawing application, have colours change while the person is sketching based on their brain state and/or the line styles could also change from precise and fine to jagged and thick; 5. Couples therapy: use during sessions to ensure both parties are engaged while listening to each other; 6. Picture therapy: use headband and look at a series of picture to understand which photos evoke desired responses, that way you can choose a screen saver or desk photos that continues to promote those positive states of mind; 7. Eating tracker: to detect how well you're focusing on your food (which helps with diet) and which foods have the most powerful positive responses and also when your brain indicates you're no longer enjoying the food and you're stuffing your face because that's your pattern (personal experience here); 8. Which TV shows give you the most pleasure or cause the most angst so you don't get riled before you go to bed so you can sleep better; 9.

Long distance driving exhaustion indicator to use when driving long distances to alert you when you're unable to focus or are too tired and you need a few minutes before continuing; 10. Environmental setting tests for Autistics—detecting which situations cause them to ramp up faster—restaurant with lots of lights and music, dark places, etc. and being prepared, eg. having quieting headphones available or other calming activities; 11. Emotional testing for interviewing emergency workers, flight controllers—who can stay calm in test simulations (might be good for screening of people who work with kids for particular emotional responses); and 12. Testing optimal work environments (desks, lighting, window exposure, etc.).

Pass-Codes and Security

An individual's brain state or emotion, or other brain characteristic could be used to unlock or gain access to secure areas, new services, or new information.

In the security context, this could be providing access to banking, computer passwords or home. In the gaming context, this could be unlocking levels. In the customer service context, this could be improving your experience or triggering rewards for being nice to the customer service person.

Here we also do it with emotion, optionally interfacing with the cloud system of the present invention. The user must be in the right emotional state in order to do it.

Or perhaps what you are opening is your partner's "heart" (a graphical representation shown when communicating between users), and when you are both in the same and "right" state (ie one of compassion, love, sharing, etc), then the heart unlocks.

Digital Secretary

Typically, executives, for example, have secretaries. Individuals who are hired to support their needs. These are business needs (scheduling appointments, answering phones, sending correspondence), but they require knowledge about the individual and his or her state, needs, desires, emotions, fears, etc. For example, a secretary will know not to put through a call from a certain person if the executive is in a bad mood. Or she may know that the executive gets sleepy after lunch, and that is not a preferred time to schedule meetings. As digital tools increasingly replace human actions in our lives, it is important for these digital tools to continue to know information about the user they are serving, such as mood, level of alertness, receptivity to new information/cognitive load, etc.

EEG and other bio-sensing tools give our digital devices the information required to understand the state of the user, and then make decisions in the background based on the state of that user.

For example, if the users brain state is beginning to indicate sleepiness by increased slow wave activity, or the presence of markers of stage 1 or stage 2 sleep (K complexes, sleep spindles), the users devices could modulate their activity accordingly, such as turning off notifications, dimming screens, dimming lighting in the house, not putting through calls, etc.

We can use the cloud to track state long term, build heuristics and models for the person of what they want, what they want to do at those times, etc., and respond accordingly).

E-Mail or Chat Integration

The user's mail may be organized based on the user's emotional state when creating or viewing the email message, which may be associated with the email message. The computer system of the present invention may tag the user's email based on how it makes the user feel. An icon may be provided for each e-mail indicating how much the e-mail made the user focus. Filters may be provided to modulate e-mail text based on how the user feels to disempower any negative affect. Such modulation may include introducing words, scrambling words, introducing colours, images, art, sparkles, etc.

When composing an e-mail message, the text may be modulated based on the user's brain wave data and any corresponding rules.

An emo component to group composition may be provided in a document management service like Google Docs to allow people to encode how much they are focusing/reacting to different areas of the document, like a real-time highlighter. Separate filters may be available that would allow the user to view things like how much a viewer was thinking, trying to focus, failing to focus, like, or dislike the document.

With collaborative document creation, it may be good to see the emotional state (brain state as content) of any document collaborators. An activity cursor could also be included to indicate the respective user's affective state (e.g. focused/distracted/frustrated/thinking/etc. . . . ).

Youtube Integration

The computer system of the present invention may interface with a service like Youtube to provide for recommended video views based on the user's brain state. The video recommendations may shuffle with the user's changing brain state.

Media can slow down or pause if the user becomes distracted during a part that is important to the user. For example, a certain character is talking and the user has shown prior interest to this character. This type of analysis is made easier if the computer system has access to other people's responses to watching the clip, or if the author or another software has done a content analysis.

The media can also speed up if the user is bored.

Video thumbnails or preview clips can be auto-thumbnailed (rather than simply taking the middle of the clip, or auto summarized by your real-time emo-state or your brain-wave profile).

User input of fast forward or particular video selection can be used for learning.

When users watch videos together, or at different times brain state data from those users may be used to modulate the viewing of the video (e.g. adding in laughter, or boos, or other embellishment that might be related to watching as a group). The audience watching the video may also be rendered around the video frame in real-time.

A crowd sourced editor may be provided that allows feedback from early publishing to be visible in the editor to allow you to make better videos.

The rules engine could be configured to make a video more or less powerful based on the rules engine setting and how the user is reacting to the content. For example, if the user is relating to the sound track, that could be accentuated in parts of the video that others or the author found/intended to be dramatic. The soundtrack could be adjusted to maximize entrainment with the user's brainwaves.

Couples' Tools

Resonance between a user's brainwaves and the particular vibrations produced by a stimulator could be rendered as a modulated like, or modulated sound (e.g. sound of breath with modulated overtones of vibrational stimulator when high coherence is found).

A measure of coherence between both people and the respective stimulators may be recorded so that both users can see when they are in phase or not.

Entrainment may be rendered in the feedback of the stimulus itself.

Different Types of Sensors

The present invention may be used with various different types of sensors. Sensors for collecting bio-signal data include, for example, electroencephalogram sensors, galvanometer sensors, or electrocardiograph sensors. For example, a wearable sensor for collecting biological data, such as a commercially available consumer grade EEG headset with one or more electrodes for collecting brainwaves from the user. For example, bio-signal data may include heart rate or blood pressure, while non-bio-signal data may include time, GPS location, barometric pressure, acceleration forces, ambient light, sound, and other data. Bio-signal and non-bio-signal data can be captured by the internal sensors, external sensors, or both.

The distinction between internal and external sensors refers to whether the sensor is contained within a client device such as a mobile computing device or not. For example, a smart phone may have a plurality of built-in internal sensors for collecting non-bio-signal data. External sensors, such as wireless headsets or other types of sensors, may complement or replace the available internal sensors.

Various implementations of the computer system are possible. For example, various different applications may be developed that utilize the computer system and enable different types of biofeedback systems. A few examples of such applications are provided below, along with explanations on how these would utilize some of the contributions of the present invention.

The present invention may be used in conjunction with various types of EEG hardware. EEG hardware may be used in conjunction with the present invention that has various features including for example:

(a) a comfortable form that allows the electrodes to make good contact without pressure points;
(b) dry sensor technology, being easy and quick to put on, comfortable to wear, as well as being stylish so that it can be worn in public;
(c) an on-board 3-axis accelerometer that enables motion input for games and quantifying head movements; and
(d) a wireless connection to a mobile device, for example using a Bluetooth™ connection.

A headband may be used that produces bipolar readings using AFz as the reference from AF3, AF4, TP9, TP10. A 4 electrode montage may enable estimation of hemispheric asymmetries (with an emphasis on the pre-frontal lobe) and thus facilitates brain-state discrimination that depend on this, such as emotional valence (positive vs. negative emotions).

EEG signals may be over-sampled near 20 KHz, band pass filtered and re-sampled yielding to achieve a selectable output sampling rate from 100 Hz to 600 Hz, with 2uV RMS noise. Active noise suppression may be achieved with a DRL-REF feedback configuration using centrally positioned frontal electrodes.

Input range of an AC coupled signal (low cut-off at 0.5 Hz) may be 2 mV p-p.

The EEG hardware may use four electrodes, giving better signal to noise ratio than single channel systems for aggregate measurements and thus better access to high-beta and gamma bands (fast oscillation EEG signals), which are particularly important for analyzing cognitive tasks such as memory, learning, and perception.

The present invention may include a client computer program component. The client computer program may receive the EEG data and input form one or more sensors (such as an accelerometer or heart rate monitor) as well as application state and time markers from application-generated stimulus in the form of audio, video and, vibration. The collected data may be time synchronized to support ERP analysis, stimulus entrainment etc. Online analysis is performed on the client device to support real-time feedback in the application and the raw data is compressed and uploaded to the cloud to support more advanced analytics. An online component may aggregate the bio-signals, and application data such as text and corrections initiated by the user to support the development of additional applications and algorithms.

Other Feedback Modalities

Feedback through a haptic or tactile feedback device, such as a vibrotactile device may also be provided or modulated, such as in a mobile phone, pager, vibrator, or other vibrating element in a device. Vibrotactile feedback can be directly proportional to brainwaves. For example, the more over the threshold of a certain band or state, the more intense the vibration, as controlled by the rules engine. For example, one's attention on a subject could be represented by beta band activity. As one's focus intensity increases, power of beta also increases, and the intensity of the vibration of a motor inside a device (such as cell phone), could also increase.

Emotions or liking, disliking or anger could be represented as such. For example, if one is angry, the state could be transmitted to a tactile actuator, and the movements of the actuator could become more violent, stronger or faster. Likewise, calming could be represented as such as well, and could be communicated.

Another example of vibrotactile feedback is someone thinking about a friend, and that friend's phone buzzing to share that the first person was thinking about them. Another example may be a user configuring the phone such that every time he or she feels feelings of love or affection, the user's child's phone or partner's phone or best friend's phone can vibrate. Like emotion can be used to annotate text message, so can these communications be shared through vibrotactile feedback (e.g. an "I'm thinking about you" buzz).

Vibrotactile feedback can be proportional in intensity, respond in different frequencies, through different frequencies of pulsing buzzes, or other methods of expressing through vibrotactile feedback.

Vibrotactile feedback can also be in the form of music, the vibration of a stereo system being transduced in such a way as it can be physically felt by the user, such as in a bass shaker.

Additional feedback modalities may include: temperature, changing shapes, clothing, smell, and others. Emotional and state information captured by brainwaves could also be shared via temperature, texture or smell. For example, if someone is angry, a target device could heat up (change temperature) as a means of signalling and transmitting mood. By means known in the art such as moving motors, actuators or solonoids, or modulating substances like Nitol that change shape when a current is attached, the target device could be or have a flexible surface that changes shape based on response. For example, one could wear clothing, and when one is angry, the edges of the clothing could curl up.

General

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

Figure 46:
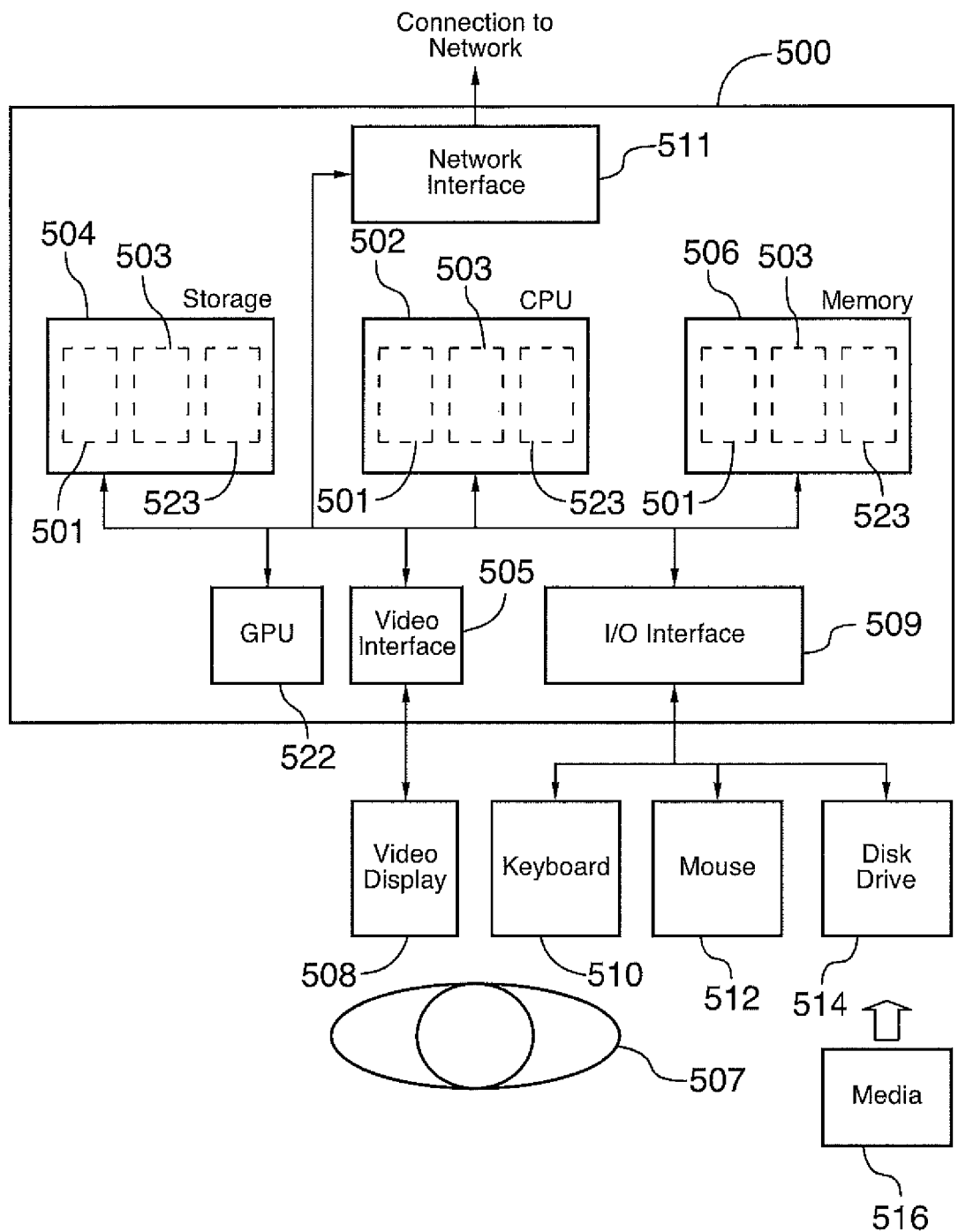
FIG. 46 illustrates a generic computer used to implement aspects of the present invention.

The present system and method may be practiced in various embodiments. A suitably configured computer device, and associated communications networks, devices, software and firmware may provide a platform for enabling one or more embodiments as described above. By way of example, FIG. 46 shows a generic computer device 500 that may include a central processing unit ("CPU") 502 connected to a storage unit 504 and to a random access memory 506. The CPU 502 may process an operating system 501, application program 503, and data 523. The operating system 501, application program 503, and data 523 may be stored in storage unit 504 and loaded into memory 506, as may be required. Computer device 500 may further include a graphics processing unit (GPU) 522 which is operatively connected to CPU 502 and to memory 506 to offload intensive image processing calculations from CPU 502 and run these calculations in parallel with CPU 502. An operator 507 may interact with the computer device 500 using a video display 508 connected by a video interface 505, and various input/output devices such as a keyboard 510, mouse 512, and disk drive or solid state drive 514 connected by an I/O interface 509. In known manner, the mouse 512 may be configured to control movement of a cursor in the video display 508, and to operate various graphical user interface (GUI) controls appearing in the video display 508 with a mouse button. The disk drive or solid state drive 514 may be configured to accept computer readable media 516. The computer device 500 may form part of a network via a network interface 511, allowing the computer device 500 to communicate with other suitably configured data processing systems (not shown).

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:
1. A system comprising:
a computing device;
a bio-signal sensor in communication with the computing device;
the computing device configured to:
receive digital content for presentation by the computing device;
acquire bio-signal data from a user using the bio-signal sensor;
compute a current brain state of the user based at least in part on the bio-signal data; and
modify presentation of the digital content based at least in part on the current brain state, a target physiological state and a presentation modification rule associated with the digital content.

2. The system of claim 1, wherein the target physiological state is a target brain state.

3. The system of claim 2, wherein the computing device is further configured to determine whether the current brain state achieves the target brain state.

4. The system of claim 1, wherein the modification of presentation of the digital content includes presenting positive feedback to encourage the user to achieve the target physiological state.

5. The system of claim 1, wherein the modification of presentation of the digital content includes presenting negative feedback to discourage the user from remaining in a non-target physiological state.

6. The system of claim 1, wherein the target physiological state is a target emotional state.

7. The system of claim 6, wherein the target emotional state is at least one of creative, focused, or calm.

8. The system of claim 1, wherein the target physiological state is a relaxed brain state.

9. The system of claim 1, wherein the target physiological state is a happy brain state.

10. The system of claim 1, wherein the target physiological state is a target meditation state.

11. The system of claim 10, wherein the computing device is further configured to determine whether the user is meditating by detecting, from the bio-signal data, an EEG signal correlated with meditation.

12. The system of claim 11, wherein whether the user is meditating is determined by receiving input specifying an activity that is being performed by the user.

13. The system of claim 1, wherein the computing device is further configured to: receive self-reporting of activities performed by the user, and wherein the modification of the presentation of the digital content is based at least in part on the self-reported activities.

14. The system of claim 1, wherein the computing device is further configured to: receive a presentation control command to allow for override of any modification of the presentation of the digital content.

15. The system of claim 1, wherein the computing device is further configured to: transmit the modified presentation of the digital content to a remote user over a network.

16. The system of claim 1, wherein the computing device is further configured to: receive, over a network from a remote computing device associated with a remote user, a brain state of the remote user, the brain state computed using bio-signal data from a remote bio-signal sensor in communication with the remote computing device, and the modification of the presentation of the digital content is based at least in part on the brain state of the remote user.

17. A computer-implemented method comprising:
   receiving digital content for presentation;
   acquiring bio-signal data from a user;
   computing a current brain state of the user based at least in part on the bio-signal data; and
   modifying presentation of the digital content based at least in part on the current brain state, a target physiological state and a presentation modification rule associated with the digital content.

18. The computer-implemented method of claim 17, wherein the target physiological state is a target brain state.

19. The computer-implemented method of claim 17, further comprising presenting positive feedback to encourage the user to achieve the target physiological state.

20. The computer-implemented method of claim 17, further comprising presenting negative feedback to discourage the user from remaining in a non-target physiological state.

* * * * *